United States Patent
Marx et al.

(10) Patent No.: US 11,474,098 B2
(45) Date of Patent: Oct. 18, 2022

(54) DRUG TARGET FOR PREVENTING PATHOLOGIC CALCIUM OVERLOAD IN CARDIOMYOCYTES AND METHODS OF SCREENING FOR SAME

(71) Applicant: THE TRUSTEES OF COLUMBIA UNIVERSITY IN THE CITY OF NEW YORK, New York, NY (US)

(72) Inventors: Steven Marx, Scarsdale, NY (US); Alexander Kushnir, Passaic, NJ (US); Lin Yang, New York, NY (US); Alex Katchman, New York, NY (US); Henry M. Colecraft, New York, NY (US)

(73) Assignees: THE TRUSTEES OF COLUMBIA UNIVERSITY IN THE CITY OF NEW YORK, New York, NY (US); THE NEW YORK PRESBYTERIAN HOSPITAL, New York, NY (US)

( * ) Notice: Subject to any disclaimer, the term of this patent is extended or adjusted under 35 U.S.C. 154(b) by 635 days.

(21) Appl. No.: 16/228,433

(22) Filed: Dec. 20, 2018

(65) Prior Publication Data
US 2019/0250145 A1 Aug. 15, 2019

Related U.S. Application Data

(60) Provisional application No. 62/609,934, filed on Dec. 22, 2017.

(51) Int. Cl.
| | |
|---|---|
| *G01N 33/50* | (2006.01) |
| *A61P 9/00* | (2006.01) |
| *G01N 33/68* | (2006.01) |
| *A61K 31/4422* | (2006.01) |

(52) U.S. Cl.
CPC ..... *G01N 33/5041* (2013.01); *A61K 31/4422* (2013.01); *A61P 9/00* (2018.01); *G01N 33/6872* (2013.01); *G01N 2500/02* (2013.01)

(58) Field of Classification Search
CPC .... G01N 33/5041; G01N 33/6872; A61P 9/00
See application file for complete search history.

(56) References Cited

U.S. PATENT DOCUMENTS

| | | | |
|---|---|---|---|
| 4,140,544 A | 2/1979 | Sill | |
| 4,769,292 A | 9/1988 | Tang et al. | |
| 4,885,369 A | 12/1989 | Uryu et al. | |
| 4,965,155 A | 10/1990 | Nishiguchi et al. | |
| 5,556,992 A | 9/1996 | Gaboury et al. | |
| 5,773,460 A | 6/1998 | Gaboury et al. | |
| 6,555,278 B1 | 4/2003 | Loveridge et al. | |
| 7,008,961 B1 | 3/2006 | Arcadi | |
| 7,044,598 B2 | 5/2006 | Nakada et al. | |
| 7,294,151 B2 | 11/2007 | Pasquier et al. | |
| 7,488,353 B2 | 2/2009 | Speckbacher | |
| 7,560,574 B2 | 7/2009 | Habi et al. | |
| 7,615,640 B2 | 11/2009 | Horiuchi et al. | |
| 7,795,529 B2 | 9/2010 | Horiuchi et al. | |
| 8,383,672 B2 | 2/2013 | Habi et al. | |
| 8,409,564 B2 | 4/2013 | Roy et al. | |
| 8,802,082 B2 | 8/2014 | Roy et al. | |
| 9,156,827 B2 | 10/2015 | Nagano et al. | |
| 9,622,993 B2 | 4/2017 | Springett et al. | |
| 9,636,363 B2 | 5/2017 | Habi et al. | |
| 9,884,889 B2 | 2/2018 | Coleman et al. | |
| 9,962,368 B2 | 5/2018 | McKnight et al. | |
| 9,974,795 B2 | 5/2018 | Funakoshi et al. | |
| 2004/0197268 A1 | 10/2004 | Augelli-Szafran et al. | |
| 2007/0037752 A1 | 2/2007 | Ansorge et al. | |
| 2009/0298820 A1 | 12/2009 | Tsou et al. | |

OTHER PUBLICATIONS

Catterall, Structure and Regulation of Voltage-Gated Ca2+ Channels. Annu. Rev. Cell Dev. Biol. 16:521-55, 2000.*

Popova, A. V., Bondarenko, S. P., & Frasinyuk, M. S. (2016). Synthesis and properties of 2-benzylidene-8, 9-dihydro-7H-furo [2, 3-f][1, 3] benzoxazin-3 (2H)-one derivatives. Chemistry of Heterocyclic Compounds, 52(8), 592-600.

Johnson, L. V., Walsh, M. L., & Chen, L. B. (1980). Localization of mitochondria in living cells with rhodamine 123. Proceedings of the National Academy of Sciences, 77(2), 990-994.

Summerhayes, I. C., Lampidis, T. J., Bernal, S. D., Nadakavukaren, J. J., Nadakavukaren, K. K., Shepherd, E. L., & Chen, L. B. (1982). Unusual retention of rhodamine 123 by mitochondria in muscle and carcinoma cells. Proceedings of the National Academy of Sciences, 79(17), 5292-5296.

Nadakavukaren, K. K., Nadakavukaren, J. J., & Chen, L. B. (1985). Increased rhodamine 123 uptake by carcinoma cells. Cancer research, 45(12 Part 1), 6093-6099.

Forster, S., Thumser, A. E., Hood, S. R., & Plant, N. (2012). Characterization of rhodamine-123 as a tracer dye for use in in vitro drug transport assays. PloS One, 7(3), e33253.

Kubin, R. F., & Fletcher, A. N. (1982). Fluorescence quantum yields of some rhodamine dyes. Journal of Luminescence, 27(4), 455-462.

Jeannot, V., Salmon, J. M., Deuimé, M., & Viallet, P. (1997). Intracellular accumulation of rhodamine 110 in single living cells. Journal of Histochemistry & Cytochemistry, 45(3), 403-412.

(Continued)

*Primary Examiner* — Ruixiang Li
(74) *Attorney, Agent, or Firm* — Booth Udall Fuller, PLC

(57) ABSTRACT

The present invention provides, inter alia, methods for identifying a candidate agent that can treat or ameliorate the effects of a heart condition caused by the effects of abnormal beta-adrenergic receptor activation on calcium levels in cardiomyocytes in a subject. Compositions that include the candidate agents identified by the methods disclosed, and methods of treating or ameliorating the effects of a heart condition in a subject by administering to the subject the candidate agents identified by the methods disclosed, are also provided.

12 Claims, 29 Drawing Sheets
(27 of 29 Drawing Sheet(s) Filed in Color)
Specification includes a Sequence Listing.

(56) References Cited

OTHER PUBLICATIONS

Beija, M., Afonso, C. A., & Martinho, J. M. (2009). Synthesis and applications of Rhodamine derivatives as fluorescent probes. Chemical Society Reviews, 38(8), 2410-2433.

"(Z)-2-(3,4-dimethoxybenzylidene)-8-(2-methoxyethyl)-8,9-dihydro-2H-benzofuro[7,6-e][1,3]oxazin-3(7H)-one," PubChem®: https://pubchem.ncbi.nlm nih.gov/compound/25282492.

"2-[(3,4-Dimethoxyphenyl)methylidene]-8-(2-methoxyethyl)-7,9-dihydrofuro[2,3-f][1,3]benzoxazin-3-one," PubChem®: https://pubchem.ncbi.nlm.nih.gov/compound/72162509.

* cited by examiner

Exhibit C

Fig. S1A
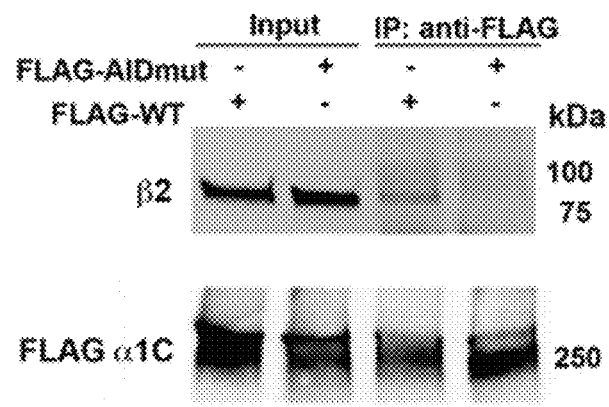
Fig. S1B
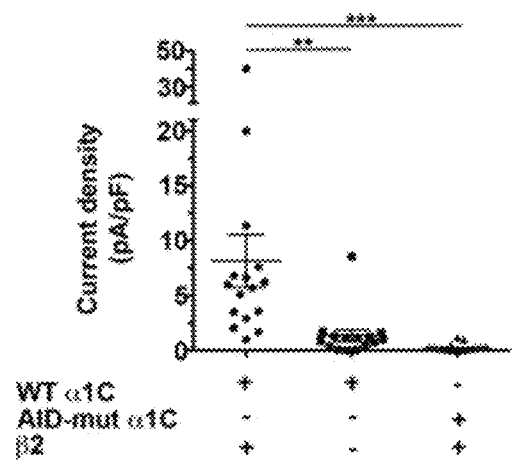
Fig. S1C
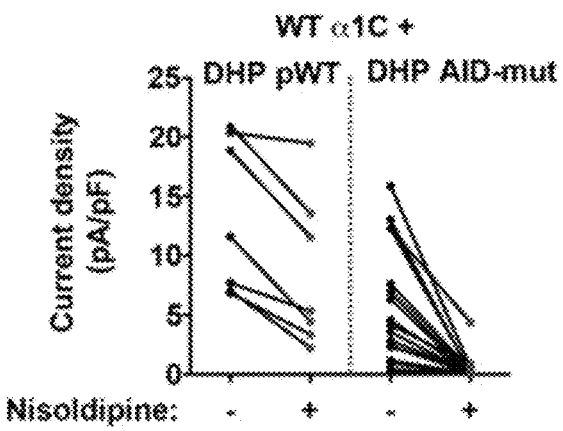

Fig. S2A
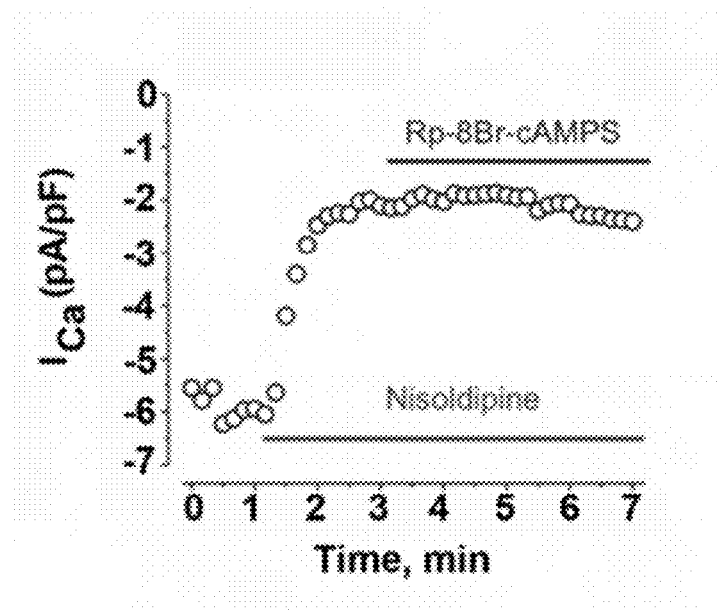
Fig. S2B
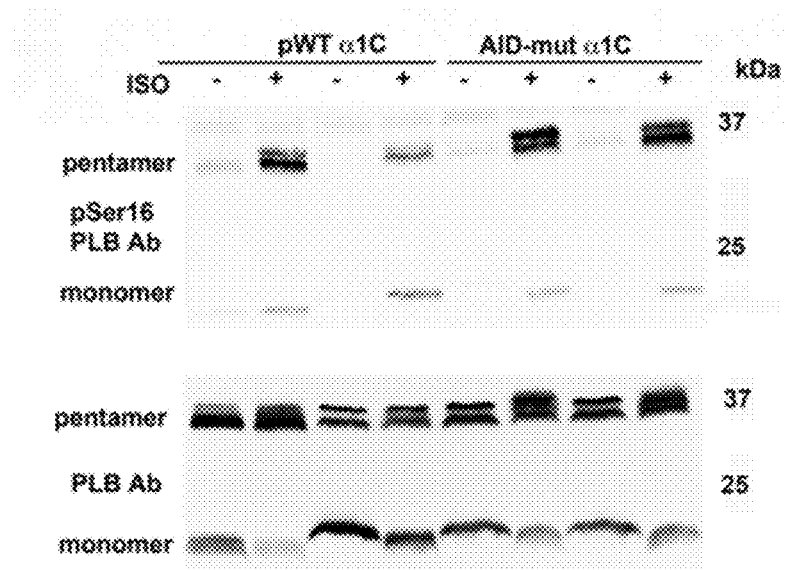

Fig. S3
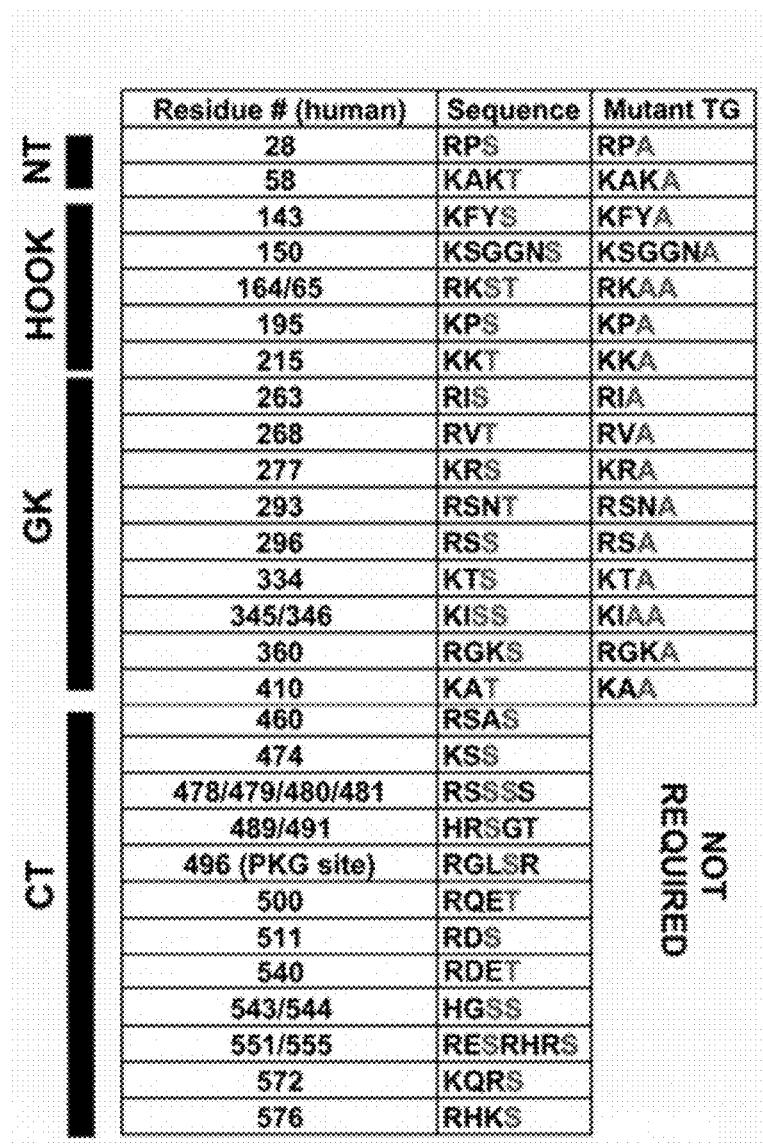

SEQUENCE LISTING

```
<160> NUMBER OF SEQ ID NOS: 208

<210> SEQ ID NO 1
<211> LENGTH: 18
<212> TYPE: PRT
<213> ORGANISM: Lepus americanus

<400> SEQUENCE: 1

Gln Gln Leu Glu Glu Asp Leu Lys Gly Tyr Leu Asp Trp Ile Thr Gln
1               5                   10                  15

Ala Glu

<210> SEQ ID NO 2
<211> LENGTH: 18
<212> TYPE: PRT
<213> ORGANISM: Artificial Sequence
<220> FEATURE:
<223> OTHER INFORMATION: mutant

<400> SEQUENCE: 2

Gln Gln Leu Glu Glu Asp Leu Lys Gly Ala Leu Asp Ala Ala Thr Gln
1               5                   10                  15

Ala Glu

<210> SEQ ID NO 3
<211> LENGTH: 3
<212> TYPE: PRT
<213> ORGANISM: Homo sapiens

<400> SEQUENCE: 3

Arg Pro Ser
1

<210> SEQ ID NO 4
```

```
<211> LENGTH: 4
<212> TYPE: PRT
<213> ORGANISM: Homo sapiens

<400> SEQUENCE: 4

Lys Ala Lys Thr
1

<210> SEQ ID NO 5
<211> LENGTH: 4
<212> TYPE: PRT
<213> ORGANISM: Homo sapiens

<400> SEQUENCE: 5

Lys Phe Tyr Ser
1

<210> SEQ ID NO 6
<211> LENGTH: 6
<212> TYPE: PRT
<213> ORGANISM: Homo sapiens

<400> SEQUENCE: 6

Lys Ser Gly Gly Asn Ser
1               5

<210> SEQ ID NO 7
<211> LENGTH: 4
<212> TYPE: PRT
<213> ORGANISM: Homo sapiens

<400> SEQUENCE: 7

Arg Lys Ser Thr
1

<210> SEQ ID NO 8
<211> LENGTH: 3
<212> TYPE: PRT
<213> ORGANISM: Homo sapiens

<400> SEQUENCE: 8

Lys Pro Ser
1

<210> SEQ ID NO 9
<211> LENGTH: 3
<212> TYPE: PRT
<213> ORGANISM: Homo sapiens

<400> SEQUENCE: 9

Lys Lys Thr
1

<210> SEQ ID NO 10
<211> LENGTH: 3
<212> TYPE: PRT
<213> ORGANISM: Homo sapiens

<400> SEQUENCE: 10

Arg Ile Ser
1

<210> SEQ ID NO 11
<211> LENGTH: 3
<212> TYPE: PRT
```

```
<213> ORGANISM: Homo sapiens

<400> SEQUENCE: 11

Arg Val Thr
1

<210> SEQ ID NO 12
<211> LENGTH: 3
<212> TYPE: PRT
<213> ORGANISM: Homo sapiens

<400> SEQUENCE: 12

Lys Arg Ser
1

<210> SEQ ID NO 13
<211> LENGTH: 4
<212> TYPE: PRT
<213> ORGANISM: Homo sapiens

<400> SEQUENCE: 13

Arg Ser Asn Thr
1

<210> SEQ ID NO 14
<211> LENGTH: 3
<212> TYPE: PRT
<213> ORGANISM: Homo sapiens

<400> SEQUENCE: 14

Arg Ser Ser
1

<210> SEQ ID NO 15
<211> LENGTH: 3
<212> TYPE: PRT
<213> ORGANISM: Homo sapiens

<400> SEQUENCE: 15

Lys Thr Ser
1

<210> SEQ ID NO 16
<211> LENGTH: 4
<212> TYPE: PRT
<213> ORGANISM: Homo sapiens

<400> SEQUENCE: 16

Lys Ile Ser Ser
1

<210> SEQ ID NO 17
<211> LENGTH: 4
<212> TYPE: PRT
<213> ORGANISM: Homo sapiens

<400> SEQUENCE: 17

Arg Gly Lys Ser
1

<210> SEQ ID NO 18
<211> LENGTH: 3
<212> TYPE: PRT
<213> ORGANISM: Homo sapiens
```

```
<400> SEQUENCE: 18

Lys Ala Thr
1

<210> SEQ ID NO 19
<211> LENGTH: 4
<212> TYPE: PRT
<213> ORGANISM: Homo sapiens

<400> SEQUENCE: 19

Arg Ser Ala Ser
1

<210> SEQ ID NO 20
<211> LENGTH: 3
<212> TYPE: PRT
<213> ORGANISM: Homo sapiens

<400> SEQUENCE: 20

Lys Ser Ser
1

<210> SEQ ID NO 21
<211> LENGTH: 5
<212> TYPE: PRT
<213> ORGANISM: Homo sapiens

<400> SEQUENCE: 21

Arg Ser Ser Ser Ser
1               5

<210> SEQ ID NO 22
<211> LENGTH: 5
<212> TYPE: PRT
<213> ORGANISM: Homo sapiens

<400> SEQUENCE: 22

His Arg Ser Gly Thr
1               5

<210> SEQ ID NO 23
<211> LENGTH: 5
<212> TYPE: PRT
<213> ORGANISM: Homo sapiens

<400> SEQUENCE: 23

Arg Gly Leu Ser Arg
1               5

<210> SEQ ID NO 24
<211> LENGTH: 4
<212> TYPE: PRT
<213> ORGANISM: Homo sapiens

<400> SEQUENCE: 24

Arg Gln Glu Thr
1

<210> SEQ ID NO 25
<211> LENGTH: 3
<212> TYPE: PRT
<213> ORGANISM: Homo sapiens

<400> SEQUENCE: 25
```

-continued

Arg Asp Ser
1

<210> SEQ ID NO 26
<211> LENGTH: 4
<212> TYPE: PRT
<213> ORGANISM: Homo sapiens

<400> SEQUENCE: 26

Arg Asp Glu Thr
1

<210> SEQ ID NO 27
<211> LENGTH: 4
<212> TYPE: PRT
<213> ORGANISM: Homo sapiens

<400> SEQUENCE: 27

His Gly Ser Ser
1

<210> SEQ ID NO 28
<211> LENGTH: 7
<212> TYPE: PRT
<213> ORGANISM: Homo sapiens

<400> SEQUENCE: 28

Arg Glu Ser Arg His Arg Ser
1               5

<210> SEQ ID NO 29
<211> LENGTH: 4
<212> TYPE: PRT
<213> ORGANISM: Homo sapiens

<400> SEQUENCE: 29

Lys Gln Arg Ser
1

<210> SEQ ID NO 30
<211> LENGTH: 4
<212> TYPE: PRT
<213> ORGANISM: Homo sapiens

<400> SEQUENCE: 30

Arg His Lys Ser
1

<210> SEQ ID NO 31
<211> LENGTH: 3
<212> TYPE: PRT
<213> ORGANISM: Artificial Sequence
<220> FEATURE:
<223> OTHER INFORMATION: mutant

<400> SEQUENCE: 31

Arg Pro Ala
1

<210> SEQ ID NO 32
<211> LENGTH: 4
<212> TYPE: PRT
<213> ORGANISM: Artificial Sequence
<220> FEATURE:
<223> OTHER INFORMATION: mutant

```
<400> SEQUENCE: 32

Lys Ala Lys Ala
1

<210> SEQ ID NO 33
<211> LENGTH: 4
<212> TYPE: PRT
<213> ORGANISM: Artificial Sequence
<220> FEATURE:
<223> OTHER INFORMATION: mutant

<400> SEQUENCE: 33

Lys Phe Tyr Ala
1

<210> SEQ ID NO 34
<211> LENGTH: 6
<212> TYPE: PRT
<213> ORGANISM: Artificial Sequence
<220> FEATURE:
<223> OTHER INFORMATION: mutant

<400> SEQUENCE: 34

Lys Ser Gly Gly Asn Ala
1               5

<210> SEQ ID NO 35
<211> LENGTH: 4
<212> TYPE: PRT
<213> ORGANISM: Artificial Sequence
<220> FEATURE:
<223> OTHER INFORMATION: mutant

<400> SEQUENCE: 35

Arg Lys Ala Ala
1

<210> SEQ ID NO 36
<211> LENGTH: 3
<212> TYPE: PRT
<213> ORGANISM: Artificial Sequence
<220> FEATURE:
<223> OTHER INFORMATION: mutant

<400> SEQUENCE: 36

Lys Pro Ala
1

<210> SEQ ID NO 37
<211> LENGTH: 3
<212> TYPE: PRT
<213> ORGANISM: Artificial Sequence
<220> FEATURE:
<223> OTHER INFORMATION: mutant

<400> SEQUENCE: 37

Lys Lys Ala
1

<210> SEQ ID NO 38
<211> LENGTH: 3
<212> TYPE: PRT
<213> ORGANISM: Artificial Sequence
<220> FEATURE:
<223> OTHER INFORMATION: mutant

<400> SEQUENCE: 38
```

Arg Ile Ala
1

<210> SEQ ID NO 39
<211> LENGTH: 3
<212> TYPE: PRT
<213> ORGANISM: Artificial Sequence
<220> FEATURE:
<223> OTHER INFORMATION: mutant

<400> SEQUENCE: 39

Arg Val Ala
1

<210> SEQ ID NO 40
<211> LENGTH: 3
<212> TYPE: PRT
<213> ORGANISM: Artificial Sequence
<220> FEATURE:
<223> OTHER INFORMATION: mutant

<400> SEQUENCE: 40

Lys Arg Ala
1

<210> SEQ ID NO 41
<211> LENGTH: 4
<212> TYPE: PRT
<213> ORGANISM: Artificial Sequence
<220> FEATURE:
<223> OTHER INFORMATION: mutant

<400> SEQUENCE: 41

Arg Ser Asn Ala
1

<210> SEQ ID NO 42
<211> LENGTH: 3
<212> TYPE: PRT
<213> ORGANISM: Artificial Sequence
<220> FEATURE:
<223> OTHER INFORMATION: mutant

<400> SEQUENCE: 42

Arg Ser Ala
1

<210> SEQ ID NO 43
<211> LENGTH: 3
<212> TYPE: PRT
<213> ORGANISM: Artificial Sequence
<220> FEATURE:
<223> OTHER INFORMATION: mutant

<400> SEQUENCE: 43

Lys Thr Ala
1

<210> SEQ ID NO 44
<211> LENGTH: 4
<212> TYPE: PRT
<213> ORGANISM: Artificial Sequence
<220> FEATURE:
<223> OTHER INFORMATION: mutant

<400> SEQUENCE: 44

Lys Ile Ala Ala
1

<210> SEQ ID NO 45
<211> LENGTH: 4
<212> TYPE: PRT
<213> ORGANISM: Artificial Sequence
<220> FEATURE:
<223> OTHER INFORMATION: mutant

<400> SEQUENCE: 45

Arg Gly Lys Ala
1

<210> SEQ ID NO 46
<211> LENGTH: 3
<212> TYPE: PRT
<213> ORGANISM: Artificial Sequence
<220> FEATURE:
<223> OTHER INFORMATION: mutant

<400> SEQUENCE: 46

Lys Ala Ala
1

<210> SEQ ID NO 47
<211> LENGTH: 5
<212> TYPE: PRT
<213> ORGANISM: Homo sapiens

<400> SEQUENCE: 47

Arg Pro Ser Asp Ser
1               5

<210> SEQ ID NO 48
<211> LENGTH: 4
<212> TYPE: PRT
<213> ORGANISM: Homo sapiens

<400> SEQUENCE: 48

Lys Ala Lys Thr
1

<210> SEQ ID NO 49
<211> LENGTH: 5
<212> TYPE: PRT
<213> ORGANISM: Homo sapiens

<400> SEQUENCE: 49

Lys Phe Tyr Ser Ser
1               5

<210> SEQ ID NO 50
<211> LENGTH: 6
<212> TYPE: PRT
<213> ORGANISM: Homo sapiens

<400> SEQUENCE: 50

Lys Ser Gly Gly Asn Ser
1               5

<210> SEQ ID NO 51
<211> LENGTH: 4
<212> TYPE: PRT
<213> ORGANISM: Homo sapiens

```
<400> SEQUENCE: 51

Arg Lys Ser Thr
1

<210> SEQ ID NO 52
<211> LENGTH: 3
<212> TYPE: PRT
<213> ORGANISM: Homo sapiens

<400> SEQUENCE: 52

Lys Pro Ser
1

<210> SEQ ID NO 53
<211> LENGTH: 3
<212> TYPE: PRT
<213> ORGANISM: Homo sapiens

<400> SEQUENCE: 53

Lys Lys Thr
1

<210> SEQ ID NO 54
<211> LENGTH: 3
<212> TYPE: PRT
<213> ORGANISM: Homo sapiens

<400> SEQUENCE: 54

Arg Ile Ser
1

<210> SEQ ID NO 55
<211> LENGTH: 3
<212> TYPE: PRT
<213> ORGANISM: Homo sapiens

<400> SEQUENCE: 55

Arg Val Thr
1

<210> SEQ ID NO 56
<211> LENGTH: 3
<212> TYPE: PRT
<213> ORGANISM: Homo sapiens

<400> SEQUENCE: 56

Lys Arg Ser
1

<210> SEQ ID NO 57
<211> LENGTH: 4
<212> TYPE: PRT
<213> ORGANISM: Homo sapiens

<400> SEQUENCE: 57

Arg Ser Asn Thr
1

<210> SEQ ID NO 58
<211> LENGTH: 3
<212> TYPE: PRT
<213> ORGANISM: Homo sapiens

<400> SEQUENCE: 58
```

Arg Ser Ser
1

<210> SEQ ID NO 59
<211> LENGTH: 3
<212> TYPE: PRT
<213> ORGANISM: Homo sapiens

<400> SEQUENCE: 59

Lys Thr Ser
1

<210> SEQ ID NO 60
<211> LENGTH: 4
<212> TYPE: PRT
<213> ORGANISM: Homo sapiens

<400> SEQUENCE: 60

Lys Ile Ser Ser
1

<210> SEQ ID NO 61
<211> LENGTH: 4
<212> TYPE: PRT
<213> ORGANISM: Homo sapiens

<400> SEQUENCE: 61

Arg Gly Lys Ser
1

<210> SEQ ID NO 62
<211> LENGTH: 3
<212> TYPE: PRT
<213> ORGANISM: Homo sapiens

<400> SEQUENCE: 62

Lys Ala Thr
1

<210> SEQ ID NO 63
<211> LENGTH: 4
<212> TYPE: PRT
<213> ORGANISM: Homo sapiens

<400> SEQUENCE: 63

Arg Ser Ala Ser
1

<210> SEQ ID NO 64
<211> LENGTH: 3
<212> TYPE: PRT
<213> ORGANISM: Homo sapiens

<400> SEQUENCE: 64

Lys Ser Ser
1

<210> SEQ ID NO 65
<211> LENGTH: 5
<212> TYPE: PRT
<213> ORGANISM: Homo sapiens

<400> SEQUENCE: 65

Arg Ser Ser Ser Ser
1               5

<210> SEQ ID NO 66
<211> LENGTH: 5
<212> TYPE: PRT
<213> ORGANISM: Homo sapiens

<400> SEQUENCE: 66

His Arg Ser Gly Thr
1               5

<210> SEQ ID NO 67
<211> LENGTH: 5
<212> TYPE: PRT
<213> ORGANISM: Homo sapiens

<400> SEQUENCE: 67

Arg Gly Leu Ser Arg
1               5

<210> SEQ ID NO 68
<211> LENGTH: 4
<212> TYPE: PRT
<213> ORGANISM: Homo sapiens

<400> SEQUENCE: 68

Arg Gln Glu Thr
1

<210> SEQ ID NO 69
<211> LENGTH: 3
<212> TYPE: PRT
<213> ORGANISM: Homo sapiens

<400> SEQUENCE: 69

Arg Asp Ser
1

<210> SEQ ID NO 70
<211> LENGTH: 4
<212> TYPE: PRT
<213> ORGANISM: Homo sapiens

<400> SEQUENCE: 70

His Gly Ser Ser
1

<210> SEQ ID NO 71
<211> LENGTH: 7
<212> TYPE: PRT
<213> ORGANISM: Homo sapiens

<400> SEQUENCE: 71

Arg Glu Ser Arg His Arg Ser
1               5

<210> SEQ ID NO 72
<211> LENGTH: 4
<212> TYPE: PRT
<213> ORGANISM: Homo sapiens

<400> SEQUENCE: 72

Lys Gln Arg Ser
1

```
<210> SEQ ID NO 73
<211> LENGTH: 4
<212> TYPE: PRT
<213> ORGANISM: Homo sapiens

<400> SEQUENCE: 73

Arg His Lys Ser
1

<210> SEQ ID NO 74
<211> LENGTH: 5
<212> TYPE: PRT
<213> ORGANISM: Artificial Sequence
<220> FEATURE:
<223> OTHER INFORMATION: mutant

<400> SEQUENCE: 74

Arg Pro Ala Asp Ala
1               5

<210> SEQ ID NO 75
<211> LENGTH: 4
<212> TYPE: PRT
<213> ORGANISM: Artificial Sequence
<220> FEATURE:
<223> OTHER INFORMATION: mutant

<400> SEQUENCE: 75

Lys Ala Lys Ala
1

<210> SEQ ID NO 76
<211> LENGTH: 5
<212> TYPE: PRT
<213> ORGANISM: Artificial Sequence
<220> FEATURE:
<223> OTHER INFORMATION: mutant

<400> SEQUENCE: 76

Lys Phe Tyr Ala Ala
1               5

<210> SEQ ID NO 77
<211> LENGTH: 6
<212> TYPE: PRT
<213> ORGANISM: Artificial Sequence
<220> FEATURE:
<223> OTHER INFORMATION: mutant

<400> SEQUENCE: 77

Lys Ala Gly Gly Asn Ala
1               5

<210> SEQ ID NO 78
<211> LENGTH: 4
<212> TYPE: PRT
<213> ORGANISM: Artificial Sequence
<220> FEATURE:
<223> OTHER INFORMATION: mutant

<400> SEQUENCE: 78

Arg Lys Ala Ala
1

<210> SEQ ID NO 79
<211> LENGTH: 3
<212> TYPE: PRT
```

```
<213> ORGANISM: Artificial Sequence
<220> FEATURE:
<223> OTHER INFORMATION: mutant

<400> SEQUENCE: 79

Lys Pro Ala
1

<210> SEQ ID NO 80
<211> LENGTH: 3
<212> TYPE: PRT
<213> ORGANISM: Artificial Sequence
<220> FEATURE:
<223> OTHER INFORMATION: mutant

<400> SEQUENCE: 80

Lys Lys Ala
1

<210> SEQ ID NO 81
<211> LENGTH: 3
<212> TYPE: PRT
<213> ORGANISM: Artificial Sequence
<220> FEATURE:
<223> OTHER INFORMATION: mutant

<400> SEQUENCE: 81

Arg Ile Ala
1

<210> SEQ ID NO 82
<211> LENGTH: 3
<212> TYPE: PRT
<213> ORGANISM: Artificial Sequence
<220> FEATURE:
<223> OTHER INFORMATION: mutant

<400> SEQUENCE: 82

Arg Val Ala
1

<210> SEQ ID NO 83
<211> LENGTH: 3
<212> TYPE: PRT
<213> ORGANISM: Artificial Sequence
<220> FEATURE:
<223> OTHER INFORMATION: mutant

<400> SEQUENCE: 83

Lys Arg Ala
1

<210> SEQ ID NO 84
<211> LENGTH: 4
<212> TYPE: PRT
<213> ORGANISM: Artificial Sequence
<220> FEATURE:
<223> OTHER INFORMATION: mutant

<400> SEQUENCE: 84

Arg Ala Asn Ala
1

<210> SEQ ID NO 85
<211> LENGTH: 3
<212> TYPE: PRT
<213> ORGANISM: Artificial Sequence
```

```
<220> FEATURE:
<223> OTHER INFORMATION: mutant

<400> SEQUENCE: 85

Arg Ala Ala
1

<210> SEQ ID NO 86
<211> LENGTH: 3
<212> TYPE: PRT
<213> ORGANISM: Artificial Sequence
<220> FEATURE:
<223> OTHER INFORMATION: mutant

<400> SEQUENCE: 86

Lys Ala Ala
1

<210> SEQ ID NO 87
<211> LENGTH: 4
<212> TYPE: PRT
<213> ORGANISM: Artificial Sequence
<220> FEATURE:
<223> OTHER INFORMATION: mutant

<400> SEQUENCE: 87

Lys Ile Ala Ala
1

<210> SEQ ID NO 88
<211> LENGTH: 4
<212> TYPE: PRT
<213> ORGANISM: Artificial Sequence
<220> FEATURE:
<223> OTHER INFORMATION: mutant

<400> SEQUENCE: 88

Arg Gly Lys Ala
1

<210> SEQ ID NO 89
<211> LENGTH: 3
<212> TYPE: PRT
<213> ORGANISM: Artificial Sequence
<220> FEATURE:
<223> OTHER INFORMATION: mutant

<400> SEQUENCE: 89

Lys Ala Ala
1

<210> SEQ ID NO 90
<211> LENGTH: 5
<212> TYPE: PRT
<213> ORGANISM: Artificial Sequence
<220> FEATURE:
<223> OTHER INFORMATION: mutant

<400> SEQUENCE: 90

Arg Pro Ala Asp Ala
1               5

<210> SEQ ID NO 91
<211> LENGTH: 4
<212> TYPE: PRT
<213> ORGANISM: Artificial Sequence
<220> FEATURE:
```

<223> OTHER INFORMATION: mutant

<400> SEQUENCE: 91

Lys Ala Lys Ala
1

<210> SEQ ID NO 92
<211> LENGTH: 5
<212> TYPE: PRT
<213> ORGANISM: Artificial Sequence
<220> FEATURE:
<223> OTHER INFORMATION: mutant

<400> SEQUENCE: 92

Lys Phe Tyr Ala Ala
1               5

<210> SEQ ID NO 93
<211> LENGTH: 6
<212> TYPE: PRT
<213> ORGANISM: Artificial Sequence
<220> FEATURE:
<223> OTHER INFORMATION: mutant

<400> SEQUENCE: 93

Lys Ala Gly Gly Asn Ala
1               5

<210> SEQ ID NO 94
<211> LENGTH: 4
<212> TYPE: PRT
<213> ORGANISM: Artificial Sequence
<220> FEATURE:
<223> OTHER INFORMATION: mutant

<400> SEQUENCE: 94

Arg Lys Ala Ala
1

<210> SEQ ID NO 95
<211> LENGTH: 3
<212> TYPE: PRT
<213> ORGANISM: Artificial Sequence
<220> FEATURE:
<223> OTHER INFORMATION: mutant

<400> SEQUENCE: 95

Lys Pro Ala
1

<210> SEQ ID NO 96
<211> LENGTH: 3
<212> TYPE: PRT
<213> ORGANISM: Artificial Sequence
<220> FEATURE:
<223> OTHER INFORMATION: mutant

<400> SEQUENCE: 96

Lys Lys Ala
1

<210> SEQ ID NO 97
<211> LENGTH: 3
<212> TYPE: PRT
<213> ORGANISM: Artificial Sequence
<220> FEATURE:
<223> OTHER INFORMATION: mutant

```
<400> SEQUENCE: 97

Arg Ile Ala
1

<210> SEQ ID NO 98
<211> LENGTH: 3
<212> TYPE: PRT
<213> ORGANISM: Artificial Sequence
<220> FEATURE:
<223> OTHER INFORMATION: mutant

<400> SEQUENCE: 98

Arg Val Ala
1

<210> SEQ ID NO 99
<211> LENGTH: 3
<212> TYPE: PRT
<213> ORGANISM: Artificial Sequence
<220> FEATURE:
<223> OTHER INFORMATION: mutant

<400> SEQUENCE: 99

Lys Arg Ala
1

<210> SEQ ID NO 100
<211> LENGTH: 4
<212> TYPE: PRT
<213> ORGANISM: Artificial Sequence
<220> FEATURE:
<223> OTHER INFORMATION: mutant

<400> SEQUENCE: 100

Arg Ala Asn Ala
1

<210> SEQ ID NO 101
<211> LENGTH: 3
<212> TYPE: PRT
<213> ORGANISM: Artificial Sequence
<220> FEATURE:
<223> OTHER INFORMATION: mutant

<400> SEQUENCE: 101

Arg Ala Ala
1

<210> SEQ ID NO 102
<211> LENGTH: 3
<212> TYPE: PRT
<213> ORGANISM: Artificial Sequence
<220> FEATURE:
<223> OTHER INFORMATION: mutant

<400> SEQUENCE: 102

Lys Ala Ala
1

<210> SEQ ID NO 103
<211> LENGTH: 4
<212> TYPE: PRT
<213> ORGANISM: Artificial Sequence
<220> FEATURE:
<223> OTHER INFORMATION: mutant
```

```
<400> SEQUENCE: 103

Lys Ile Ala Ala
1

<210> SEQ ID NO 104
<211> LENGTH: 4
<212> TYPE: PRT
<213> ORGANISM: Artificial Sequence
<220> FEATURE:
<223> OTHER INFORMATION: mutant

<400> SEQUENCE: 104

Arg Gly Lys Ala
1

<210> SEQ ID NO 105
<211> LENGTH: 3
<212> TYPE: PRT
<213> ORGANISM: Artificial Sequence
<220> FEATURE:
<223> OTHER INFORMATION: mutant

<400> SEQUENCE: 105

Lys Ala Ala
1

<210> SEQ ID NO 106
<211> LENGTH: 4
<212> TYPE: PRT
<213> ORGANISM: Artificial Sequence
<220> FEATURE:
<223> OTHER INFORMATION: mutant

<400> SEQUENCE: 106

Arg Ala Ala Ala
1

<210> SEQ ID NO 107
<211> LENGTH: 3
<212> TYPE: PRT
<213> ORGANISM: Artificial Sequence
<220> FEATURE:
<223> OTHER INFORMATION: mutant

<400> SEQUENCE: 107

Lys Ala Ala
1

<210> SEQ ID NO 108
<211> LENGTH: 5
<212> TYPE: PRT
<213> ORGANISM: Artificial Sequence
<220> FEATURE:
<223> OTHER INFORMATION: mutant

<400> SEQUENCE: 108

Arg Ala Ala Ala Ala
1               5

<210> SEQ ID NO 109
<211> LENGTH: 5
<212> TYPE: PRT
<213> ORGANISM: Artificial Sequence
<220> FEATURE:
<223> OTHER INFORMATION: mutant

<400> SEQUENCE: 109
```

His Arg Ala Gly Ala
1               5

<210> SEQ ID NO 110
<211> LENGTH: 4
<212> TYPE: PRT
<213> ORGANISM: Artificial Sequence
<220> FEATURE:
<223> OTHER INFORMATION: mutant

<400> SEQUENCE: 110

Arg Gln Glu Ala
1

<210> SEQ ID NO 111
<211> LENGTH: 3
<212> TYPE: PRT
<213> ORGANISM: Artificial Sequence
<220> FEATURE:
<223> OTHER INFORMATION: mutant

<400> SEQUENCE: 111

Arg Asp Ala
1

<210> SEQ ID NO 112
<211> LENGTH: 4
<212> TYPE: PRT
<213> ORGANISM: Artificial Sequence
<220> FEATURE:
<223> OTHER INFORMATION: mutant

<400> SEQUENCE: 112

His Gly Ala Ala
1

<210> SEQ ID NO 113
<211> LENGTH: 7
<212> TYPE: PRT
<213> ORGANISM: Artificial Sequence
<220> FEATURE:
<223> OTHER INFORMATION: mutant

<400> SEQUENCE: 113

Arg Glu Ala Arg His Arg Ala
1               5

<210> SEQ ID NO 114
<211> LENGTH: 4
<212> TYPE: PRT
<213> ORGANISM: Artificial Sequence
<220> FEATURE:
<223> OTHER INFORMATION: mutant

<400> SEQUENCE: 114

Lys Gln Arg Ala
1

<210> SEQ ID NO 115
<211> LENGTH: 4
<212> TYPE: PRT
<213> ORGANISM: Artificial Sequence
<220> FEATURE:
<223> OTHER INFORMATION: mutant

<400> SEQUENCE: 115

```
Arg His Lys Ala
1

<210> SEQ ID NO 116
<211> LENGTH: 3
<212> TYPE: PRT
<213> ORGANISM: Lepus americanus

<400> SEQUENCE: 116

His Leu Ser
1

<210> SEQ ID NO 117
<211> LENGTH: 3
<212> TYPE: PRT
<213> ORGANISM: Lepus americanus

<400> SEQUENCE: 117

Lys Gly Thr
1

<210> SEQ ID NO 118
<211> LENGTH: 5
<212> TYPE: PRT
<213> ORGANISM: Lepus americanus

<400> SEQUENCE: 118

Lys Leu Met Gly Ser
1               5

<210> SEQ ID NO 119
<211> LENGTH: 7
<212> TYPE: PRT
<213> ORGANISM: Lepus americanus

<400> SEQUENCE: 119

Lys Lys Gln Gly Ser Thr Thr
1               5

<210> SEQ ID NO 120
<211> LENGTH: 6
<212> TYPE: PRT
<213> ORGANISM: Lepus americanus

<400> SEQUENCE: 120

Arg Arg Ala Cys Ile Ser
1               5

<210> SEQ ID NO 121
<211> LENGTH: 4
<212> TYPE: PRT
<213> ORGANISM: Lepus americanus

<400> SEQUENCE: 121

Arg Asn Met Ser
1

<210> SEQ ID NO 122
<211> LENGTH: 8
<212> TYPE: PRT
<213> ORGANISM: Lepus americanus

<400> SEQUENCE: 122

Arg Ile Ser Lys Ser Lys Phe Ser
1               5
```

```
<210> SEQ ID NO 123
<211> LENGTH: 8
<212> TYPE: PRT
<213> ORGANISM: Lepus americanus

<400> SEQUENCE: 123

Lys Lys Leu Ala Arg Thr Ala Ser
1               5

<210> SEQ ID NO 124
<211> LENGTH: 4
<212> TYPE: PRT
<213> ORGANISM: Lepus americanus

<400> SEQUENCE: 124

Lys Ser Ile Thr
1

<210> SEQ ID NO 125
<211> LENGTH: 4
<212> TYPE: PRT
<213> ORGANISM: Lepus americanus

<400> SEQUENCE: 125

Arg Pro Leu Ser
1

<210> SEQ ID NO 126
<211> LENGTH: 3
<212> TYPE: PRT
<213> ORGANISM: Lepus americanus

<400> SEQUENCE: 126

Lys Gly Ser
1

<210> SEQ ID NO 127
<211> LENGTH: 4
<212> TYPE: PRT
<213> ORGANISM: Lepus americanus

<400> SEQUENCE: 127

Arg Asp Trp Ser
1

<210> SEQ ID NO 128
<211> LENGTH: 4
<212> TYPE: PRT
<213> ORGANISM: Lepus americanus

<400> SEQUENCE: 128

Arg Leu Val Ser
1

<210> SEQ ID NO 129
<211> LENGTH: 4
<212> TYPE: PRT
<213> ORGANISM: Lepus americanus

<400> SEQUENCE: 129

Arg Ile Lys Thr
1
```

```
<210> SEQ ID NO 130
<211> LENGTH: 4
<212> TYPE: PRT
<213> ORGANISM: Lepus americanus

<400> SEQUENCE: 130

Lys Arg Thr Ser
1

<210> SEQ ID NO 131
<211> LENGTH: 3
<212> TYPE: PRT
<213> ORGANISM: Lepus americanus

<400> SEQUENCE: 131

Lys Pro Ser
1

<210> SEQ ID NO 132
<211> LENGTH: 5
<212> TYPE: PRT
<213> ORGANISM: Lepus americanus

<400> SEQUENCE: 132

Arg Asn Ala Leu Ser
1               5

<210> SEQ ID NO 133
<211> LENGTH: 9
<212> TYPE: PRT
<213> ORGANISM: Lepus americanus

<400> SEQUENCE: 133

Arg Arg Ala Ile Ser Gly Asp Leu Thr
1               5

<210> SEQ ID NO 134
<211> LENGTH: 5
<212> TYPE: PRT
<213> ORGANISM: Lepus americanus

<400> SEQUENCE: 134

Lys Glu Ala Val Ser
1               5

<210> SEQ ID NO 135
<211> LENGTH: 3
<212> TYPE: PRT
<213> ORGANISM: Lepus americanus

<400> SEQUENCE: 135

His Val Ser
1

<210> SEQ ID NO 136
<211> LENGTH: 3
<212> TYPE: PRT
<213> ORGANISM: Lepus americanus

<400> SEQUENCE: 136

His Ile Ser
1

<210> SEQ ID NO 137
<211> LENGTH: 6
```

```
<212> TYPE: PRT
<213> ORGANISM: Lepus americanus

<400> SEQUENCE: 137

Lys Leu Val Asp Ser Thr
1               5

<210> SEQ ID NO 138
<211> LENGTH: 3
<212> TYPE: PRT
<213> ORGANISM: Lepus americanus

<400> SEQUENCE: 138

His Gly Ser
1

<210> SEQ ID NO 139
<211> LENGTH: 4
<212> TYPE: PRT
<213> ORGANISM: Lepus americanus

<400> SEQUENCE: 139

Lys Leu Ser Ser
1

<210> SEQ ID NO 140
<211> LENGTH: 5
<212> TYPE: PRT
<213> ORGANISM: Lepus americanus

<400> SEQUENCE: 140

Lys Arg Cys His Ser
1               5

<210> SEQ ID NO 141
<211> LENGTH: 3
<212> TYPE: PRT
<213> ORGANISM: Lepus americanus

<400> SEQUENCE: 141

Arg Leu Ser
1

<210> SEQ ID NO 142
<211> LENGTH: 4
<212> TYPE: PRT
<213> ORGANISM: Lepus americanus

<400> SEQUENCE: 142

Arg Ser Ala Ser
1

<210> SEQ ID NO 143
<211> LENGTH: 4
<212> TYPE: PRT
<213> ORGANISM: Lepus americanus

<400> SEQUENCE: 143

Arg Arg Ala Ser
1

<210> SEQ ID NO 144
<211> LENGTH: 7
<212> TYPE: PRT
<213> ORGANISM: Lepus americanus
```

```
<400> SEQUENCE: 144

Arg Ser His Ser Pro Thr Ser
1               5

<210> SEQ ID NO 145
<211> LENGTH: 5
<212> TYPE: PRT
<213> ORGANISM: Lepus americanus

<400> SEQUENCE: 145

Lys Leu Asn Ser Ser
1               5

<210> SEQ ID NO 146
<211> LENGTH: 4
<212> TYPE: PRT
<213> ORGANISM: Lepus americanus

<400> SEQUENCE: 146

His Cys Gly Ser
1

<210> SEQ ID NO 147
<211> LENGTH: 5
<212> TYPE: PRT
<213> ORGANISM: Lepus americanus

<400> SEQUENCE: 147

Arg Gly Asp Ser Ser
1               5

<210> SEQ ID NO 148
<211> LENGTH: 6
<212> TYPE: PRT
<213> ORGANISM: Lepus americanus

<400> SEQUENCE: 148

Arg Pro Val Ser Leu Thr
1               5

<210> SEQ ID NO 149
<211> LENGTH: 4
<212> TYPE: PRT
<213> ORGANISM: Lepus americanus

<400> SEQUENCE: 149

Phe His Gly Ser
1

<210> SEQ ID NO 150
<211> LENGTH: 3
<212> TYPE: PRT
<213> ORGANISM: Lepus americanus

<400> SEQUENCE: 150

Arg Gln Ser
1

<210> SEQ ID NO 151
<211> LENGTH: 4
<212> TYPE: PRT
<213> ORGANISM: Artificial Sequence
<220> FEATURE:
<223> OTHER INFORMATION: mutant
```

```
<400> SEQUENCE: 151

Arg Asn Met Ala
1

<210> SEQ ID NO 152
<211> LENGTH: 8
<212> TYPE: PRT
<213> ORGANISM: Artificial Sequence
<220> FEATURE:
<223> OTHER INFORMATION: mutant

<400> SEQUENCE: 152

Arg Ile Ala Lys Ala Lys Phe Ala
1               5

<210> SEQ ID NO 153
<211> LENGTH: 8
<212> TYPE: PRT
<213> ORGANISM: Artificial Sequence
<220> FEATURE:
<223> OTHER INFORMATION: mutant

<400> SEQUENCE: 153

Lys Lys Leu Ala Arg Ala Ala Ala
1               5

<210> SEQ ID NO 154
<211> LENGTH: 4
<212> TYPE: PRT
<213> ORGANISM: Artificial Sequence
<220> FEATURE:
<223> OTHER INFORMATION: mutant

<400> SEQUENCE: 154

Lys Ser Ile Ala
1

<210> SEQ ID NO 155
<211> LENGTH: 4
<212> TYPE: PRT
<213> ORGANISM: Artificial Sequence
<220> FEATURE:
<223> OTHER INFORMATION: mutant

<400> SEQUENCE: 155

Arg Pro Leu Ala
1

<210> SEQ ID NO 156
<211> LENGTH: 3
<212> TYPE: PRT
<213> ORGANISM: Artificial Sequence
<220> FEATURE:
<223> OTHER INFORMATION: mutant

<400> SEQUENCE: 156

Lys Gly Ala
1

<210> SEQ ID NO 157
<211> LENGTH: 4
<212> TYPE: PRT
<213> ORGANISM: Artificial Sequence
<220> FEATURE:
<223> OTHER INFORMATION: mutant
```

<400> SEQUENCE: 157

Arg Asp Trp Ala
1

<210> SEQ ID NO 158
<211> LENGTH: 4
<212> TYPE: PRT
<213> ORGANISM: Artificial Sequence
<220> FEATURE:
<223> OTHER INFORMATION: mutant

<400> SEQUENCE: 158

Arg Leu Val Ala
1

<210> SEQ ID NO 159
<211> LENGTH: 4
<212> TYPE: PRT
<213> ORGANISM: Artificial Sequence
<220> FEATURE:
<223> OTHER INFORMATION: mutant

<400> SEQUENCE: 159

Arg Ile Lys Ala
1

<210> SEQ ID NO 160
<211> LENGTH: 4
<212> TYPE: PRT
<213> ORGANISM: Artificial Sequence
<220> FEATURE:
<223> OTHER INFORMATION: mutant

<400> SEQUENCE: 160

Lys Arg Ala Ala
1

<210> SEQ ID NO 161
<211> LENGTH: 3
<212> TYPE: PRT
<213> ORGANISM: Artificial Sequence
<220> FEATURE:
<223> OTHER INFORMATION: mutant

<400> SEQUENCE: 161

Lys Pro Ala
1

<210> SEQ ID NO 162
<211> LENGTH: 9
<212> TYPE: PRT
<213> ORGANISM: Artificial Sequence
<220> FEATURE:
<223> OTHER INFORMATION: mutant

<400> SEQUENCE: 162

Arg Arg Ala Ile Ala Gly Asp Leu Ala
1               5

<210> SEQ ID NO 163
<211> LENGTH: 3
<212> TYPE: PRT
<213> ORGANISM: Artificial Sequence
<220> FEATURE:
<223> OTHER INFORMATION: mutant

<400> SEQUENCE: 163

```
His Val Ala
1

<210> SEQ ID NO 164
<211> LENGTH: 5
<212> TYPE: PRT
<213> ORGANISM: Artificial Sequence
<220> FEATURE:
<223> OTHER INFORMATION: mutant

<400> SEQUENCE: 164

Lys Arg Cys His Ala
1               5

<210> SEQ ID NO 165
<211> LENGTH: 4
<212> TYPE: PRT
<213> ORGANISM: Artificial Sequence
<220> FEATURE:
<223> OTHER INFORMATION: mutant

<400> SEQUENCE: 165

Arg Ala Ala Ala
1

<210> SEQ ID NO 166
<211> LENGTH: 4
<212> TYPE: PRT
<213> ORGANISM: Artificial Sequence
<220> FEATURE:
<223> OTHER INFORMATION: mutant

<400> SEQUENCE: 166

Arg Arg Ala Ala
1

<210> SEQ ID NO 167
<211> LENGTH: 7
<212> TYPE: PRT
<213> ORGANISM: Artificial Sequence
<220> FEATURE:
<223> OTHER INFORMATION: mutant

<400> SEQUENCE: 167

Arg Ala His Ala Pro Ala Ala
1               5

<210> SEQ ID NO 168
<211> LENGTH: 5
<212> TYPE: PRT
<213> ORGANISM: Artificial Sequence
<220> FEATURE:
<223> OTHER INFORMATION: mutant

<400> SEQUENCE: 168

Lys Leu Asn Ala Ala
1               5

<210> SEQ ID NO 169
<211> LENGTH: 4
<212> TYPE: PRT
<213> ORGANISM: Artificial Sequence
<220> FEATURE:
<223> OTHER INFORMATION: mutant

<400> SEQUENCE: 169
```

His Cys Gly Ala
1

<210> SEQ ID NO 170
<211> LENGTH: 6
<212> TYPE: PRT
<213> ORGANISM: Artificial Sequence
<220> FEATURE:
<223> OTHER INFORMATION: mutant

<400> SEQUENCE: 170

Arg Pro Val Ala Leu Ala
1               5

<210> SEQ ID NO 171
<211> LENGTH: 4
<212> TYPE: PRT
<213> ORGANISM: Artificial Sequence
<220> FEATURE:
<223> OTHER INFORMATION: mutant

<400> SEQUENCE: 171

Phe His Gly Ala
1

<210> SEQ ID NO 172
<211> LENGTH: 3
<212> TYPE: PRT
<213> ORGANISM: Artificial Sequence
<220> FEATURE:
<223> OTHER INFORMATION: mutant

<400> SEQUENCE: 172

His Leu Ala
1

<210> SEQ ID NO 173
<211> LENGTH: 3
<212> TYPE: PRT
<213> ORGANISM: Artificial Sequence
<220> FEATURE:
<223> OTHER INFORMATION: mutant

<400> SEQUENCE: 173

Lys Gly Ala
1

<210> SEQ ID NO 174
<211> LENGTH: 5
<212> TYPE: PRT
<213> ORGANISM: Artificial Sequence
<220> FEATURE:
<223> OTHER INFORMATION: mutant

<400> SEQUENCE: 174

Lys Leu Met Gly Ala
1               5

<210> SEQ ID NO 175
<211> LENGTH: 7
<212> TYPE: PRT
<213> ORGANISM: Artificial Sequence
<220> FEATURE:
<223> OTHER INFORMATION: mutant

<400> SEQUENCE: 175

Lys Lys Gln Gly Ala Ala Ala

```
1               5

<210> SEQ ID NO 176
<211> LENGTH: 6
<212> TYPE: PRT
<213> ORGANISM: Artificial Sequence
<220> FEATURE:
<223> OTHER INFORMATION: mutant

<400> SEQUENCE: 176

Arg Arg Ala Cys Ile Ala
1               5

<210> SEQ ID NO 177
<211> LENGTH: 4
<212> TYPE: PRT
<213> ORGANISM: Artificial Sequence
<220> FEATURE:
<223> OTHER INFORMATION: mutant

<400> SEQUENCE: 177

Arg Asn Met Ala
1

<210> SEQ ID NO 178
<211> LENGTH: 8
<212> TYPE: PRT
<213> ORGANISM: Artificial Sequence
<220> FEATURE:
<223> OTHER INFORMATION: mutant

<400> SEQUENCE: 178

Arg Ile Ala Lys Ala Lys Phe Ala
1               5

<210> SEQ ID NO 179
<211> LENGTH: 8
<212> TYPE: PRT
<213> ORGANISM: Artificial Sequence
<220> FEATURE:
<223> OTHER INFORMATION: mutant

<400> SEQUENCE: 179

Lys Lys Leu Ala Arg Ala Ala Ala
1               5

<210> SEQ ID NO 180
<211> LENGTH: 4
<212> TYPE: PRT
<213> ORGANISM: Artificial Sequence
<220> FEATURE:
<223> OTHER INFORMATION: mutant

<400> SEQUENCE: 180

Lys Ser Ile Ala
1

<210> SEQ ID NO 181
<211> LENGTH: 4
<212> TYPE: PRT
<213> ORGANISM: Artificial Sequence
<220> FEATURE:
<223> OTHER INFORMATION: mutant

<400> SEQUENCE: 181

Arg Pro Leu Ala
1
```

```
<210> SEQ ID NO 182
<211> LENGTH: 3
<212> TYPE: PRT
<213> ORGANISM: Artificial Sequence
<220> FEATURE:
<223> OTHER INFORMATION: mutant

<400> SEQUENCE: 182

Lys Gly Ala
1

<210> SEQ ID NO 183
<211> LENGTH: 4
<212> TYPE: PRT
<213> ORGANISM: Artificial Sequence
<220> FEATURE:
<223> OTHER INFORMATION: mutant

<400> SEQUENCE: 183

Arg Asp Trp Ala
1

<210> SEQ ID NO 184
<211> LENGTH: 4
<212> TYPE: PRT
<213> ORGANISM: Artificial Sequence
<220> FEATURE:
<223> OTHER INFORMATION: mutant

<400> SEQUENCE: 184

Arg Leu Val Ala
1

<210> SEQ ID NO 185
<211> LENGTH: 4
<212> TYPE: PRT
<213> ORGANISM: Artificial Sequence
<220> FEATURE:
<223> OTHER INFORMATION: mutant

<400> SEQUENCE: 185

Arg Ile Lys Ala
1

<210> SEQ ID NO 186
<211> LENGTH: 4
<212> TYPE: PRT
<213> ORGANISM: Artificial Sequence
<220> FEATURE:
<223> OTHER INFORMATION: mutant

<400> SEQUENCE: 186

Lys Arg Ala Ala
1

<210> SEQ ID NO 187
<211> LENGTH: 3
<212> TYPE: PRT
<213> ORGANISM: Artificial Sequence
<220> FEATURE:
<223> OTHER INFORMATION: mutant

<400> SEQUENCE: 187

Lys Pro Ala
1
```

<210> SEQ ID NO 188
<211> LENGTH: 5
<212> TYPE: PRT
<213> ORGANISM: Artificial Sequence
<220> FEATURE:
<223> OTHER INFORMATION: mutant

<400> SEQUENCE: 188

Arg Asn Ala Leu Ala
1               5

<210> SEQ ID NO 189
<211> LENGTH: 9
<212> TYPE: PRT
<213> ORGANISM: Artificial Sequence
<220> FEATURE:
<223> OTHER INFORMATION: mutant

<400> SEQUENCE: 189

Arg Arg Ala Ile Ala Gly Asp Leu Ala
1               5

<210> SEQ ID NO 190
<211> LENGTH: 5
<212> TYPE: PRT
<213> ORGANISM: Artificial Sequence
<220> FEATURE:
<223> OTHER INFORMATION: mutant

<400> SEQUENCE: 190

Lys Glu Ala Val Ala
1               5

<210> SEQ ID NO 191
<211> LENGTH: 3
<212> TYPE: PRT
<213> ORGANISM: Artificial Sequence
<220> FEATURE:
<223> OTHER INFORMATION: mutant

<400> SEQUENCE: 191

His Val Ala
1

<210> SEQ ID NO 192
<211> LENGTH: 3
<212> TYPE: PRT
<213> ORGANISM: Artificial Sequence
<220> FEATURE:
<223> OTHER INFORMATION: mutant

<400> SEQUENCE: 192

His Ile Ala
1

<210> SEQ ID NO 193
<211> LENGTH: 6
<212> TYPE: PRT
<213> ORGANISM: Artificial Sequence
<220> FEATURE:
<223> OTHER INFORMATION: mutant

<400> SEQUENCE: 193

Lys Leu Val Asp Ala Ala
1               5

```
<210> SEQ ID NO 194
<211> LENGTH: 3
<212> TYPE: PRT
<213> ORGANISM: Artificial Sequence
<220> FEATURE:
<223> OTHER INFORMATION: mutant

<400> SEQUENCE: 194

His Gly Ala
1

<210> SEQ ID NO 195
<211> LENGTH: 4
<212> TYPE: PRT
<213> ORGANISM: Artificial Sequence
<220> FEATURE:
<223> OTHER INFORMATION: mutant

<400> SEQUENCE: 195

Lys Leu Ser Ala
1

<210> SEQ ID NO 196
<211> LENGTH: 5
<212> TYPE: PRT
<213> ORGANISM: Artificial Sequence
<220> FEATURE:
<223> OTHER INFORMATION: mutant

<400> SEQUENCE: 196

Lys Arg Cys His Ala
1               5

<210> SEQ ID NO 197
<211> LENGTH: 3
<212> TYPE: PRT
<213> ORGANISM: Artificial Sequence
<220> FEATURE:
<223> OTHER INFORMATION: mutant

<400> SEQUENCE: 197

Arg Leu Ala
1

<210> SEQ ID NO 198
<211> LENGTH: 4
<212> TYPE: PRT
<213> ORGANISM: Artificial Sequence
<220> FEATURE:
<223> OTHER INFORMATION: mutant

<400> SEQUENCE: 198

Arg Ala Ala Ala
1

<210> SEQ ID NO 199
<211> LENGTH: 4
<212> TYPE: PRT
<213> ORGANISM: Artificial Sequence
<220> FEATURE:
<223> OTHER INFORMATION: mutant

<400> SEQUENCE: 199

Arg Arg Ala Ala
1

<210> SEQ ID NO 200
```

```
<211> LENGTH: 7
<212> TYPE: PRT
<213> ORGANISM: Artificial Sequence
<220> FEATURE:
<223> OTHER INFORMATION: mutant

<400> SEQUENCE: 200

Arg Ala His Ala Pro Ala Ala
1               5

<210> SEQ ID NO 201
<211> LENGTH: 5
<212> TYPE: PRT
<213> ORGANISM: Artificial Sequence
<220> FEATURE:
<223> OTHER INFORMATION: mutant

<400> SEQUENCE: 201

Lys Leu Asn Ala Ala
1               5

<210> SEQ ID NO 202
<211> LENGTH: 4
<212> TYPE: PRT
<213> ORGANISM: Artificial Sequence
<220> FEATURE:
<223> OTHER INFORMATION: mutant

<400> SEQUENCE: 202

His Cys Gly Ala
1

<210> SEQ ID NO 203
<211> LENGTH: 5
<212> TYPE: PRT
<213> ORGANISM: Artificial Sequence
<220> FEATURE:
<223> OTHER INFORMATION: mutant

<400> SEQUENCE: 203

Arg Gly Asp Ala Ser
1               5

<210> SEQ ID NO 204
<211> LENGTH: 6
<212> TYPE: PRT
<213> ORGANISM: Artificial Sequence
<220> FEATURE:
<223> OTHER INFORMATION: mutant

<400> SEQUENCE: 204

Arg Pro Val Ala Leu Ala
1               5

<210> SEQ ID NO 205
<211> LENGTH: 4
<212> TYPE: PRT
<213> ORGANISM: Artificial Sequence
<220> FEATURE:
<223> OTHER INFORMATION: mutant

<400> SEQUENCE: 205

Phe His Gly Ala
1

<210> SEQ ID NO 206
<211> LENGTH: 3
```

```
<212> TYPE: PRT
<213> ORGANISM: Artificial Sequence
<220> FEATURE:
<223> OTHER INFORMATION: mutant

<400> SEQUENCE: 206

Arg Gln Ala
1

<210> SEQ ID NO 207
<211> LENGTH: 15
<212> TYPE: DNA
<213> ORGANISM: Artificial Sequence
<220> FEATURE:
<223> OTHER INFORMATION: mutant

<400> SEQUENCE: 207
tacctggact ggatc                                                    15

<210> SEQ ID NO 208
<211> LENGTH: 15
<212> TYPE: DNA
<213> ORGANISM: Artificial Sequence
<220> FEATURE:
<223> OTHER INFORMATION: mutant

<400> SEQUENCE: 208
gctctggacg cagct                                                    15
```

DRUG TARGET FOR PREVENTING PATHOLOGIC CALCIUM OVERLOAD IN CARDIOMYOCYTES AND METHODS OF SCREENING FOR SAME

CROSS-REFERENCE TO RELATED APPLICATIONS

The present application is a U.S. Non-provisional patent application, which claims priority to U.S. Provisional Patent Application No. 62/609,934, filed on Dec. 22, 2017. The entire content of the aforementioned application is incorporated by reference as if recited in full herein.

GOVERNMENT FUNDING

This invention was made with government support under HL121253 awarded by the National Institutes of Health. The government has certain rights in the invention.

INCORPORATION BY REFERENCE OF SEQUENCE LISTING

This application contains references to amino acids and/or nucleic acid sequences that have been filed concurrently herewith as sequence listing text file "2399285-seq.txt", file size of 26.9 KB, created on Apr. 26, 2019. The aforementioned sequence listing is hereby incorporated by reference in its entirety pursuant to 37 C.F.R. § 1.52(e)(5).

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

The strength of cardiac contraction (contractility) is regulated by the concentration of calcium within the cytosplasm of cardiac muscle cells (cardiomyocytes). During systole (cardiac contraction), calcium enters the cytosol from the extracellular space through voltage-gated L-type calcium channels (CaV1.2) as well from intrinsic calcium storage compartments (the sarcoplasmic reticulum), through ryanodine receptor calcium channels (RyR2). As cytosolic calcium levels rapidly rise the calcium binds to the contractile apparatus, enabling the cell to contract. The calcium is then removed from the cytosol and the cell relaxes. Activation of the beta-adrenergic receptor cascade during exercise and stress causes more calcium to enter the cell through CaV1.2, resulting in increased contractility and improved cardiac output (FIG. 1). However, in certain disease states, such as systolic heart failure, structural heart disease, atrial arrhythmias, and catecholaminergic polymorphic ventricular tachycardia (CPVT), activation of the beta-adrenergic receptor system causes dysregulation of cytosolic calcium levels leading to clinical deterioration and death.

Beta-blockers are a ubiquitous class of medications that attenuate the effect of the beta-adrenergic receptor system on the heart and are first line treatment for these conditions. Unfortunately, beta-blockers have numerous off-target effects which limit their use and tolerability by patients. Novel agents that specifically block the effects of beta-adrenergic receptor activation on calcium levels in cardiomyocytes would have important therapeutic potential for many forms of heart disease.

In heart cells, $Ca^{2+}$ influx via $Ca_V1.2$ channels mediates excitation-contraction (E-C) coupling, controls action potential duration, and regulates gene expression. $Ca_V1.2$ channels are multi-subunit proteins composed minimally of a pore-forming $\alpha_{1C}$ and regulatory $\beta$ and $\alpha_2\delta$ subunits (Catterall 2000; Min et al. 2013; Peterson et al. 1999; Erickson et al. 2001). In adult ventricular cardiomyocytes, most $Ca_V1.2$ channels localize to transverse tubules where they lie in close proximity (~12 nm) and apposed to ryanodine receptors (RyR2) at dyadic junctions (Scriven et al. 2000). Dysregulation of $Ca_V1.2$ activity, surface density, or sub-cellular localization in cardiomyocytes can result in cardiac arrhythmias, heart failure, and sudden death.

Reconstitution experiments concluded that binding to $\beta$ subunits is indispensable for $\alpha_{1C}$ trafficking to the cell surface (Pere-Reyes et al. 1992; Castellano et al. 1993; Lacerda et al. 1991; Bichet et al. 2000; Chien et al. 1995; Brice et al. 1997; Dolphin 2003; Buraei and Yang 2010; Arikkath and Campbell 2003). The physiological relevance of this finding was initially supported by $\beta_2$ knockout mice, which were embryonic lethal, likely secondary to a decreased L-type $Ca^{2+}$ current (Weissgerber et al. 2006). An initial idea that $\beta$ binding to the $\alpha$-interaction domain (AID) of the $\alpha_1$-subunit I-II loop shielded an ER retention signal in the I-II loop to allow forward trafficking of the channel proved inadequate in subsequent experiments (Bichet et al. 2000; Altier et al. 2011; Fang and Colecraft 2011; Waithe et al. 2011). Surprisingly, cardiomyocyte-specific, conditional deletion of the Cacnb2 gene in adult mice reduced $\beta_2$ protein by 96% but caused only a modest 29% reduction in $Ca^{2+}$ current, with no obvious cardiac impairment (Meissner et al. 2011). Interpretation of this result is ambiguous, however, as it is complicated by the remnant (~4%) $\beta_2$ expression as well as the presence other $Ca_V\beta$ isoforms expressed in adult cardiomyocytes (Buraei and Yang 2010). Moreover, a contrasting viewpoint was provided by a study in which shRNA-mediated knockdown of $\beta_2$ in adult rat myocytes substantially diminished $Ca^{2+}$ current (Cingolani et al. 2007).

SUMMARY OF THE INVENTION

In the present disclosure, it is discovered that CaV1.2 must be bound to one of its subunits, CaVB ("beta-subunit"), in order for channel activity, cellular calcium influx, and cardiac contractility to increase following beta-adrenergic receptor activation. This invention describes the method of blocking the interaction of CaV1.2 and CaVB as a novel therapeutic approach for protecting cardiomyocytes from the deleterious effects of beta-adrenergic receptor activation on intracellular calcium handling in disease states. By preventing intracellular calcium dysfunction, this approach can have a major impact on the therapeutic management of millions of patients with heart disease.

CaVBs are obligatory for functional maturation of CaV1.2 channels, being necessary for targeting the channels to the plasma membrane, elevating channel open probability (Po), and modifying channel inactivation. Interaction between CaV1.2 and CaVB, also known as the "beta-subunit of CaV1.2" is dependent on two distinct mechanisms: (a) CaVBs bind to a conserved 18-residue sequence (the alpha interaction domain, or AID) on CaV1.2 (Kushnir A. et al. 2017; FIG. 2A), and (b) an intra-molecular interaction between src homology 3 (SH3) and guanylate kinase-like (GK) domains present within CaVBs (FIG. 2B). The functional significance of the AID site is demonstrated by the observation that mutations introduced within this region eliminate the effect of CaVB on channel peak currents and inactivation kinetics. The functional significance of the SH3/GK interaction is demonstrated by the observation that CaV1.2 co-expressed in HEK cells with NSH3+GKC functions normally (similar to CaV1.2 co-expressed with CaVB). However, if GKC[ΔPYDVV], which lacks the ability to interact with NSH3, is used instead, then the channels function as if no CaVB is present (FIG. 2B). These results demonstrate that the SH3/GK interaction is critical for the functional potency of CaVB subunits.

During stress the body releases catecholamines to activate the beta-adrenergic receptor system. In the heart this causes increased heart rate and contractile strength. The primary mechanism by which beta-adrenergic receptor activation affects the heart is by increasing the amount of calcium that enters the cells during contraction. Many forms of arrhythmia, irregular heartbeat, heart failure, and exercise induced angina are caused by inappropriate regulation of the beta-adrenergic receptor system and resultant intracellular calcium overload. Beta-blockers are used to treat these conditions. However, these drugs are non-specific which limits their dosing and efficacy. The inventors have discovered that binding between CACNA1C and CACNB2 is a critical mediator of beta-adrenergic receptor activation. Therefore, drugs that block the Interaction between CACNA1C and CACNB2 are expected to have a therapeutic effect in patients with these conditions.

Moreover, to definitively address the controversies regarding the role of β subunits in mediating trafficking and regulation of $Ca^{2+}$ channels in the heart, in the present disclosure, there is provided transgenic mice lines with three mutations in the AID, which renders the pore-forming $\alpha_{1C}$ subunit incapable of binding β subunits. With this new model, the present disclosure demonstrates in vivo that β subunit binding to $\alpha_{1C}$ is not required for trafficking and that the basal function of β-less $Ca^{2+}$ channels is only minimally altered.

In the present disclosure, it is found that the β subunit is obligatory for transducing β-adrenergic signals to cardiac $Ca_V1.2$ channels. Cardiac $Ca_V1.2$ channels are prominently up-regulated by β-adrenergic agonists via activation of protein kinase A (PKA) (Kamp and Hell 2000; Reuter and Scholz 1977) as part of the fundamental flight or fight response, yet the detailed mechanisms by which PKA activates $Ca_V1.2$ remain unknown despite several decades of investigation. We recently eliminated the long-presumed pore-forming $\alpha_{1C}$ subunit as the relevant PKA target with a comprehensive alanine substitution of all consensus, conserved PKA phosphorylation sites (>22 serines/threonines) in vivo (Katchman et al. 2017). Prior studies also "ruled out" a contribution for the β subunit as substitution or elimination of potential PKA phosphorylation sites did not perturb β-adrenergic regulation (Brandmayr et al. 2012; Lemke et al. 2008; Ganesan et al. 2006; Miriyala et al. 2008), although other consensus PKA sites are present in the N-terminal regions of the protein. It is found that β subunit binding to $\alpha_{1C}$, but not PKA phosphorylation of 1, is absolutely essential for the augmentation of $Ca^{2+}$ current and cardiac contractile response to β-adrenergic-PKA stimulation. These findings identify the key regulatory mechanisms impacting β-adrenergic regulation of $Ca^{2+}$ influx and contractility in the heart.

In view of the foregoing, there exists an ongoing need to provide novel agents that can treat heart diseases by disrupting the CaV1.2-CaVB interaction. The present disclosure is directed towards solving this and other needs.

One embodiment of the present disclosure is a method for identifying a candidate agent that can treat or ameliorate the effects of a heart condition in a subject. This method comprises the steps of:
  a) obtaining a first construct comprising a first signaling moiety attached to CaVB, and obtaining a second construct comprising a second signaling moiety attached to I-IIC (AID) domain of CaV1.2;
  b) co-expressing the first and second constructs in an appropriate cell line;
  c) determining the intensity of a signal specifically generated from the close proximity of the two signaling moieties where the signal can either be self-generated or induced by exposing the cells from step b) to a substrate of the signaling moiety;
  d) repeating steps a) to c) by additionally incubating the cells with a candidate agent before step c); and
  e) identifying the candidate agent as being able to treat or ameliorate the effects of the heart condition, if the intensity of the signal determined in step d) is less than that of step c).

Another embodiment of the present disclosure is a method for identifying a candidate agent that can treat or ameliorate the effects of a heart condition in a subject. This method comprises the steps of:
  a) immobilizing small peptides containing a functional I-IIC alpha interaction domain (AID) domain of CaV1.2 site onto a surface;
  b) incubating CaVB protein that is attached to a signaling moiety;
  c) rinsing the surface to remove any CaVB protein that is not immobilized;
  d) determining the intensity of the signal generated from the surface, where the signal can either be self-generated or induced by exposing the surface to a substrate of the signaling moiety;
  e) repeating steps a) to d) by additionally adding a candidate agent in step b); and
  f) identifying the candidate agent as being able to treat or ameliorate the effects of the heart condition, if the color intensity determined in step e) is less than that of step d).

An additional embodiment of the present disclosure is a method for identifying a candidate agent that can treat or ameliorate the effects of a heart condition in a subject. This method comprises the steps of:
  a) obtaining a first construct comprising an amino or carboxyl terminal portion of a luciferase attached to CaVB, and obtaining a second construct comprising a carboxyl or amino terminal portion of the luciferase attached to I-IIC (AID) domain of CaV1.2;
  b) co-expressing the first and second constructs in an appropriate cell line;
  c) exposing the cells from step b) to a substrate of the luciferase, and determining the intensity of the signal produced;
  d) repeating steps a) to c) by additionally incubating the cells with a candidate agent before step c); and
  e) identifying the candidate agent as being able to treat or ameliorate the effects of the heart condition, if the bioluminescence signal intensity determined in step d) is less than that of step c).

Another embodiment of the present disclosure is a method for identifying a candidate agent that can treat or ameliorate the effects of a heart condition in a subject. This method comprises the steps of:
a) obtaining a first construct comprising an amino or carboxyl terminal portion of a luciferase attached to the amino or carboxyl terminus of src homology 3 (SH3) domain, and obtaining a second construct comprising a carboxyl or amino terminal portion of the luciferase to the carboxyl or amino terminus of guanylate kinase-like (GK) domain;
b) co-expressing the first and second constructs in HEK cells;
c) exposing the HEK cells to a substrate of the luciferase, and determining the intensity of the signal produced;
d) repeating steps a) to c) by additionally incubating the cells with a candidate agent before step c); and
e) identifying the candidate agent as being able to treat or ameliorate the effects of the heart condition, if the bioluminescence signal intensity determined in step d) is less than that of step c).

Another embodiment of the present disclosure is a method for identifying a candidate agent that can treat or ameliorate the effects of a heart condition in a subject. This method comprises the steps of:
a) obtaining a first construct comprising a Flag-tag or HIS-tag attached to amino or carboxyl terminus of CaVB, and obtaining a second construct comprising a HIS-tag or Flag-tag attached to amino or carboxyl terminus of AID (I-IIC) domain of CaV1.2;
b) co-expressing the first and second constructs in bacterial cells;
c) purifying the first and second constructs;
d) incubating the first and second constructs in solution;
e) using anti-Flag and anti-His fluorescent antibodies to tag the first and second constructs;
f) determining the ratio between the intensities of fluorescence at 665 nm and 615 nm (665 nm/615 nm);
g) repeating steps d) to f) by additionally incubating the first and second constructs with a candidate agent before step e); and
h) identifying the candidate agent as being able to treat or ameliorate the effects of the heart condition, if the ratio determined in step g) is less than that of step f).

Another embodiment of the present disclosure is a method for identifying a candidate agent that can treat or ameliorate the effects of a heart condition in a subject. This method comprises the steps of:
a) obtaining a first construct comprising a bungarotoxin binding sequence incorporated into the extracellular side of CaV1.2, and obtaining a second construct comprising a wild type CaVB;
b) co-expressing the first and second constructs in HEK cells;
c) exposing the HEK cells to a bungarotoxin labeled with a signaling moiety, and determining the intensity of the signal produced by the labeled bungarotoxin;
d) repeating steps a) to c) by additionally incubating the cells with a candidate agent before step c); and
e) identifying the candidate agent as being able to treat or ameliorate the effects of the heart condition, if the signal intensity determined in step d) is less than that of step c).

An additional embodiment of the present disclosure is a composition. This composition comprises a pharmaceutically acceptable carrier and one or more candidate agents identified by the methods disclosed herein.

A further embodiment of this disclosure is a method for treating or ameliorating the effects of a heart condition in a subject. This method comprises administering to the subject a therapeutically effective amount of one or more candidate agents identified by the methods disclosed herein.

Yet another embodiment of the present disclosure is a method for specifically blocking the effects of undesired beta-adrenergic receptor activation on calcium levels in a cardiomyocyte of a subject. This method comprises administering to the subject an effective amount of a composition comprising one or more candidate agents identified according to any method disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is a schematic of rabbit cardiac $\alpha_{1C}$ subunit topology showing 1 subunit binding to α-interacting domain (AID) motif in I-II loop. WT and mutant AID motif in the I-II loop of $\alpha_{1C}$. (WT—"QQLEEDLKGYLDWITQAE" (SEQ ID NO: 1); mutant AID—"QQLEEDLK-GALDAATQAE" (SEQ ID NO: 2))

FIG. 6B is a schematic representation of the binary transgene system. The $\alpha MHC_{MOD}$ construct is a modified αMHC promoter containing the tet-operon for regulated expression of FLAG-tagged DHP-resistant (DHP*) $\alpha_{1C}$.

FIG. 6C shows anti-FLAG (upper) and anti-β immunoblots (lower) of anti-FLAG antibody immunoprecipitation of cardiac homogenates of non-transgenic (NTG), pWT $\alpha_{1C}$ and AID-mutant $\alpha_{1C}$ mice. Representative of 3 experiments.

FIG. 6D shows the immunostaining of pWT and AID-mutant $\alpha_{1C}$ cardiomyocytes. Anti-FLAG and FITC-conjugated secondary antibodies, and nuclear labeling with Hoechst stain. Negative control omitted anti-FLAG antibody. Images obtained with confocal microscopy at 40×. Scale bar=20 μm.

FIG. 6E shows the exemplar whole-cell $Ca_V1.2$ currents recorded from freshly dissociated cardiomyocytes of non-transgenic (NTG), pWT and AID-mutant $\alpha_{1C}$ transgenic mice. Pulses from −70 mV to +10 mV before (black traces) and 3 minutes after (red traces) of 300 nM nisoldipine.

FIG. 6F is a scatter plot showing current densities before and after 300 nM nisoldipine. Mean±SEM. *, P<0.05 NTG vs. transgenic pWT $\alpha_{1C}$, **, P<0.0001 NTG vs. transgenic AID-mutant $\alpha_{1C}$ , P<0.0001 NTG pre-vs post-nisoldipine, *, P<0.001 pWT or AID-mutant $\alpha_{1C}$ pre-vs post-nisoldipine. One-way ANOVA and Dunnett's multiple comparison test. NTG: N=8 cardiomyocytes from 5 mice, pWT: N=21 cardiomyocytes from 7 mice, AID-mutant: N=45 cardiomyocytes from 9 mice.

FIG. 6G is the representative time course of changes in sarcomere length after superfusion of 300 nM nisoldipine-containing solution for cardiomyocytes isolated from NTG mice. Cardiomyocytes were field-stimulated at 1-Hz.

FIG. 6H is the representative time course of changes in sarcomere length after superfusion of 300 nM nisoldipine-containing solution for cardiomyocytes isolated from pWT transgenic $\alpha_{1C}$ mice. Cardiomyocytes were field-stimulated at 1-Hz.

FIG. 6I is the representative time course of changes in sarcomere length after superfusion of 300 nM nisoldipine-containing solution for cardiomyocytes isolated from AID-mutant transgenic $\alpha_{1C}$ mice. Cardiomyocytes were field-stimulated at 1-Hz.

FIG. 6J is a scatter plot showing percent contraction of sarcomere length in the absence and presence of nisoldipine for cardiomyocytes isolated from NTG mice, and pWT and AID-mutant $\alpha_{1C}$ transgenic mice. NTG: N=12 cells from 3 mice; pWT: 16 cells from 3 mice; AID-mutant: N=18 cells from 3 mice.

FIG. 7A shows the normalized $Ca_V1.2$ current-voltage relationships for transgenic pWT and AID-mutant $\alpha_{1C}$ cardiomyocytes in presence of nisoldipine. N=19 cardiomyocytes from 3 pWT $\alpha_{1C}$ transgenic mice; N=18 cardiomyocytes from 6 AID-mutant $\alpha_{1C}$ transgenic mice.

FIG. 7B is a scatter dot plot of Boltzmann function parameter $V_{mid}$. **P<0.01, Anova and Sidak's multiple comparison test, N=19 cardiomyocytes from 3 pWT $\alpha_{1C}$ transgenic mice; N=18 cardiomyocytes from 6 AID-mutant $\alpha_{1C}$ transgenic mice.

FIG. 7C is a scatter dot plot of Boltzmann function parameter slope ($V_c$). **P<0.01, Anova and Sidak's multiple comparison test, N=19 cardiomyocytes from 3 pWT $\alpha_{1C}$ transgenic mice; N=18 cardiomyocytes from 6 AID-mutant $\alpha_{1C}$ transgenic mice.

FIG. 7D shows the scatter dot plots of time constants of inactivation at the indicated potentials obtained from a single exponential fit. N=24 pWT $\alpha_{1C}$ cardiomyocytes from 4 mice and N=24 AID-mutant $\alpha_{1C}$ cardiomyocytes from 4 mice. P>0.05 pWT vs. AID-mutant for all voltages using Sidak's multiple comparison test.

FIG. 7E shows the exemplar nisoldipine-resistant current-voltage relationships of transgenic pWT $\alpha_{1C}$ acquired in the absence (black trace) and presence of 200 nM isoproterenol (red trace).

FIG. 7F shows the exemplar nisoldipine-resistant current-voltage relationships of transgenic AID-mutant $\alpha_{1C}$ (F) acquired in the absence (black trace) and presence of 200 nM isoproterenol (red trace).

FIG. 7G is a diary plot of normalized nisoldipine-resistant $I_{Ca}$ amplitude at +10 mV (normalized to 1 at 50 sec prior to isoproterenol) of pWT and AID-mutant $\alpha_{1C}$ cardiomyocytes. Cells exposed to 300 nM nisoldipine followed by 200 nM isoproterenol in the continued presence of nisoldipine. pWT: N=30 cardiomyocytes from 5 mice; AID-mutant: N=45 cardiomyocytes from 7 mice. P<0.0001 by one-way ANOVA/multiple comparison at all time-points 30 sec post-isoproterenol.

FIG. 7H is a diary plot of normalized nisoldipine-resistant $I_{Ca}$ amplitude at +10 mV (normalized to 1 at 50 sec, prior to forskolin) of pWT and AID-mutant $\alpha_{1C}$ cardiomyocytes. Cells exposed to 300 nM nisoldipine followed by 10 μM forskolin in the continued presence of nisoldipine. pWT: N=15 cardiomyocytes from 2 mice; AID-mutant: N=20 cardiomyocytes from 6 mice. P<0.0001 by one-way ANOVA/multiple comparison at all time-points 30 sec post-forskolin.

FIG. 7I is a scatter dot plot of isoproterenol or forskolin-induced fold increase in nisoldipine-resistant $I_{Ca}$. Mean±SEM. *P<0.001; **P<0.0001 by t-test.

FIG. 7J is the graph of isoproterenol and forskolin-induced increase in nisoldipine-resistant current stratified by total basal current density before nisoldipine for pWT $\alpha_{1C}$ and AID-mutant $\alpha_{1C}$ transgenic mice. Lines fitted by linear regression for pWT cells for isoproterenol (black) and forskolin (red). For isoproterenol, pWT $\alpha_{1C}$: N=29 cardiomyocytes; AID-mutant $\alpha_{1C}$: N=45 cardiomyocytes. For forskolin, pWT $\alpha_{1C}$: N=17 cardiomyocytes; AID-mutant $\alpha_{1C}$: N=9 cardiomyocytes.

FIG. 8A shows the adenovirus-induced GFP, AID-YFP and AID-mutant-YFP expression in cultured guinea pig ventricular myocytes. Top, exemplar confocal images from guinea pig cardiomyocytes expressing GFP, AID-YFP peptide or AID mutant-YFP peptide. Bottom, exemplar whole-cell $Ba^{2+}$ currents from GFP, and YFP-expressing guinea pig ventricular cardiomyocyte before (black trace) and after (red trace) application of 1 μM forskolin.

FIG. 8B shows the current-voltage relationship from GFP-expressing cardiomyocytes before (black) and after (red) superfusion of 1 μM forskolin.

FIG. 8C shows the current-voltage relationship from AID-YFP-expressing cardiomyocytes before (black) and after (red) superfusion of 1 μM forskolin.

FIG. 8D shows the current-voltage relationship from AID mutant-YFP-expressing cardiomyocytes before (black) and after (red) superfusion of 1 μM forskolin.

FIG. 8E is the representative dairy plot showing time course of forskolin-induced increase in $Ca_V1.2$ current.

FIG. 8F shows the forskolin-induced increase in $Ca_V1.2$ currents. *P<0.05, **P<0.01 by one-way ANOVA and Tukey's multiple comparison test.

FIG. 9A shows the bright-field and GFP-image of WT and mutant $\beta_{2b}$ expressing cardiomyocytes. Scale bar=100 μm.

FIG. 9B shows the immunoblots using anti-$\beta_2$ antibody (upper) and anti-tubulin antibody of homogenates from the hearts of non-transgenic (NTG) and doxycycline-fed GFP-WT $\beta_2$ and GFP-mutant $\beta_2$ expressing mice.

FIG. 9C shows the graph of densitometry of fraction of GFP-β/total β. Mean±SEM. N=6 mice for NTG, WT and mutant $\beta_2$. P<0.0001 compared to non-transgenic by one-way Anova and Dunnett's multiple comparison test.

FIG. 9D shows the normalized current-voltage relationships of GFP-WT 13 cardiomyocytes acquired before and after superfusion of 200 nM isoproterenol. Isoproterenol shifted the $V_{0.5}$ of steady-state activation by −7.0 mV (P<0.0001, t-test, N=15) and −7.5 mV (P<0.001, t-test, N=30), respectively.

FIG. 9E shows the normalized current-voltage relationships of GFP-mutant $\beta_2$ cardiomyocytes acquired before and after superfusion of 200 nM isoproterenol. Isoproterenol shifted the $V_{0.5}$ of steady-state activation by −7.0 mV (P<0.0001, t-test, N=15) and −7.5 mV (P<0.001, t-test, N=30), respectively.

FIG. 9F is a column scatter plot depicting the fold increase in peak current caused by isoproterenol. Mean±SEM. n=36 cardiomyocytes from 5 NTG mice; N=19 cardiomyocytes from 4 GFP-WT $\beta_{2b}$ mice; N=32 cardiomyocytes from 5 mutant $\beta_{2b}$ mice. P=0.55 by one-way ANOVA.

FIG. 9G show the graphs of isoproterenol-induced increase in current stratified by total basal current density for cardiomyocytes isolated from non-transgenic mice (NTG), GFP-WT $\beta_{2b}$ mice and GFP-mutant $\beta_{2b}$ transgenic mice.

FIG. 10A shows that transgenic pWT $\alpha_{1C}$ cardiomyocytes with robust shortening induced by 1-Hz electrical stimulation in the presence of 300 nM nisoldipine were used. Isoproterenol (200 nM) was superfused with 300 nM nisoldipine.

FIG. 10B shows that transgenic β-less AID-mutant $\alpha_{1C}$ cardiomyocytes with robust shortening induced by 1-Hz electrical stimulation in the presence of 300 nM nisoldipine were used. Isoproterenol (200 nM) was superfused with 300 nM nisoldipine.

FIG. 10C is the plot of isoproterenol-induced fold change in sarcomere length compared to before isoproterenol. Mean±SEM. N=17 for pWT $\alpha_{1C}$ cardiomyocytes and N=19 cardiomyocytes for AID-mutant $\alpha_{1C}$. **P<0.001 by t-test.

FIG. 10D is the plot of isoproterenol-induced % change in $\tau_{relaxation}$ of sarcomere length compared to before isoproterenol. Mean±SEM. N=23 cardiomyocytes from 3 mice and N=32 cardiomyocytes from 3 mice. P=0.16 by t-test.

FIG. 10E shows the representative traces depicted effect of perfusion of 300 nM nisoldipine on left ventricular contraction in isolated Langendorff-perfused hearts resected from non-transgenic mice.

FIG. 10F shows the representative traces depicted effect of perfusion of 300 nM nisoldipine on left ventricular contraction in isolated Langendorff-perfused hearts resected from pWT $\alpha_{1C}$ transgenic mice.

FIG. 10G shows the representative traces of nisoldipine-resistant left ventricular pressure before and during isoproterenol infusion, in hearts resected from pWT $\alpha_{1C}$ transgenic mice.

FIG. 10H shows the representative traces of nisoldipine-resistant left ventricular pressure before and during isoproterenol infusion, in hearts resected from AID-mutant $\alpha_{1C}$ transgenic mice.

FIG. 10I is the quantitative summary of $dP/dt_{max}$ before and during isoproterenol infusion. N=7 pWT $\alpha_{1C}$ transgenic mice; N=11 AID-mutant $\alpha_{1C}$ transgenic mice. *P<0.05 by t-test.

Figure 1:
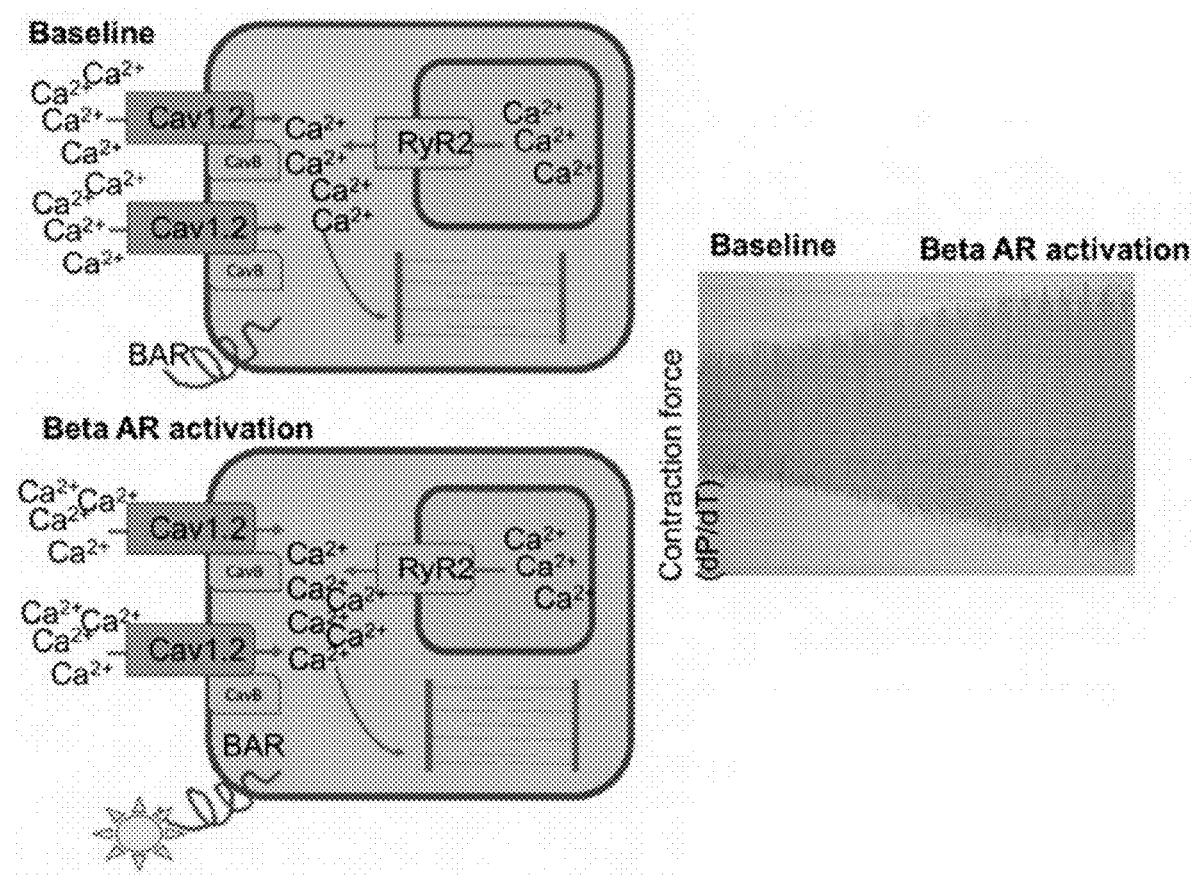
FIG. 1 shows that activation of the beta-adrenergic receptor cascade during exercise and stress causes more calcium to enter the cell through CaV1.2, resulting in increased contractility and improved cardiac output.
Figure 2A:
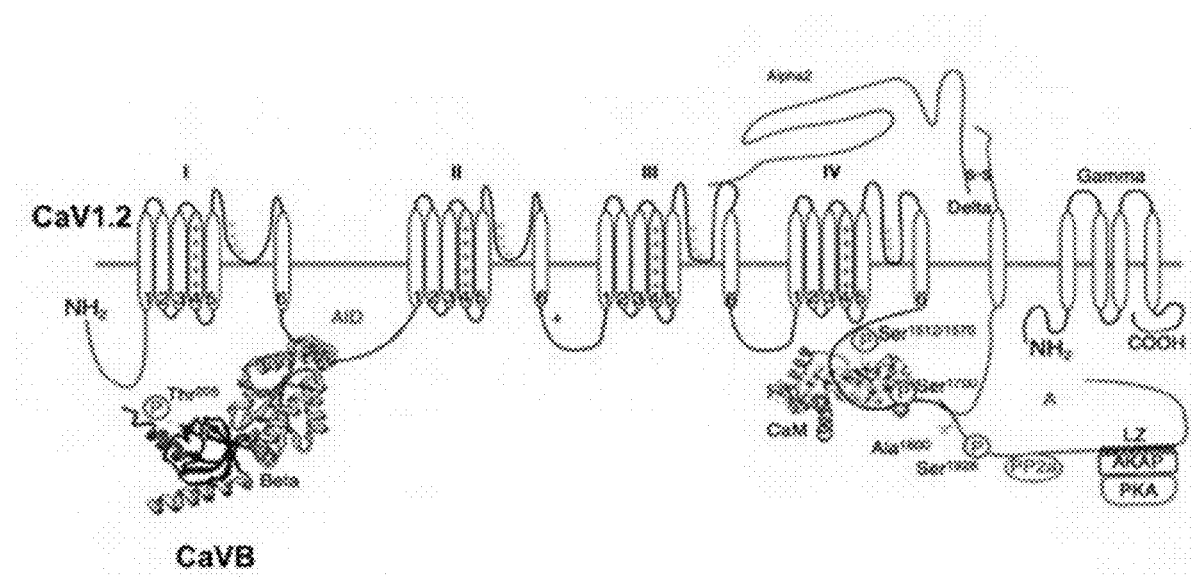
FIG. 2A shows that CaVBs bind to a conserved 18-residue sequence (the alpha interaction domain, or AID) on CaV1.2.
Figure 2B:
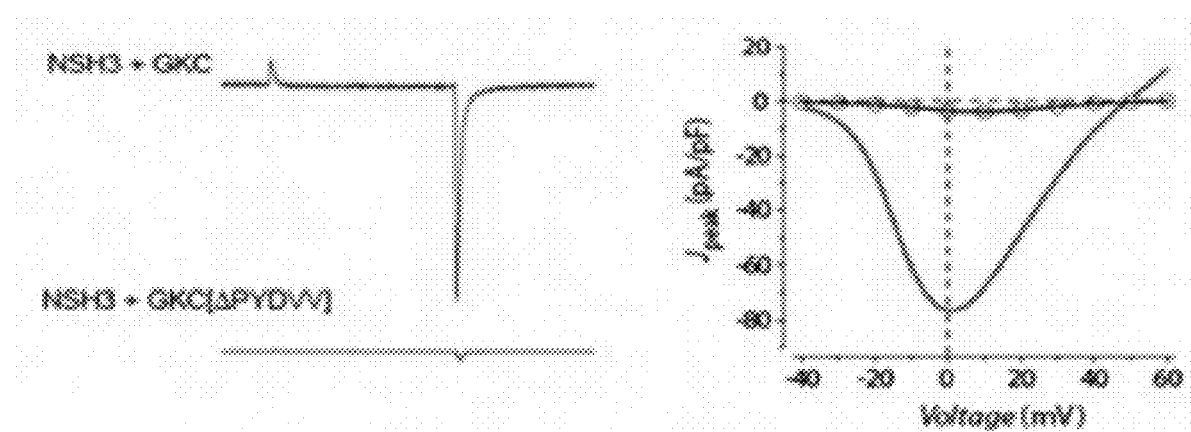
FIG. 2B shows that disruption of the Interaction between SH3 and GK domains abolishes the effects of CaVB on CaV1.2.

FIGS. S1A-S1C show the Expression of AID-mutant $\alpha_{1C}$ in tsA-201 cells.

FIG. S1A shows the anti-β antibody immunoblot (upper) and anti-FLAG antibody (lower) of anti-FLAG antibody immunoprecipitation of homogenates of tsA-201 cells transfected with $\beta_{2b}$ and either FLAG tagged WT $\alpha_{1C}$ or FLAG-tagged AID-mutant $\alpha_{1C}$. Representative of 3 experiments.

FIG. S1B shows the graph of whole cell $Ca^{2+}$ current density of tsA-201 cells transfected with either WT $\alpha_{1C}$ or AID-mutant $\alpha_{1C}$, in absence and presence of $\beta_{2b}$ subunit. Mean±SEM. Data obtained from 3 transfections. P<0.01, P<0.001 by one-way ANOVA and Dunnett's multiple comparisons.

FIG. S1C shows the graph of whole cell $Ca^{2+}$ current density of tsA-201 cells transfected with $\beta_{2b}$ and WT $\alpha_{1C}$, and either DHP-resistant pWT $\alpha_{1C}$ or DHP-resistant AID-mutant $\alpha_{1C}$ (WT: pWT $\alpha_{1C}$/AID-mutant $\alpha_{1C}$ in 1:1 ratio). Cells exposed to 300 nM nisoldipine (red circles).

FIGS. S2A-S2B show that β-adrenergic regulation of phospholamban is normal in AID-mutant transgenic hearts.

FIG. S2A is a representative diary plot of current amplitude (pA/pF) at +10 mV of cardiomyocyte isolated from AID-mutant $\alpha_{1C}$ transgenic mice. In the presence of nisoldipine, Rp-8Br-cAMPS was superfused.

FIG. S2B shows that Cardiomyocytes were isolated from pWT and AID-mutant $\alpha_{1C}$ mice. Cells were exposed to 200 nM isoproterenol. Protein extracts were size-fractionated on SDS-PAGE, transferred to nitrocellulose and blotted with anti-pSer16 phospho-specific antibody (upper blot), and anti-PLB antibody (lower blot). Representative of three similar experiments.

FIG. S3 shows the putative PKA phosphorylation sites in human $\beta_{2b}$ subunit. Residues in red, which are predicted phosphorylation sites, in the N-terminal (NT), Hook and GK domains of $\beta_{2b}$ were mutated to Ala. Residues in the C-terminal (CT) variable region were not mutated to Ala because deletion of the C-terminal region did not alter β-adrenergic regulation of $Ca_V1.2$. (Residue #28: "RPS" (SEQ ID NO: 3) and "RPA" (SEQ ID NO: 31), Residue #58: "KAKT" (SEQ ID NO: 4) and "KAKA" (SEQ ID NO: 32), Residue #143: "KFYS" (SEQ ID NO: 5) and "KFYA" (SEQ ID NO: 33), Residue #150: "KSGGNS" (SEQ ID NO: 6) and "KSGGNA" (SEQ ID NO: 34), Residue #164/65: "RKST" (SEQ ID NO: 7) and "RKAA" (SEQ ID NO: 35), Residue #195: "KPS" (SEQ ID NO: 8) and "KPA" (SEQ ID NO: 36), Residue #215: "KKT" (SEQ ID NO: 9) and "KKA" (SEQ ID NO: 37), Residue #263: "RIS" (SEQ ID NO: 10) and "RIA" (SEQ ID NO: 38), Residue #268: "RVT" (SEQ ID NO: 11) and "RVA" (SEQ ID NO: 39), Residue #277: "KRS" (SEQ ID NO: 12) and "KRA" (SEQ ID NO: 40), Residue #293: "RSNT" (SEQ ID NO: 13) and "RSNA" (SEQ ID NO: 41), Residue #296: "RSS" (SEQ ID NO: 14) and "RSA" (SEQ ID NO: 42), Residue #334: "KTS" (SEQ ID NO: 15) and "KTA" (SEQ ID NO: 43), Residue #345/346: "KISS" (SEQ ID NO: 16) and "KIAA" (SEQ ID NO: 44), Residue #360: "RGKS" (SEQ ID NO: 17) and "RGKA" (SEQ ID NO: 45), Residue #410: "KAT" (SEQ ID NO: 18) and "KAA" (SEQ ID NO: 46), Residue #460: "RSAS" (SEQ ID NO: 19), Residue #474: "KSS" (SEQ ID NO: 20), Residue #478/479/480/481: "RSSSS" (SEQ ID NO: 21), Residue #489/491: "HRSGT" (SEQ ID NO: 22), Residue #496 (PKG site): "RGLSR" (SEQ ID NO: 23), Residue #500: "RQET" (SEQ ID NO: 24), Residue #511: "RDS" (SEQ ID NO: 25), Residue #540: "RDET" (SEQ ID NO: 26), Residue #543/544: "HGSS" (SEQ ID NO: 27), Residue

551/555: "RESRHRS" (SEQ ID NO: 28), Residue #572: "KQRS" (SEQ ID NO: 29), Residue #576: "RHKS" (SEQ ID NO: 30),

DETAILED DESCRIPTION OF THE INVENTION $Ca^{2+}$ channel β-subunit interactions with pore-forming α-subunits are long-thought to be obligatory for channel trafficking to the cell surface and for tuning of basal biophysical properties in many tissues. In the present disclosure, it is demonstrated that transgenic expression of mutant $α_{1C}$ subunits lacking capacity to bind $Ca_V β$ can traffic to the sarcolemma in adult cardiomyocytes in vivo and sustain normal excitation-contraction coupling. However, these β-less $Ca^{2+}$ channels cannot be stimulated by β-adrenergic pathway agonists, and thus adrenergic-augmentation of contractility is markedly impaired in isolated cardiomyocytes and in hearts. Similarly, viral-mediated expression of a β-subunit-sequestering-peptide sharply curtailed β-adrenergic stimulation of wild-type $Ca^{2+}$ channels, identifying a novel approach to specifically modulate β-adrenergic regulation of cardiac contractility. The present disclosure demonstrates that β subunits are required for β-adrenergic regulation of $Ca_V 1.2$ channels and positive inotropy in the heart, but are dispensable for $Ca_V 1.2$ trafficking to the adult cardiomyocyte cell surface, and for basal function and excitation-contraction coupling.

The present disclosure provides methods for screening small molecules that disrupt the interaction between CaVB and $Ca_V 1.2$, by either targeting the AID domain (direct interaction of CaV1.2 and CaVB) or the SH3/GK interaction (within CaVB).

One embodiment of the present disclosure is a method for Identifying a candidate agent that can treat or ameliorate the effects of a heart condition in a subject. This method comprises the steps of:
a) obtaining a first construct comprising a first signaling moiety attached to CaVB, and obtaining a second construct comprising a second signaling moiety attached to I-IIC (AID) domain of CaV1.2;
b) co-expressing the first and second constructs in an appropriate cell line;
c) determining the intensity of a signal specifically generated from the close proximity of the two signaling moieties where the signal can either be self-generated or induced by exposing the cells from step b) to a substrate of the signaling moiety;
d) repeating steps a) to c) by additionally incubating the cells with a candidate agent before step c); and
e) identifying the candidate agent as being able to treat or ameliorate the effects of the heart condition, if the intensity of the signal determined in step d) is less than that of step c).

Another embodiment of the present disclosure is a method for identifying a candidate agent that can treat or ameliorate the effects of a heart condition in a subject. This method comprises the steps of:
a) immobilizing small peptides containing a functional I-IIC alpha interaction domain (AID) domain of CaV1.2 site onto a surface;
b) incubating CaVB protein that is attached to a signaling moiety;
c) rinsing the surface to remove any CaVB protein that is not immobilized;
d) determining the intensity of the signal generated from the surface, where the signal can either be self-generated or induced by exposing the surface to a substrate of the signaling moiety;
e) repeating steps a) to d) by additionally adding a candidate agent in step b); and
f) identifying the candidate agent as being able to treat or ameliorate the effects of the heart condition, if the color intensity determined in step e) is less than that of step d).

Another embodiment of the present disclosure is a method for identifying a candidate agent that can treat or ameliorate the effects of a heart condition in a subject. This method comprises the steps of:
a) obtaining a first construct comprising an amino or carboxyl terminal portion of a luciferase attached to CaVB, and obtaining a second construct comprising a carboxyl or amino terminal portion of the luciferase attached to I-IIC (AID) domain of CaV1.2;
b) co-expressing the first and second constructs in an appropriate cell line;
c) exposing the cells from step b) to a substrate of the luciferase, and determining the intensity of the signal produced;
d) repeating steps a) to c) by additionally incubating the cells with a candidate agent before step c); and
e) identifying the candidate agent as being able to treat or ameliorate the effects of the heart condition, if the bioluminescence signal intensity determined in step d) is less than that of step c).

Another embodiment of the present disclosure is a method for identifying a candidate agent that can treat or ameliorate the effects of a heart condition in a subject. This method comprises the steps of:
a) obtaining a first construct comprising an amino or carboxyl terminal portion of a luciferase attached to the amino or carboxyl terminus of src homology 3 (SH3) domain, and obtaining a second construct comprising a carboxyl or amino terminal portion of the luciferase to the carboxyl or amino terminus of guanylate kinase-like (GK) domain;
b) co-expressing the first and second constructs in HEK cells;
c) exposing the HEK cells to a substrate of the luciferase, and determining the intensity of the signal produced;
d) repeating steps a) to c) by additionally incubating the cells with a candidate agent before step c); and
e) identifying the candidate agent as being able to treat or ameliorate the effects of the heart condition, if the bioluminescence signal intensity determined in step d) is less than that of step c).

Another embodiment of the present disclosure is a method for identifying a candidate agent that can treat or ameliorate the effects of a heart condition in a subject. This method comprises the steps of:
a) obtaining a first construct comprising a Flag-tag or HIS-tag attached to amino or carboxyl terminus of CaVB, and obtaining a second construct comprising a HIS-tag or Flag-tag attached to amino or carboxyl terminus of AID (I-IIC) domain of CaV1.2;
b) co-expressing the first and second constructs in bacterial cells;
c) purifying the first and second constructs;
d) incubating the first and second constructs in solution;
e) using anti-Flag and anti-His fluorescent antibodies to tag the first and second constructs;

f) determining the ratio between the intensities of fluorescence at 665 nm and 615 nm (665 nm/615 nm);
g) repeating steps d) to f) by additionally incubating the first and second constructs with a candidate agent before step e); and
h) identifying the candidate agent as being able to treat or ameliorate the effects of the heart condition, if the ratio determined in step g) is less than that of step f).

In this embodiment, the method may be carried out in any suitable substrate, such as a multi-well device. In this embodiment the determining step may Include adding an anti-FITC antibody, which does not cross the cell membrane, optionally followed by a washing step. The anti-FITC antibody may be, e.g., a LANCE Eu-anti-FITC. In this embodiment, if CaV1.2 is expressed in the cell, then a FITC signal may be detected. Furthermore, if CaV1.2 interacts with, e.g., is bound to, CaVB, then the channel will traffic to the cell membrane and bind to the anti-FITC antibody, e.g., a LANCE Eu-anti-FITC. The signal from the anti-FITC antibody may be detected using any appropriate detection methodology. For example, detection may be accomplished by exciting at 320 nm and detecting at 615 nm. Candidate agents, such as, e.g., small molecules that interfere with AID-CaVB interaction will result in a lower 615 nm emission. In this embodiment, Alamar blue may be used to concurrently assess cell viability at each candidate agent concentration.

In some embodiments, the Flag-tag or the His-Tag is replaced by a tag selected from the group consisting of c-myc, FITC, GST, HA, V5 tag, and Streptavidin.

Another embodiment of the present disclosure is a method for identifying a candidate agent that can treat or ameliorate the effects of a heart condition in a subject. This method comprises the steps of:
a) obtaining a first construct comprising a bungarotoxin binding sequence incorporated into the extracellular side of CaV1.2, and obtaining a second construct comprising a wild type CaVB;
b) co-expressing the first and second constructs in HEK cells;
c) exposing the HEK cells to a bungarotoxin labeled with a signaling moiety, and determining the intensity of the signal produced by the labeled bungarotoxin;
d) repeating steps a) to c) by additionally incubating the cells with a candidate agent before step c); and
e) identifying the candidate agent as being able to treat or ameliorate the effects of the heart condition, if the signal intensity determined in step d) is less than that of step c).

An additional embodiment of the present disclosure is a composition. This composition comprises a pharmaceutically acceptable carrier and one or more candidate agents identified by the methods disclosed herein.

A further embodiment of this disclosure is a method for treating or ameliorating the effects of a heart condition in a subject. This method comprises administering to the subject a therapeutically effective amount of one or more candidate agents identified by the methods disclosed herein.

Yet another embodiment of the present disclosure is a method for specifically blocking the effects of undesired beta-adrenergic receptor activation on calcium levels in a cardiomyocyte of a subject. This method comprises administering to the subject an effective amount of a composition comprising one or more candidate agents identified according to any method disclosed herein.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the agents identified by the methods of the present disclosure and the compositions comprising one or more of these agents may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population, may fail to respond or respond inadequately to treatment.

As used herein, the terms "ameliorate", "ameliorating" and grammatical variations thereof mean to decrease the severity of the symptoms of a disease in a subject.

As used herein, the term "administering" means oral administration, administration as a suppository, topical contact, intravenous, intraperitoneal, intramuscular, intralesional, intranasal or subcutaneous administration, or the implantation of a slow-release device, e.g., a mini-osmotic pump, to a subject. Administration is by any route including parenteral, and transmucosal (e.g., oral, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, microbubbles (including ultrasound-mediated microbubble destruction), and the like.

In the present disclosure, an "effective amount" or "therapeutically effective amount" of an agent or pharmaceutical composition is an amount of such an agent or composition that is sufficient to affect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of the subject, and like factors well known in the arts of, e.g., medicine and veterinary medicine. In general, a suitable dose of an agent or pharmaceutical composition according to the disclosure will be that amount of the agent or composition, which is the lowest dose effective to produce the desired effect with no or minimal side effects. The effective dose of an agent or pharmaceutical composition according to the present disclosure may be administered as two, three, four, five, six or more sub-doses, administered separately at appropriate intervals throughout the day.

A suitable, non-limiting example of a dosage of an agent or pharmaceutical composition according to the present disclosure or a composition comprising such an agent, is from about 1 ng/kg to about 1000 mg/kg, such as from about 1 mg/kg to about 100 mg/kg, including from about 5 mg/kg to about 50 mg/kg. Other representative dosages of an agent or a pharmaceutical composition of the present disclosure include about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 400 mg/kg, 500 mg/kg, 600 mg/kg, 700 mg/kg, 800 mg/kg, 900 mg/kg, or 1000 mg/kg.

As used herein, a "signaling moiety" refers to a structure or matter that can generate a detectable signal in some form under certain conditions. Non-limiting examples of a signaling moiety according to the present disclosure include: peroxidase enzyme, luciferase, fluorophore, fluorescent protein, fluorescent dye, lanthanide, quantum dot, biotin, digoxin, hapten, epitope, and radioisotope. Preferably, the luciferase is a split fire luciferase. Preferably, the peroxidase enzyme is a horseradish peroxidase (HRP) or an engineered ascorbate peroxidase (APEX). The signal generated by a signaling moiety includes, but is not limited to: color, fluorescence, bioluminescence and radiation.

In the screening methods of the present disclosure, one or more of the binding partners may be immobilized on a suitable substrate, such as, e.g., a 96-well plate. The candidate agents of the present disclosure may be any suitable molecules that have the potential to treat or ameliorate a heart condition caused by the effects of abnormal beta-adrenergic receptor activation on calcium levels in cardiac myocytes. For example, suitable candidate agents include, but are not limited to: antibodies, RNAi, siRNA, shRNA, antisense sequences, peptides and small molecules.

As used herein, with respect to the screening methods, an "appropriate cell line" is any cell that can co-express the constructs of the present disclosure. Non-limiting examples of appropriate cell lines include HEK cells, COS7 cells, HeLa cells (Human Cervical Adenocarcinoma Cells), Neuro-2a cells, NIH 3T3 mouse embryonic fibroblast cells, U2OS (human bone osteosarcoma epithelial cells), RPE-1 (retinal pigment epithelial cells, human), DLD-1 (human colon cancer cells), L929 (mouse fibroblast cell line), DT40 (chicken lymphoma cell line), CHO (Chinese hamster ovary cell line, epithelial-like), and sf9 (insect epithelial cells). Non-limiting examples of bacterial cell lines that can be used for expressing soluble proteins include Express Duo BL21 chemically competent cells.

As used herein, a "heart condition" or "heart disease" refers to any type of disorder that affects the heart and that is caused by the effects of abnormal beta-adrenergic receptor activation on calcium levels in cardiac myocytes, or by normal effect of beta-adrenergic receptor activation on contractility which may be detrimental (e.g. in HOCM increased contractility results in worsening outflow tract gradient). Non-limiting examples of a heart condition according to the present disclosure include: cardiovascular disease, myocardial infarction, coronary artery disease, heart failure, heart arrhythmia, congenital heart defect, angina, angina pectoris, atrial fibrillation, cardiomyopathy, heart valve disease, hypercholesterolemia, chest pain, shortness of breath, cardiac arrest, atheroma, tachycardia, peripheral artery disease, pericarditis, syncope, hypertension, hypotension, endocarditis, myocarditis, ventricular septal defect, aortic stenosis, rheumatic fever, dilated cardiomyopathy, aortic aneurysm, hypertrophic cardiomyopathy, mitral valve prolapse, bradycardia, atrial septal defect, arteriosclerosis, supraventricular tachycardia, heart block, atrial flutter, long QT syndrome, paroxysmal tachycardia, ventricular fibrillation, marfan syndrome, cardiomegaly, ventricular tachycardia, embolism, premature ventricular contraction, cyanosis, restrictive cardiomyopathy, hypertensive heart disease, tetralogy of fallot, mitral insufficiency, pulseless electrical activity, acute coronary syndrome, pulmonary hypertension, etc.

In some embodiments, the heart condition is selected from the group consisting of systolic heart failure, atrial arrhythmias, ventricular arrhythmias, hypertrophic cardiomyopathy, hypertension and catecholaminergic polymorphic ventricular tachycardia (CPVT).

In some embodiments, the heart condition is selected from the group consisting of arrhythmia, hypertrophic cardiomyopathy, hypertension, diastolic dysfunction or heart failure with preserved ejection fraction, systolic heart failure or heart failure with reduced ejection fraction, and coronary artery disease. In particular, arrhythmia includes atrial arrhythmia and ventricular arrhythmia such as Inherited ventricular arrhythmia and acquired ventricular arrhythmia. Inherited ventricular arrhythmia includes catecholaminergic polymorphic ventricular tachycardia (CPVT), long QT syndrome (LQTS) and arrhythmogenic right ventricular dysplasia (ARVD). Acquired ventricular arrhythmia includes scar related and adrenergic mediated ventricular arrhythmias. Atrial arrhythmia includes atrial fibrillation, atrial flutter and atrial tachycardia. Hypertrophic cardiomyopathy includes hemodynamic consequences such diastolic dysfunction and left ventricular outflow tract obstruction, and arrhythmia consequences such as ventricular arrhythmias consequences and atrial arrhythmias consequences. Systolic heart failure/heart failure with reduced ejection fraction includes ventricular arrhythmias in systolic heart failure, progression of cardiac dysfunction in systolic heart failure, and stress induced cardiomyopathy. Coronary artery disease includes angina, ventricular arrhythmias myocardial infarction, and systolic heart failure as a consequence of coronary artery disease.

As used herein, a "subject" is a mammal, preferably, a human. In addition to humans, categories of mammals within the scope of the present disclosure include, for example, agricultural animals, veterinary animals, laboratory animals, etc. Some examples of agricultural animals include cows, pigs, horses, goats, etc. Some examples of veterinary animals include dogs, cats, etc. Some examples of laboratory animals include primates, rats, mice, rabbits, guinea pigs, etc.

A composition of the present disclosure may be administered in any desired and effective manner: for oral ingestion, or as an ointment or drop for local administration to the eyes, or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present disclosure may be administered in conjunction with other treatments. A composition of the present disclosure may be encapsulated or otherwise protected against gastric or other secretions, if desired.

The compositions of the disclosure are pharmaceutically acceptable and may comprise one or more active ingredients in admixture with one or more pharmaceutically-acceptable carriers and, optionally, one or more other agents, drugs, ingredients and/or materials. Regardless of the route of administration selected, the agents of the present disclosure are formulated into pharmaceutically-acceptable dosage forms by conventional methods known to those of skill in the art. See, e.g., Remington, The Science and Practice of Pharmacy (21st Edition, Lippincott Williams and Wilkins, Philadelphia, Pa.). More generally, "pharmaceutically acceptable" means that which is useful in preparing a composition that is generally safe, non-toxic, and neither biologically nor otherwise undesirable and includes that which is acceptable for veterinary use as well as human pharmaceutical use.

Pharmaceutically acceptable carriers are well known in the art (see, e.g., Remington, The Science and Practice of Pharmacy (21st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a composition of the disclosure must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art. In some embodiments, the suitable carrier is a microbubble.

In some embodiments, the screening methods disclosed are carried out in vitro. In other embodiments, the screening methods disclosed are carried out in vivo or ex vivo.

As used herein, in vitro refers to a process performed in an artificial environment created outside a living multicellular organism (e.g., a test tube or culture plate or Langendorff heart/isolated perfused heart assay) used in experimental research to study a disease or process. As used herein, in vitro includes processes performed in intact cells growing in culture.

As used herein, in vivo means that which takes place inside an organism and more specifically to a process performed in or on the living tissue of a whole, living multicellular organism (animal), such as a mammal, as opposed to a partial or dead one.

As used herein, ex vivo refers to a process performed in an artificial environment outside the organism on living cells or tissue which are removed from an organism and subsequently returned to an organism.

The compositions of the disclosure may, optionally, contain additional ingredients and/or materials commonly used in such compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropyl methyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other Ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and Inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Compositions suitable for parenteral administrations comprise one or more agent(s)/compound(s) in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

EXAMPLES

The disclosure is further illustrated by the following examples, which are offered for illustrative purposes, and are not intended to limit the disclosure in any manner. Those of skill in the art will readily recognize a variety of non-critical parameters, which can be changed or modified to yield essentially the same results.

Example 1

Figure 3:
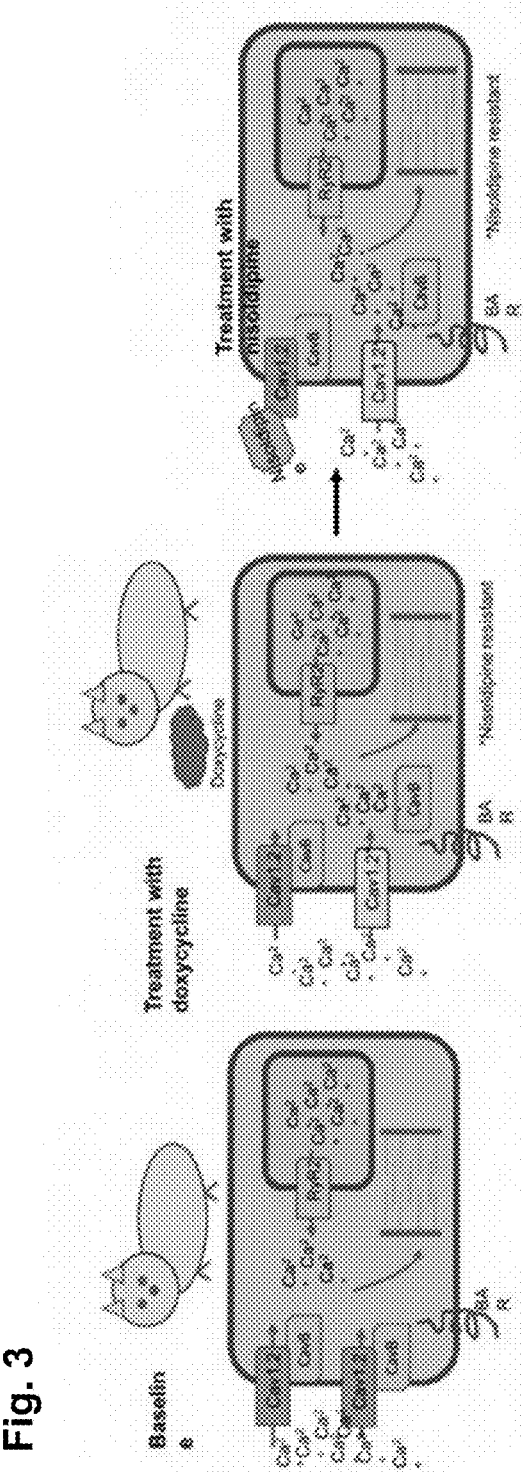
FIG. 3 shows that treating a transgenic mouse with doxycycline results in expression of mutant CaV1.2 channels.

CaV1.2-CaVB Interaction Regulates the Intracellular Calcium Response to Beta-Adrenergic Receptor Activation In order to study whether the CaV1.2-CaVB interaction regulates the intracellular calcium response to beta-adrenergic receptor activation, we developed a transgenic mouse which when treated with doxycycline expresses CaV1.2 channels that have two distinct features: 1) lack the AID domain, and therefore do not bind to CaVB; 2) are not affected by the calcium channel blocking drug nisoldipine. Treating the adult mice with doxycycline results in expression of the mutant CaV1.2 channels (FIG. 3).

Figure 4A:
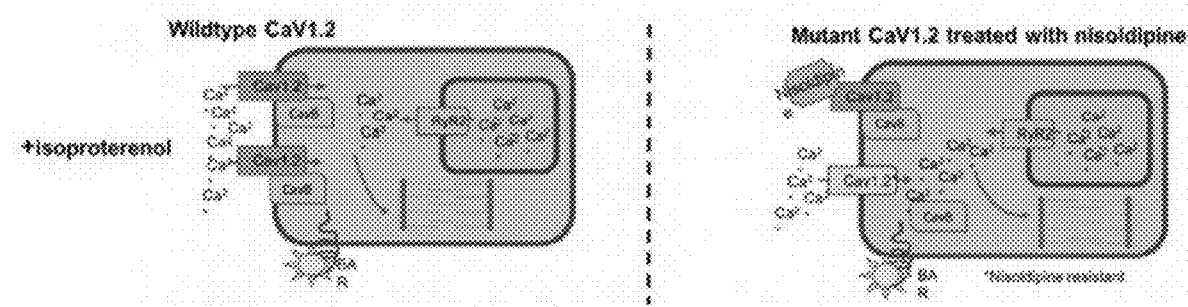
FIG. 4A shows that native CaV1.2 channels are first inhibited with nisoldipine and then isoproterenol is added in order to activate the beta-adrenergic receptor system.
Figure 4B:
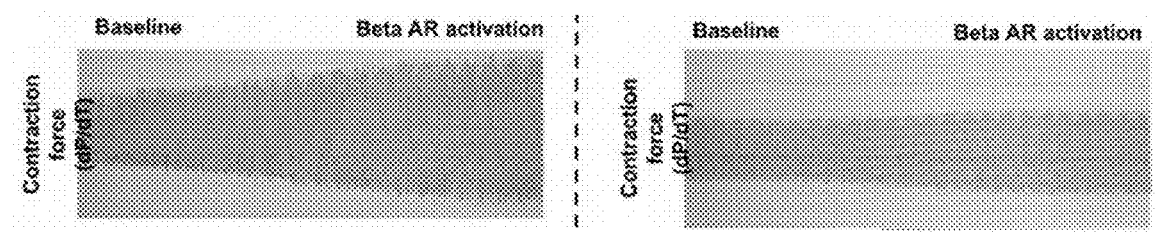
FIG. 4B shows that control mice exhibited a 75-200% increase in contractility in response to isoproterenol, while the mutant mice exhibited only a 0-25% increase.
Figure 4C:
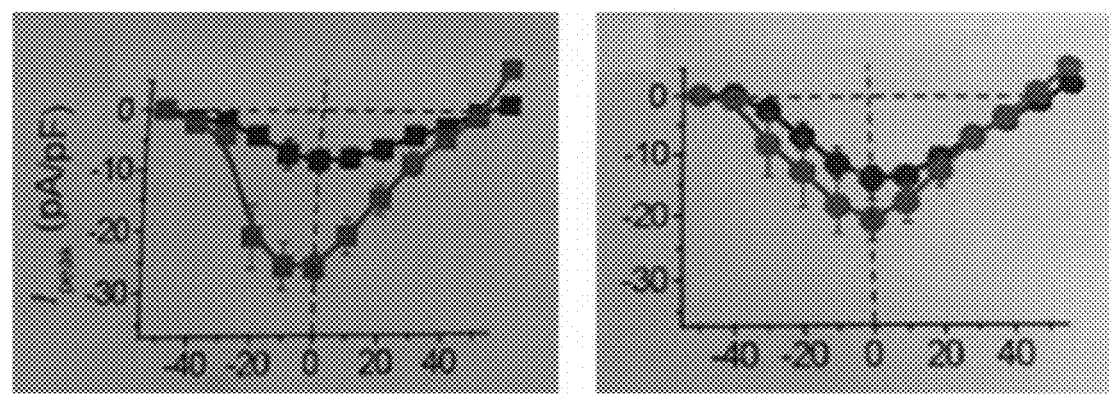
FIG. 4C shows that cardiomyocytes isolated from mutant hearts (right panel) exhibited reduced transmembrane current compared to control animals (left panel) when treated with isoproterenol (red) vs baseline (black).

Hearts from these mice are isolated and contractility is assessed by placing a balloon in the left ventricle. The native CaV1.2 channels are first inhibited with nisoldipine and then isoproterenol is added in order to activate the beta-adrenergic receptor system (FIG. 4A). Control mice exhibit a 75-200% increase in contractility in response to isoproterenol, however, the mutant mice exhibit only a 0-25% increase (FIG. 4B). Additionally, cardiomyocytes isolated from these mutant hearts exhibit reduced transmembrane current compared to control animals when treated with isoproterenol (FIG. 4C). These data revolutionize the field of cardiac physiology by demonstrating that the increase in contractility in response to beta-adrenergic activation can be almost completely inhibited by preventing the interaction between $Ca_V1.2$ and CaVB.

This data strongly suggests that blocking the interaction between $Ca_V1.2$ and CaVB using small molecules would create a novel class of drugs that can have a major impact on the management of millions of patients with heart disease.

Example 2

Screening Small Molecules that Disrupt the Interaction Between CaVB and Cav1.2

Methods for screening small molecules that disrupt the interaction between CaVB and CaV1.2 were developed, by either targeting the AID domain (direct interaction of CaV1.2 and CaVB) or the SH3/GK interaction (within CaVB).

The first approach (first method) involves: 1) immobilizing small peptides containing a functional AID site into small wells on a 96-well plate; 2) adding a random small molecule from a commercially available small molecule library into each well; 3) adding CaVB attached to a peroxidase enzyme (e.g. HRP, APEX); 4) incubating; 5) washing; 6) adding HRP substrate; 7) measuring color intensity generated when the peroxidase catalyzes the reaction of HRP substrate using a spectrophotometer. If the interaction between the AID site and CaVB is blocked then there will be less intensity. The degree of "colorlessness" correlates with degree of interaction block.

An alternative screening method (second method) based on the first approach is a FRET based screen, which consists of combining the AID peptide (specific fragment of CaV1.2 that binds to CaVB), together with CaVB in solution. The AID peptide contains a 6× His-tag, and CaVB contains a Flag-tag. Protein-protein interaction in the presence of small molecule inhibitors will be assessed using Lanthanide chelate excite (LANCE) based fluorophores. The AID peptide is fluorescently labeled with an Eu-anti-6× His, which absorbs light at 320 nm and emits at 615 nm. CaVB is labeled with ULight-anti-FLAG which absorbs at 615 nm and emits at 665 nm. If fluorescently labeled AID and CavB interact, then exciting at 320 nm will result in a 665 nm emission. Data is presented as a ratio between fluorescence at 665 and 615 nm (bound:unbound AID ratio). Candidate agents, such as, e.g., small molecules that interfere with AID-CavB interaction will result in a lower ratio. The LANCE system does not require washing steps, making it easier to interrogate low affinity interactions. It is also stable for long periods of time making it an optimal choice for high-throughput screens.

Candidate agents, such as, e.g., small molecules identified by the aforementioned methods will be further tested to assess the lowest concentration required to inhibit the interaction between AID and CaVB. Concentration response curves can be determined, for example, using the FRET based method, using different concentrations of, e.g., small molecules.

The second approach focuses on a protein complementation approach based on split firefly luciferase. 1) In one embodiment (third method), the amino terminal portion of luciferase is attached to CaVB (CaVB-NFluc), and the carboxyl terminal portion is attached to I-IIC domain of CaV1.2 (I-IIC-CFluc). In another embodiment (fourth method), the amino terminal portion of luciferase is attached to NSH3 (NFluc-NSH3), and carboxyl terminal portion is attached to GKC (GKC-CFluc); 2) CaVB-NFluc and I-IIC-CFluc or NFluc-NSH3 and GKC-CFluc are co-expressed in HEK cells; 3) The cells are exposed to the luciferase substrate; 4) cells with interaction between the two proteins will exhibit bioluminescence.

Figure 5A:
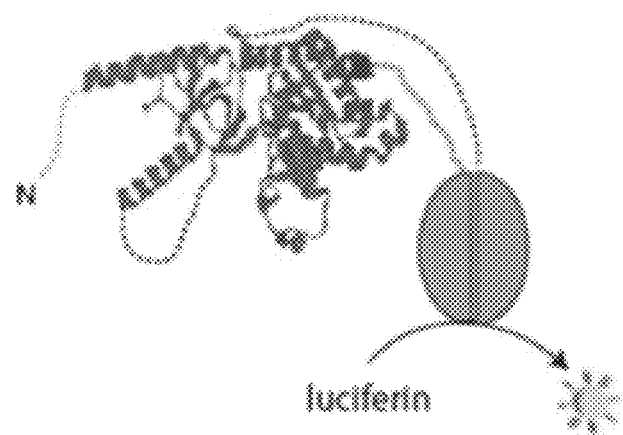
FIG. 5A shows a screening method based on the CaVB-NFluc and I-IIC-CFluc interaction.
Figure 5B:
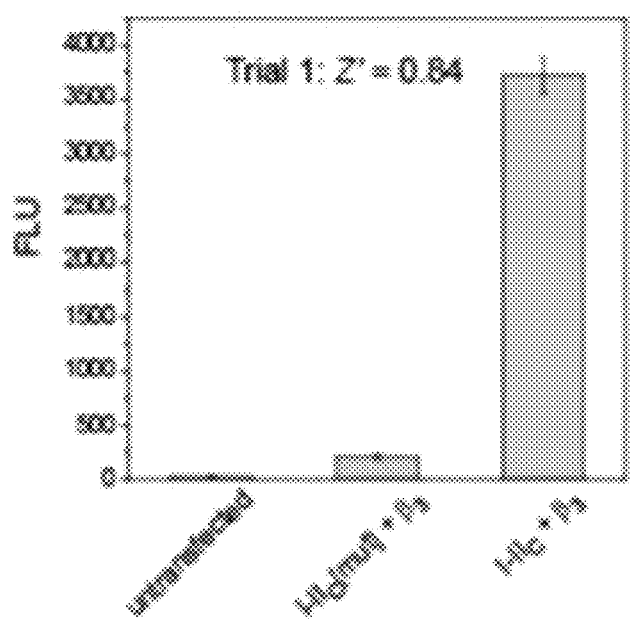
FIG. 5B shows that cells transfected with CaVB-NFluc and I-IIC-Cfluc exhibited higher bioluminescence signal than that of the negative control.
Figure 5C:
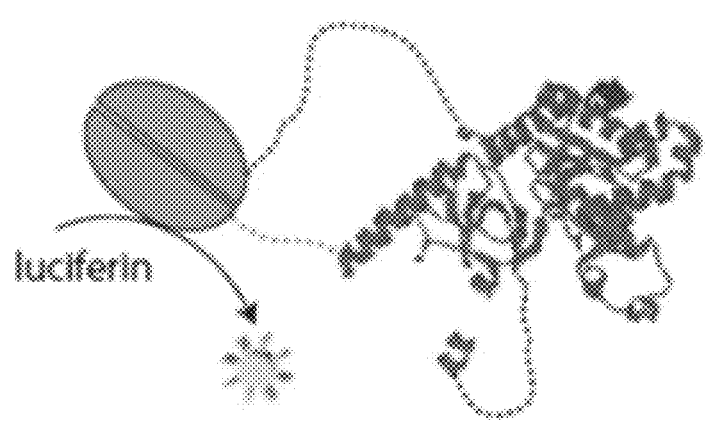
FIG. 5C shows a screening method based on the NFluc-NSH3 and GKC-CFluc interaction.
Figure 5D:
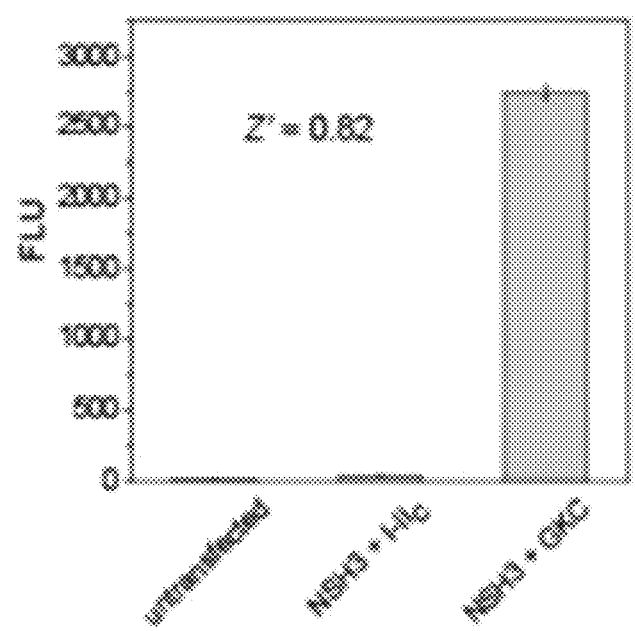
FIG. 5D shows that cells transfected with NFluc-NSH3 and GKC-CFluc exhibited higher bioluminescence signal than that of the negative control.

The results of the second approach (third and fourth methods) are shown in FIGS. 5A-5D. Untransfected cells exhibited negligble bioluminescence signal. Cells co-expressing CaVB-NFluc and I-IIC-CFluc (FIG. 5A) exhibited a robust bioluminescence signal that was over 15-fold greater than seen with the negative control (FIG. 5B). Bioluminescence obtained from cells transfected with NFluc-NSH3+GKC-CFluc (FIG. 5C) was over 70-fold greater than readings from negative control cells (FIG. 5D).

Another screening method (fifth method) based on the second approach takes advantage of the fact that in order for CaV1.2 to traffic to the plasma membrane in HEK (eukaryotic cells) cells, it needs to be bound to CaVB. HEK cells will be co-transfected with $Ca_V1.2$ linked to a FITC-tag on its extracellular surface, and CaVB. Candidate agents, such as, e.g., small molecules, at different concentrations, will be incubated with the cells. LANCE Eu-anti-FITC, which does not cross the cell membrane, will be added to the well and washed off. If CaV1.2 is expressed in the cell, then there will be a FITC signal detected. If CaV1.2 is bound to CaVB then the channel will traffic to the cell membrane and bind to LANCE Eu-anti-FITC, which can be detected by exciting at 320 nm and detecting at 615 nm. Candidate agents, such as, e.g., small molecules that interfere with AID-CaVB interaction will result in a lower 615 nm emission. Alamar blue may be used concurrently to assess cell viability at each compound concentration.

These methods can be used independently or sequentially. The first method can be used as a mass screening tool, which is simple and direct. The third method provides information regarding whether a compound can cross cell membranes and inhibit beta-subunit binding to CaV1.2 in vivo. The fourth and fifth methods directly assess the interaction between CaV1.2 and CaVB in vivo. By sequentially combining these methods we can screen, for example, mass small chemical compound libraries to identify potential drugs for further experimentation and development.

Example 3

Ex Vivo Functional Assessment

The most potent, few remaining candidate agents, e.g., small molecules identified by the approaches disclosed in Example 2 will be tested on mouse hearts, ex vivo, to assess their ability to block the effects of beta-adrenergic receptor activation on cardiac contractility. The candidate agents, e.g., small molecules, will be dissolved in a standard Tyrode's solution. Wildtype mouse hearts will be explanted, cannulated at the aorta, and perfused retrograde using the Langendorff technique. A pressure-sensing balloon will be placed into the left ventricle (LV) through the left atrium/mitral valve. LV contractility is then measured at baseline and in the presence of the beta-adrenergic receptor agonist isoproterenol. A successful candidate agent, e.g., small molecule inhibitor is expected to blunt the effect of isoproterenol on cardiac contractility.

Example 4

Methods and Materials

Reagents

Nisoldipine and Rp-8-Br-cAMPS were purchased from Santa Cruz Biotechnology. All other chemicals were acquired from Sigma.

Animals

Figure 6A:
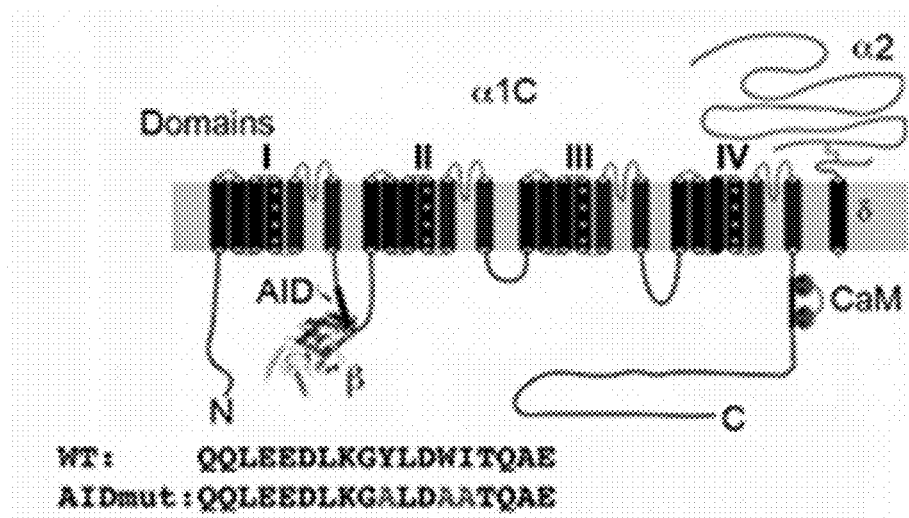
FIGS. 6A-6J show the AID-mutant $\alpha_{1C}$ channels trafficking and function in cardiomyocytes.

The $\alpha_{1C}$ transgenic constructs were generated by fusing rabbit Cacna1c cDNA (accession X15539) to the modified murine α-myosin heavy chain (MHC), tetracycline-inducible promoter ("responder" line) vector (gift of Drs. Jeffrey Robbins and Jeffrey Molkentin, University of Cincinnati, Cincinnati, Ohio) (Sanbe et al. 2003; Hambleton et al. 2007). The $\alpha_{1C}$ subunit was engineered to be both dihydropyridine (DHP)-insensitive with the substitutions T1066Y and Q1070M (He et al. 1997; Hockerman et al. 1997) and tagged with a 3×-FLAG-epitope. We made alanine-substitutions of three conserved residues: Y467, W470 and I471 in the AID domain of rabbit $\alpha_{1C}$ (FIG. 6A). Two distinct AID-mutant $\alpha_{1C}$ mice were created and studied. The results obtained from each of these lines were equivalent and therefore the data were pooled. The $\beta_{2b}$ transgenic constructs were generated by ligating a N-terminal GFP-tagged human CACNB2b cDNA (accession #AF285239) to the tetracycline-inducible vector. These mice were bred with cardiac specific (αMHC) doxycycline-regulated codon-optimized reverse transcriptional transactivator (rtTA) mice (obtained via MMRRC) (Valencik and McDonald 2001) to generate double transgenic mice. The $\alpha_{1C}$ transgenic animals received 0.2 g/kg doxycycline-impregnated food (Bio Serv Cat #S3888) for 1-2 days and the GFP-$\beta_{2b}$ transgenic mice received the doxycycline-impregnated food for 1 week to maximize expression.

Generation of Adenoviral Vectors and Infection of Guinea Pig Ventricular Cardiomyocytes Replication deficient adenoviral vectors expressing AID-YFP and AIDmut-YFP were generated using the AdEasy Adenoviral Vector System (Agilent Technologies) according to the manufacturer's instructions. Briefly, sequences for AID-YFP and AIDmut-YFP were PCR-amplified and cloned into pShuttle-CMV vector. After linearization with PmeI, shuttle vectors were electroporated into BJ5183 cells containing pAdEasy-1 viral plasmid. Positive recombinants were amplified, linearized with Pac I, and transfected into AD-293 cells using the calcium phosphate precipitation method. Transfected cells were monitored for development of adenoviral plaques, after which the cells were freeze-thawed and the lysate used to infect a 10-cm dish of 90% confluent HEK293 cells. Viral expansion and purification was carried out as previously described (Colecraft et al. 2002).

Adult guinea pig ventricular myocytes were isolated by enzymatic digestion using a Langendorff perfusion apparatuses, and cultured as previously described (Miriyala et al. 2008). Animal treatment and use were in accordance with a protocol approved by the Columbia University Institutional Animal Care and Use Committee. Heart cells were infected 2-3 hours after plating with 5-20 µl of adenoviral vector stock ($\approx 10^{11}$-$10^{12}$ viral particles/ml).

Immunoprecipitation, Immunoblots and Immunofluorescence

Cardiac lysates from 6-12-week-old doxycycline-fed transgenic mice were prepared from either whole hearts or isolated ventricular cardiomyocytes (Yang et al. 2013). Immunoprecipitations were performed in modified RIPA buffer consisting of 50 mM Tris HCl; pH 7.4, 150 mM NaCl, Triton X-100 (0.25%), 10 mM EDTA, 10 mM EGTA, 10 µM Calpain inhibitor I, 10 µM Calpain inhibitor II, and Complete Mini-tablets (1 per 7 ml), using anti-FLAG antibody (Sigma) overnight. Immune complexes were collected using protein A (Amersham) for 2 h, followed by extensive washing. Proteins were size-fractionated, transferred to nitrocellulose membranes and probed with anti-FLAG antibody (Sigma), anti-tubulin antibody (Santa Cruz), custom anti-$\alpha_{1C}$ and anti-$\beta_2$ antibodies (Yang et al. 2013), and phospholamban antibodies (Badrilla). Detection was performed with a CCD camera (Carestream Imaging), and ImageQuant software was used for quantification. Isolated cardiomyocytes were fixed for 15 minutes in 4% paraformaldehyde, and indirect immunofluorescence performed using a 1:200 rabbit anti-FLAG antibody and 1:200 FITC-labeled goat-anti-rabbit antibody (Sigma). Images were acquired using a confocal microscope.

Cellular Electrophysiology

Membrane currents from isolated mouse ventricular cardiomyocytes (O'Connell et al. 2007) were measured by the whole-cell patch-clamp method using a MultiClamp 700B amplifier and pCLAMP 10 software (Molecular Devices) as described (Yang et al. 2013). The pipette solution contained (in mM): 40 CsCl, 90 Cs gluconate, 10 BAPTA, 1 MgCl$_2$, 4 Mg-ATP, 2 CaCl$_2$, and 10 HEPES, adjusted to pH 7.2 with CsOH. After the isolated cardiomyocytes were adequately buffered with 10 mM BAPTA in the internal solution, the isolated cardiomyocytes were superfused with (in mM): 140 TEA-Cl, 1.8 CaCl$_2$, 1 MgCl$_2$, 10 glucose, and 10 HEPES, adjusted to pH 7.4 with CsOH. For experiments in tsA-201 cells, TEA-Cl was reduced to 130 mM, and BaCl$_2$ (10 mM) was used instead of CaCl$_2$. Pipette series resistances were usually <1 MΩ after 60% compensation. Leak currents and capacitance transients were subtracted by a P/4 protocol. Voltages were corrected for the liquid junction potential of −10 mV. To measure Ca$^{2+}$ peak currents, the cell membrane potential was held at −50 mV and stepped to +10 mV for 350 ms every 10 seconds. To evaluate the current-voltage (I-V) relationship for Ca$^{2+}$ currents, the same protocol was repeated with steps between −50 mV to +50 mV in 10 mV increments. All experiments were performed at room temperature, 22±1° C. The parameters of voltage-dependent activation were obtained using a modified Boltzmann distribution: $I(V) = G_{max}*(V-E_{rev})/[1+\exp(V_{mid}-V)/V_c)]$, where I(V) is peak current, $G_{max}$ is maximal conductance, $E_{rev}$ is reversal potential, $V_{mid}$ is the midpoint, and $V_c$ is the slope factor.

Whole-cell recordings of virally-infected cultured guinea pig ventricular myocytes were conducted at room temperature as previously described (Miriyala et al. 2008; Xu et al. 2010). Patch pipettes typically had 1-2 MO series resistance when filled with internal solution containing (in mM): 150 cesium-methanesulfonate, 10 EGTA, 5 CsCl, 1MgCl$_2$, 10 HEPES and 4 MgATP (pH 7.3). Cells were perfused with normal Tyrode external solution during formation of gigaohm seal. After successful break-in to the whole-cell configuration the perfusing medium was switched to an external recording solution containing (in mM): 155 N-methy-D-glucamine-aspartate, 10 4-aminopyridine, 1 MgCl$_2$, 5 BaCl$_2$, 10 HEPES (pH 7.4). Currents were sampled at 50 KHz and filtered at 5 KHz and leak and capacitive currents were subtracted using a P/8 protocol.

Fractional Shortening of Isolated Cardiomyocytes

Freshly isolated myocytes were superfused with a Tyrode's solution containing 1.0 mM CaCl$_2$ and 300 nM nisoldipine. Myocytes were field stimulated at 1-Hz. Percent contraction of sarcomere length was measured using the SarcLen module of Ionoptix and calculated as the difference of shortest sarcomere length during a contraction subtracted from the relaxed sarcomere length, divided by the relaxed sarcomere length, all averaged over at least 8 contractions.

Ex Vivo Cardiac Contractility

The cannulated hearts were retrogradely perfused on a Langendorff system with a modified Krebs solution (118.5 mM NaCl, 25 mM NaHCO$_3$, 4.7 mM KCl, 1.2 mM MgSO$_4$, 1.2 mM KH$_2$PO$_4$, 11 mM glucose, 1.8 mM Ca$^{2+}$). Left ventricular pressure was measured using a balloon catheter connected to an APT-300 pressure transducer, which was connected to a Powerlab digitizer (ADInstruments). After initial assessment of cardiac contractility, 300 nM nisoldipine was perfused to silence endogenous Ca$^{24}$ currents. The effects of nisoldipine on contractility were assessed after at least 3 minutes and upon stabilization of LV pressures. Thereafter, 200 nM isoproterenol was perfused with 300 nM nisoldipine for at least 3 minutes. Peak LV pressure during the 3-minute period was used for the assessment of β-adrenergic agonist stimulation.

Statistics

Results are presented as mean±SEM. For multiple group comparisons, a one-way ANOVA followed by multiple comparison testing were performed. For comparisons between two groups, an unpaired Student's t-test was used.

Statistical analyses were performed using Prism 6 (Graphpad Software). Differences were considered statistically significant at values of P<0.05

Example 5

β-Less $Ca_V1.2$ Channels Traffic to Membrane in Adult Cardiomyocytes

Figure 6B:
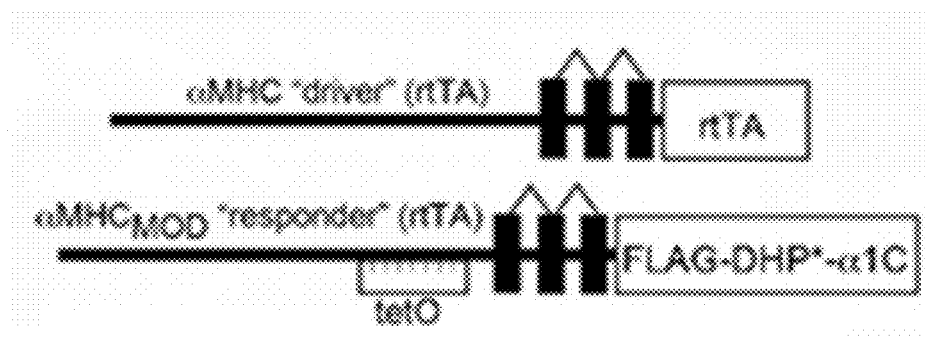
Figure 6C:
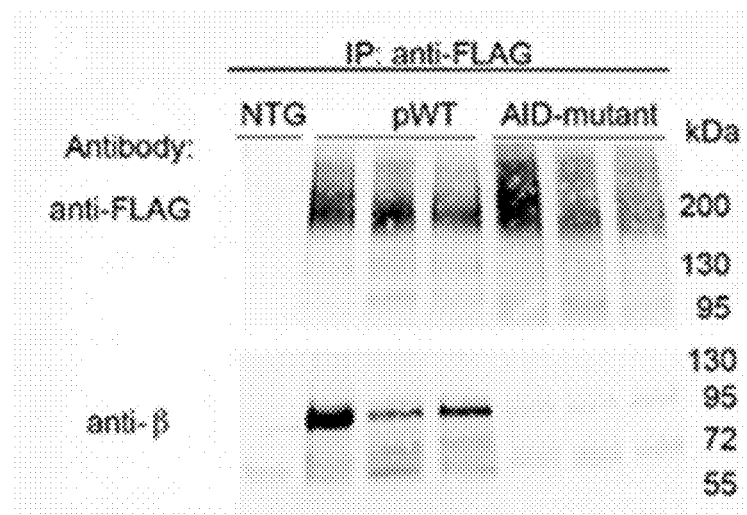

Alanine-substitutions of three conserved residues—Y467, W470 and I471—in rabbit $\alpha_{1C}$ AID (FIG. 6A) increases the $K_d$ of β subunit binding from nM to >6M (Chen et al. 2004; Opatowsky et al. 2004; Van Petegem et al. 2004; Van Petegem et al. 2008). $β_2$ subunits failed to co-precipitate with the AID-mutant $\alpha_{1C}$ when co-expressed with AID-mutant $\alpha_{1C}$ in tsA201 cells (FIG. S1A) confirming the critical importance of this region for β binding. We then created transgenic mice with cardiac-specific and doxycycline-inducible expression of N-terminal 3×FLAG-tagged dihydropyridine (DHP)-resistant (T1066Y/Q1070M) (He et al. 1997; Hockerman et al. 1997) AID-mutant rabbit $\alpha_{1C}$ (FIG. 6B). Controls were provided by transgenic FLAG-tagged DHP-resistant $\alpha_{1C}$ subunits with wild-type AIDs, termed pseudo-wild-type (pWT) $\alpha_{1C}$. Co-immunoprecipitation experiments from transgenic mice hearts confirmed that pWT $\alpha_{1C}$ associates with endogenous β-subunit, but AID-mutant $\alpha_{1C}$ does not (FIG. 6C). The anti-β antibody recognizes all $Ca_Vβ$ subunits, thus ruling out compensation from other P subunits in heart and thus confirming that the AID motif is essential to mediate the high-affinity binding between $\alpha_{1C}$ and $β_2$ in cardiomyocytes.

Figure 6D:
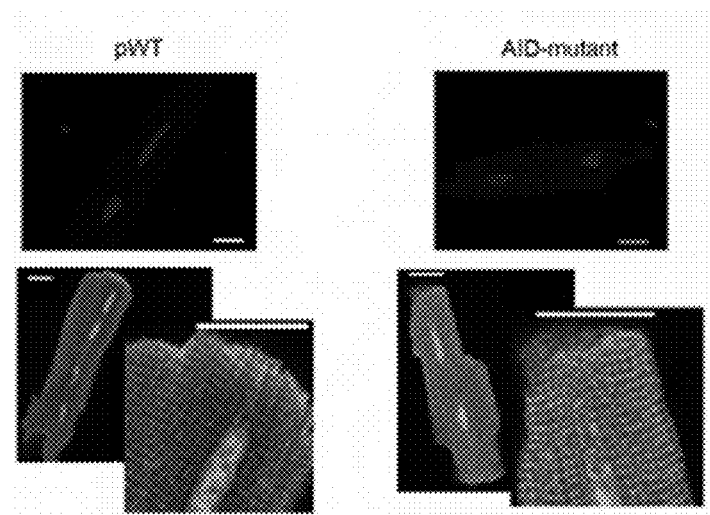
Figure 6E:
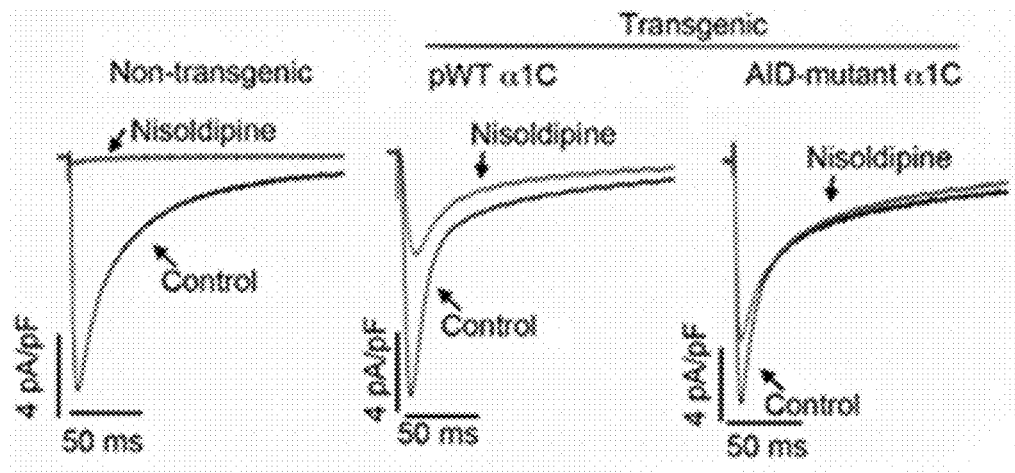
Figure 6F:
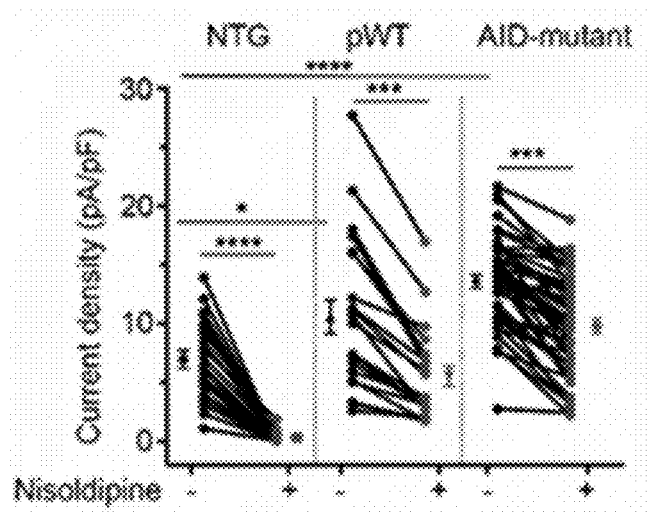
Figure 6G:
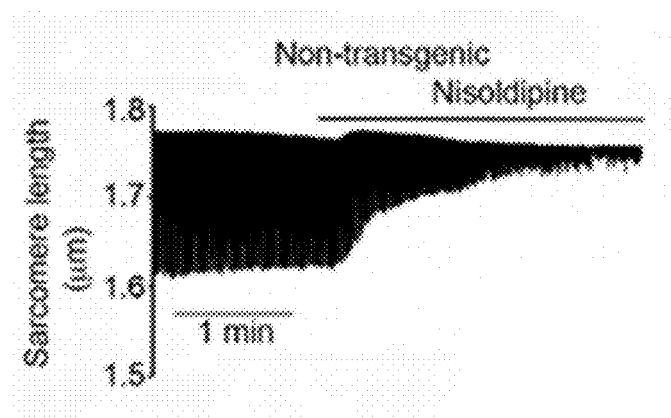
Figure 6H:
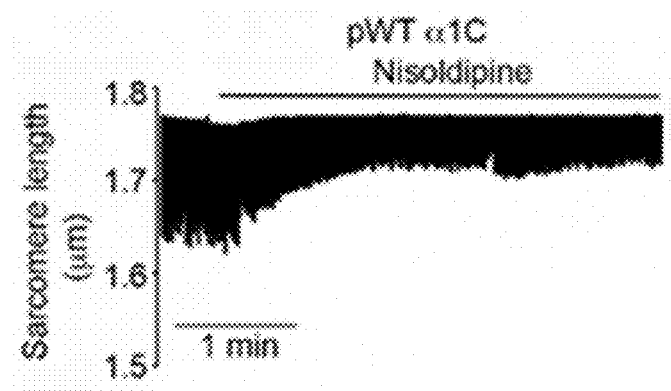
Figure 6I:
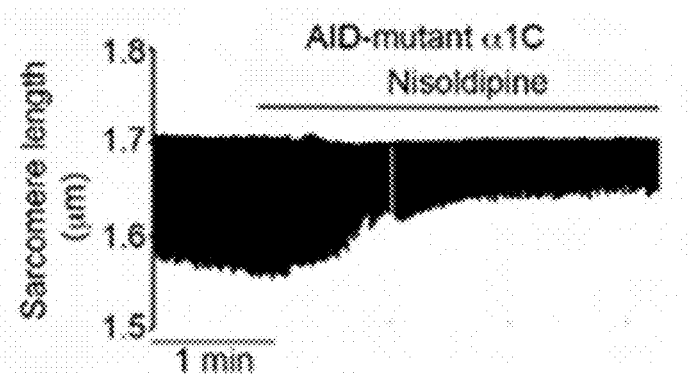
Figure 6J:
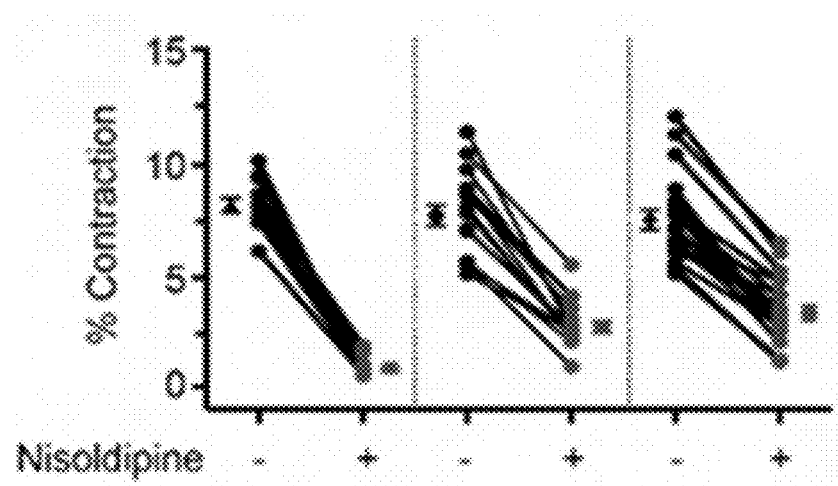

We assessed the impact of loss of β-binding on AID-mutant $\alpha_{1C}$ subcellular localization and functional expression in cardiomyocytes using three complementary approaches. First, immunofluorescence experiments using anti-FLAG antibody on fixed cardiomyocytes indicated that both transgenic pWT $\alpha_{1C}$ and AID-mutant $\alpha_{1C}$ channels displayed a similar striated pattern consistent with surface membrane distribution and localization in t-tubules (FIG. 6D). Second, we exploited the T1066Y/Q1070M mutations that impart relative DHP-resistance (He et al. 1997; Hockerman et al. 1997) to block $Ca^{2+}$ currents from endogenous DHP-sensitive $Ca_V1.2$ with nisoldipine and isolate $Ca^{2+}$ current from transgenic pWT $\alpha_{1C}$ or AID-mutant $\alpha_{1C}$ channels. Compared to cardiomyocytes isolated from NTG control mice, cardiomyocytes isolated from both pWT and AID-mutant $\alpha_{1C}$ transgenic mice had increased peak $Ca^{2+}$ currents, and substantial peak $Ca^{2+}$ currents remaining after exposure to nisoldipine (FIG. 6E and FIG. 6F). Third, field-stimulated contraction of cardiomyocytes isolated from transgenic AID-mutant $\alpha_{1C}$ mice persisted in the presence of 300 nM nisoldipine (FIG. 6I and FIG. 6J), similar to the contraction of cardiomyocytes isolated from NTG (FIG. 6G) and transgenic pWT $\alpha_{1C}$ mice (FIG. 6H). Overall, these results demonstrate that transgenic β-less AID-mutant $\alpha_{1C}$ channels traffic to the sarcolemma and trigger E-C coupling in cardiomyocytes. This is in stark contrast to the necessary role of β-binding for surface trafficking and function of $Ca_V1.2$ channels reconstituted in heterologous cells (FIG. S1A and FIG. S1B), or expressed in hippocampal neurons (Obermair et al. 2010).

We also considered that endogenous WT $\alpha_{1C}$ channels could couple with AID-mutant $\alpha_{1C}$ channels to facilitate trafficking of β-less channels to the surface membranes in cardiomyocytes, which could be basis for the observed differences between cardiomyocytes and heterologous expression systems. To determine whether coupling-induced trafficking could occur, we co-expressed either DHP-resistant pWT $\alpha_{1C}$ or DHP-resistant AID-mutant $\alpha_{1C}$ with both WT $\alpha_{1C}$ and $β_2$ subunits in tsA201. In the presence of nisoldipine, which inhibits the WT $\alpha_{1C}$ channels, tsA201 cells expressing the AID-mutant $\alpha_{1C}$ channels had no remaining $Ca^{2+}$ current (FIG. S1C, right), while cells expressing the DHP-resistant pWT $\alpha_{1C}$ had remaining current (FIG. S1C, left) implying that at least in tsA201 cells, β-less channels were unable to "hitchhike" to the membrane with WT channels.

Example 6

Figure 7A:
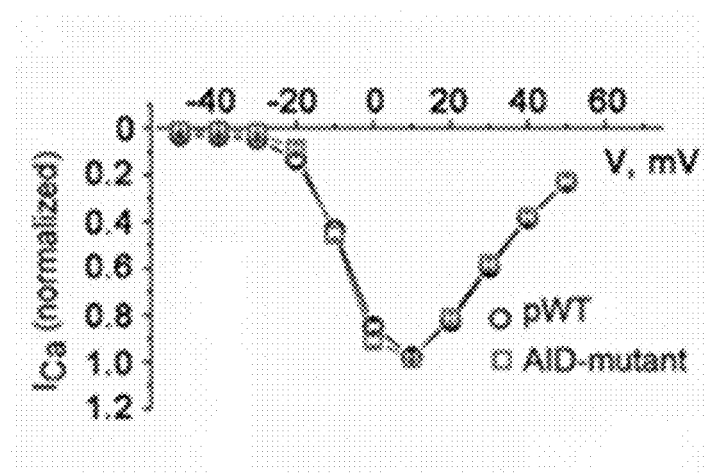
FIGS. 7A-7J show that AID-mutant $Ca_V1.2$ channels lack β-adrenergic regulation.
Figure 7B:
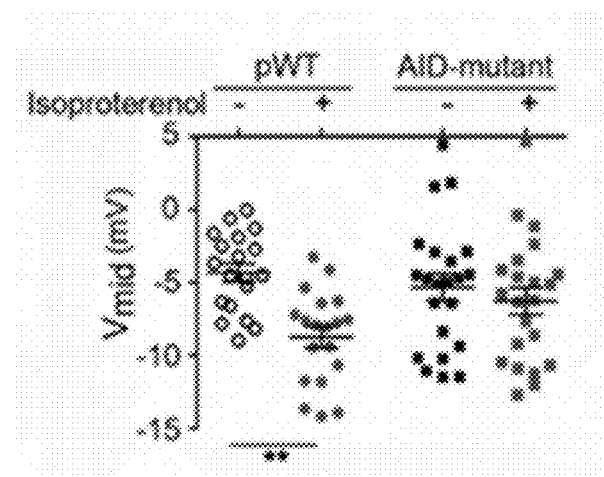
Figure 7C:
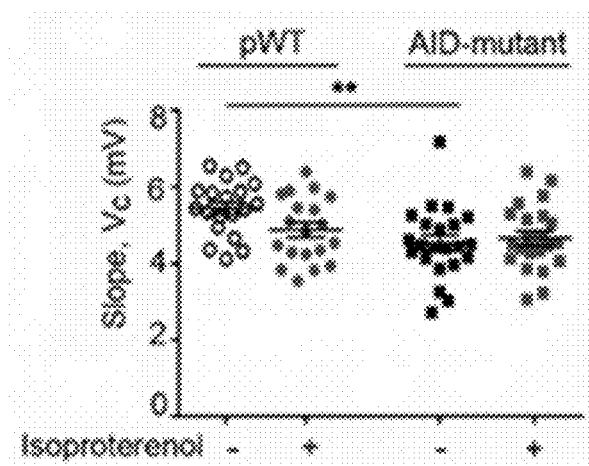
Figure 7D:
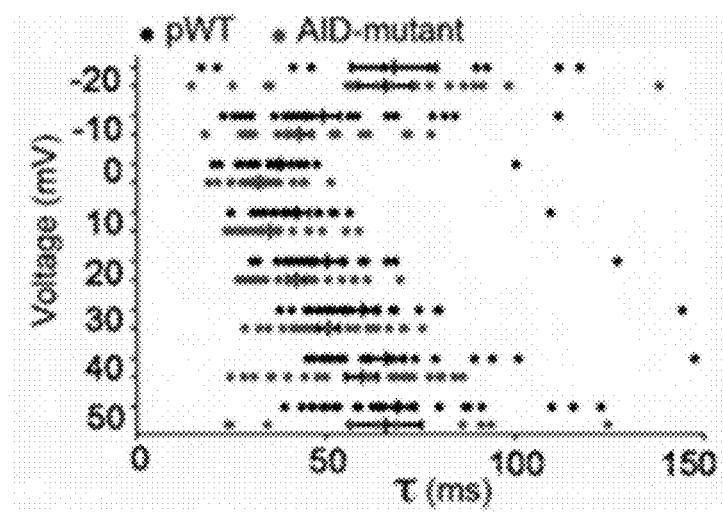
Figure 7E:
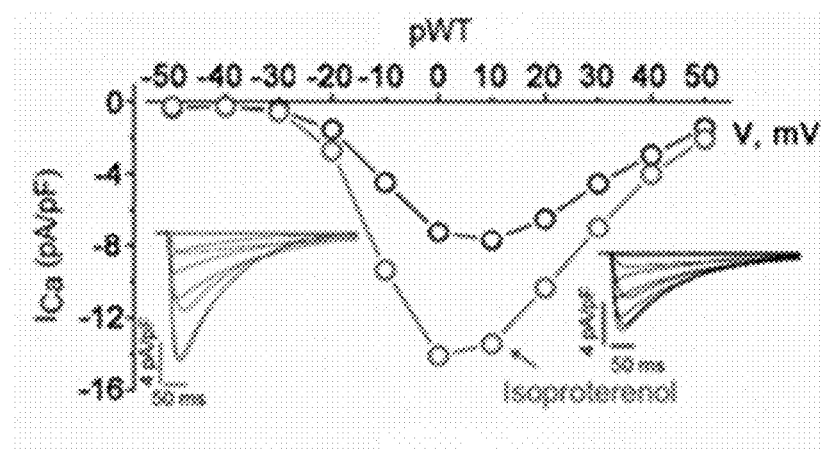
Figure 7F:
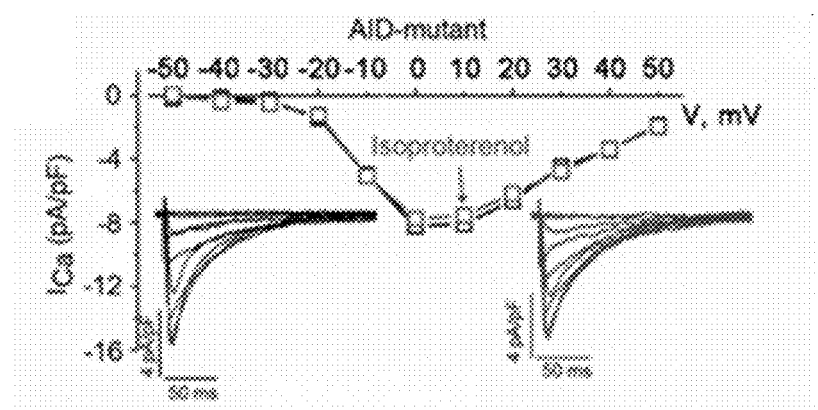
Figure 7G:
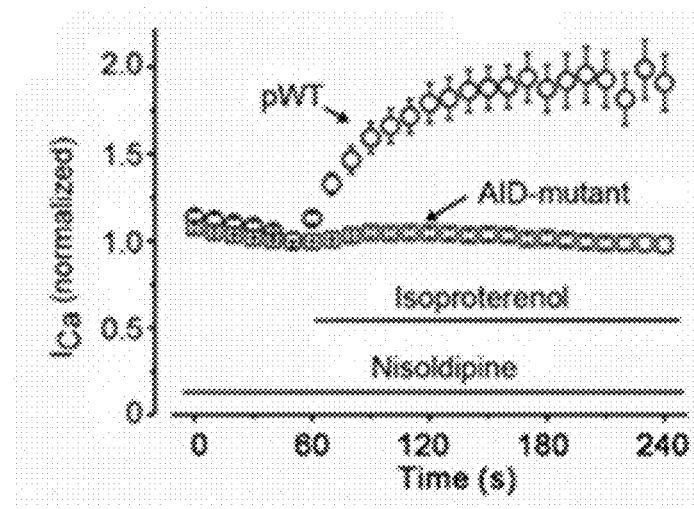

PKA modulation of $Ca_V1.2$ channels Is dependent upon $\alpha_{1C}$-β Interactions In heterologous expression studies, 13 subunits not only enable $\alpha_{1C}$ surface trafficking, but also can differentially induce, depending upon 13 subunit isoform, a hyperpolarizing shift in the voltage-dependence of $Ca_V1.2$ activation and increase the channel open probability ($P_o$) (Dolphin 2003; Miriyala et al. 2008). We assessed the biophysical properties of the transgenic β-less AID-mutant $\alpha_{1C}$ channels compared to transgenic pWT $Ca^{2+}$ channels. Surprisingly, normalized current-voltage (I-V) relationships of nisoldipine-resistant transgenic pWT and AID-mutant $\alpha_{1C}$ channels were remarkably similar (FIG. 7A). The mid-point potentials and slope factors for steady-state activation, derived from a Boltzmann function, demonstrated relatively small shifts for the AID-mutant channels compared to control pWT channels (FIG. 7B and FIG. 7C). Furthermore, the inactivation kinetics of nisoldipine-resistant $Ca^{24}$ currents were not significantly different at any test potential between cardiomyocytes isolated from pWT and AID-mutant $\alpha_{1C}$, respectively (FIG. 7D). Therefore, in adult cardiomyocytes, $Ca_V1.2$ channels comprised of transgenic β-less $\alpha_{1C}$ have similar voltage-dependence of activation and inactivation kinetics as transgenic pWT $Ca_V1.2$ channels.

Figure 7H:
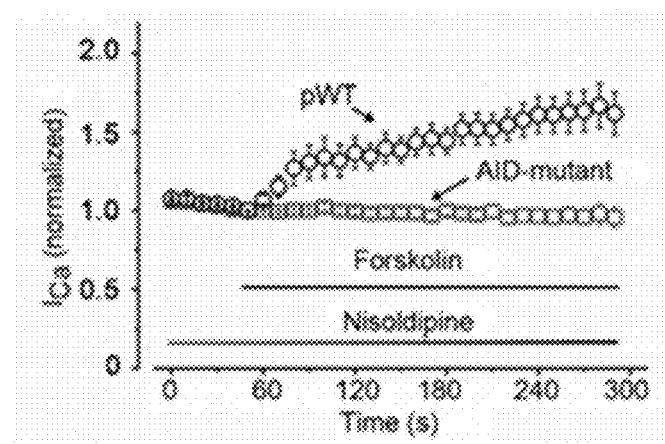
Figure 7I:
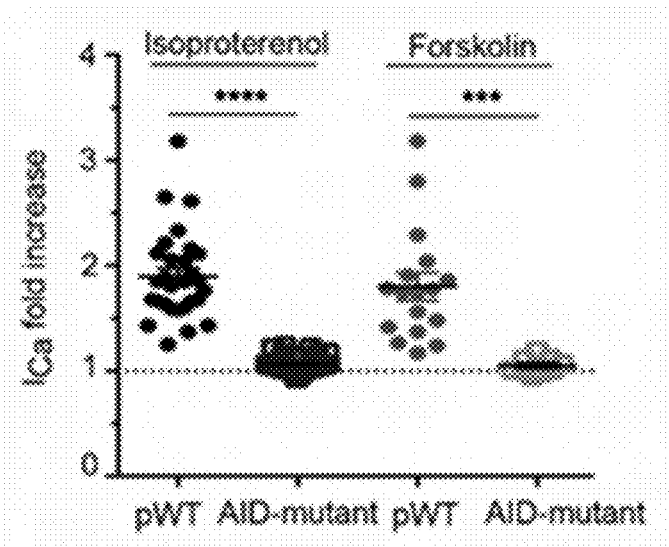
Figure 7J:
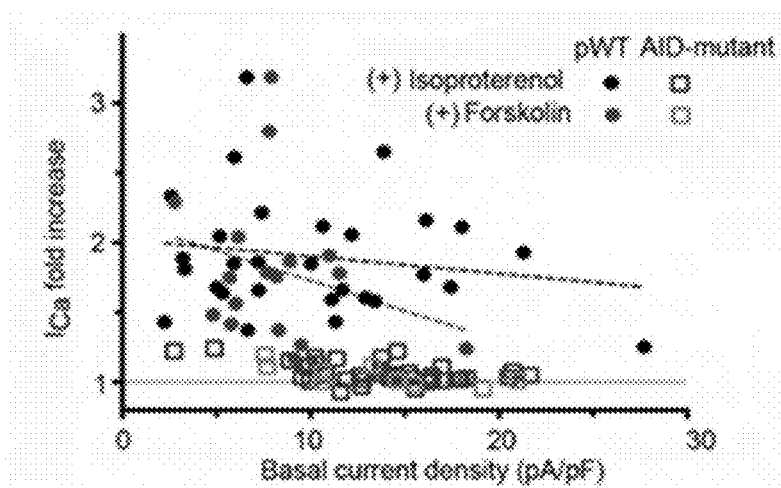
Figure 8A:
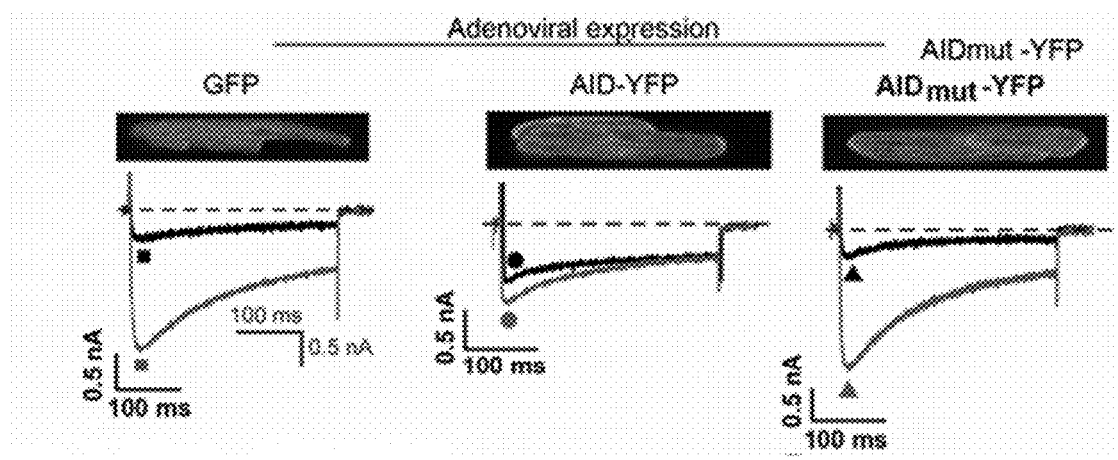
FIGS. 8A-8F show that β-less wild-type endogenous CaV1.2 channels are not stimulated by PKA.
Figure 8B:
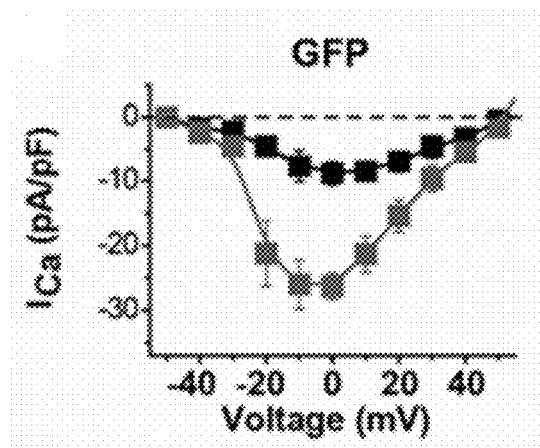
Figure 8C:
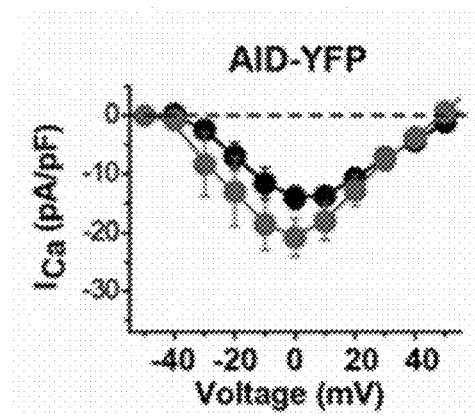
Figure 8D:
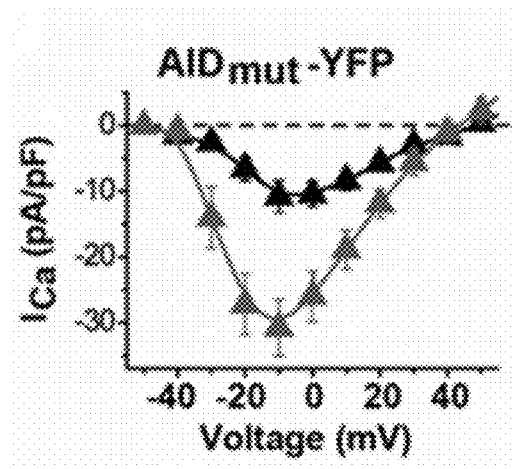
Figure 8E:
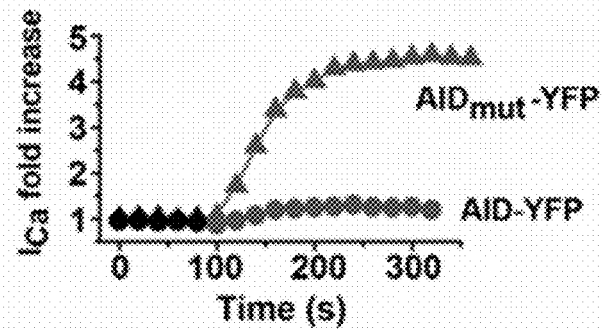
Figure 8F:
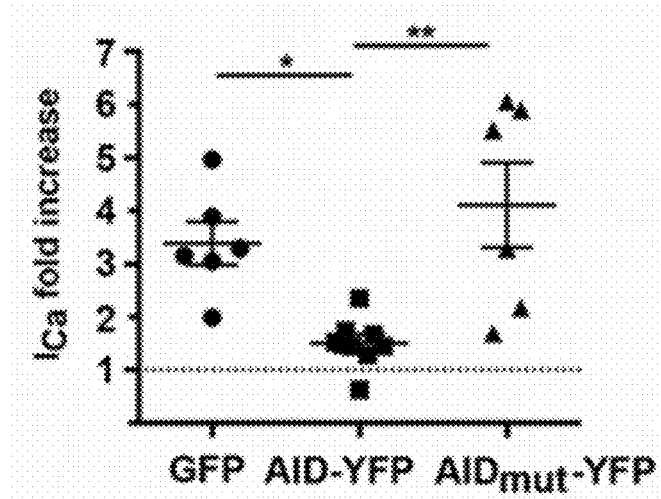

We next determined the sensitivity of $Ca_V1.2$ channels containing either transgenic pWT $\alpha_{1C}$ or AID-mutant $\alpha_{1C}$ to PKA modulation. In cardiomyocytes isolated from mice expressing transgenic pWT $\alpha_{1C}$, 200 nM isoproterenol increased the nisoldipine-insensitive current by a mean of 1.9±0.1-fold (FIGS. 7E and 7G-7J), and shifted the $V_mt$ in the hyperpolarizing direction by a mean of 4.4 mV (FIG. 78). Similarly, forskolin, which directly activates adenylyl cyclase thereby bypassing 3-adrenergic receptors, increased transgenic pWT $\alpha_{1C}$ $Ca^{2+}$ currents by 1.8+0.1-fold (FIGS. 7H-7J). In sharp contrast, $Ca^{2+}$ currents through transgenic AID-mutant $\alpha_{1C}$ $Ca_V1.2$ channels were insensitive to either isoproterenol (FIGS. 7B, 7F, 7G, 7I-7J) or forskolin (FIGS. 7H-7J). In cardiomyocytes, there is an inverse relationship between total peak current and isoproterenol-induced or forskolin-induced fold increase in $Ca^{2+}$ current (Mirlyala et al. 2008). In cardiomyocytes isolated from transgenic pWT $\alpha_{1C}$ mice, we observed an inverse relationship between basal current density and isoproterenol or forskolin-induced increase in $Ca^{2+}$ current (FIG. 7J). For the transgenic AID-mutant β-less channels, however, activation of PKA by either forskolin or isoproterenol had no effect on $Ca^{2+}$ current, regardless of basal $Ca^{2+}$ current density (FIG. 7J).

To address whether the YWI/AAA mutations themselves produced an intrinsic insensitivity of the channel to PKA modulation, we sought to engender conditions under which there would be a predominance of β-less endogenous $Ca_V1.2$ channels in isolated cardiomyocytes. We achieved this by using adenovirus to over-express a YFP-tagged 18-residue AID peptide derived from $\alpha_{1C}$ I-II loop (or a mutant YWI/

AAA peptide as a control) in cultured adult guinea pig ventricular cardiomyocytes. We reasoned this intervention would serves as a sponge for endogenous β subunits, leaving a majority of endogenous $Ca_V1.2$ channels devoid of β. In control cells expressing either GFP or YFP-tagged mutant (YWI/AAA) AID peptide incapable of binding β, 1 μM forskolin resulted in a robust 4- to 5-fold increase in whole-cell current amplitude (FIGS. 8A, 8B, 8D-8F). By contrast, this response was sharply curtailed in cardiomyocytes over-expressing YFP-AID peptide (FIGS. 8B, 8C, 8E-8F). Hence, β-less wild-type $α_{1C}$ channels also demonstrate a marked insensitivity to PKA modulation.

We also considered two trivial explanations that could potentially account for the insensitivity of AID-mutant $α_{1C}$ to PKA stimulation: 1) these channels were already phosphorylated by PKA under basal conditions; 2) the β-adrenergic signaling pathway was compromised in cardiomyocytes from AID-mutant $α_{1C}$ transgenic mice. To address whether transgenic AID-mutant $α_{1C}$ channels were basally PKA-phosphorylated, we used a cell-permeable cAMP-PKA inhibitor (Rp-8-Br-cAMPS), which functions by occupying cAMP binding sites thereby preventing activation of PKA holoenzyme. Rp-8-Br-cAMPS reverses isoproterenol-mediated up-regulation of endogenous $Ca_V1.2$ by ~96% (Katchman et al. 2017). In transgenic AID-mutant mice cardiomyocytes, Rp-8-Br-cAMPS did not inhibit nisoldipine-resistant basal current (FIG. S2A), ruling out the idea that AID-mutant $α_{1C}$ channels were basally PKA-phosphorylated. The integrity of the β-adrenergic pathway in transgenic AID-mutant mice cardiomyocytes was assessed by probing whether isoproterenol application led to phosphorylation of phospholamban, a well-known PKA target in heart (Colyer 1998). Western blotting indicated that phospholamban was appropriately phosphorylated at $Ser^{16}$ in response to isoproterenol (FIG. S2B), confirming that the β-adrenergic signaling pathway was intact in AID-mutant transgenic mice cardiomyocytes.

Example 7

β-Adrenergic Regulation of $Ca_V1.2$ does not Require PKA Phosphorylation of 1 Subunits The simplest explanation for the necessary role of $α_{1C}$-0 interaction in PKA modulation of $Ca_V1.2$ is that the β-subunit contains phosphorylation site(s) that are vital to this regulation. Indeed, two phosphorylation sites on $β_2$ C-terminus ($Ser^{512}$ and $Ser^{57}$) were previously identified and proposed to play a role in PKA modulation of $Ca_V1.2$ (Gerhardstein et al. 1999). However, a knock-in mouse expressing $α_2$-subunit truncated after $Pro^{501}$ displayed normal PKA modulation of $Ca_V1.2$, thus ruling out Involvement of any putative C-terminal phosphorylation sites (Brandmayr et al. 2012). Nevertheless, it remained possible that previously unappreciated phosphorylation sites N-terminal to $Pro^{501}$ could mediate the increased $Ca_V1.2$ channel activity in response to activated PKA. Using both manual sequence analyses and several web-based PKA phosphorylation prediction tools (Neuberger et al. 2007; Iakoucheva et al. 2004; Zhou et al. 2004; Blom et al. 1999; Obenauer et al. 2003), we identified 18 conserved consensus PKA phosphorylation sites in the N-terminus, SH3 and GK domains of human $β_{2b}$ (residues labeled red in FIG. S3). We mutated all 18 Ser/Thr residues to Ala in human $β_{2b}$, and generated transgenic mice with inducible cardiomyocyte-specific expression of either GFP-tagged WT or 18-mutant $β_{2b}$ subunits using the same bitransgenic system as in FIG. 6B.

Figure 9A:
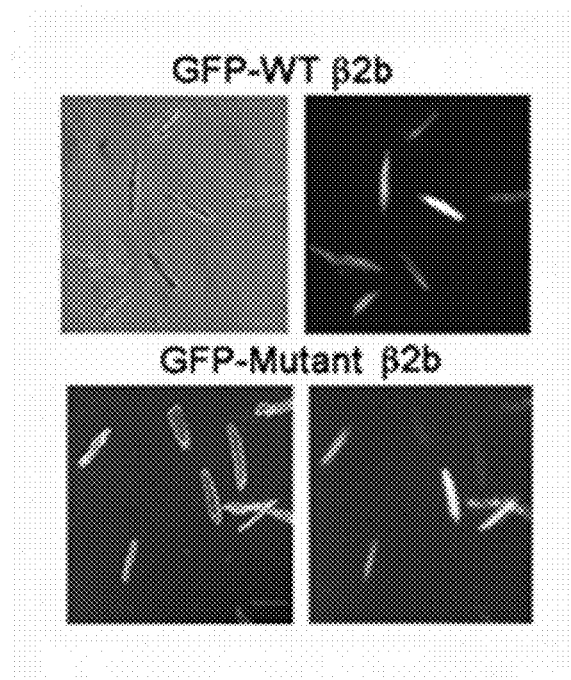
FIGS. 9A-9G show that PKA phosphorylation of $Ca_V\beta$ is not required for β-adrenergic regulation of $Ca_V1.2$.
Figure 9B:
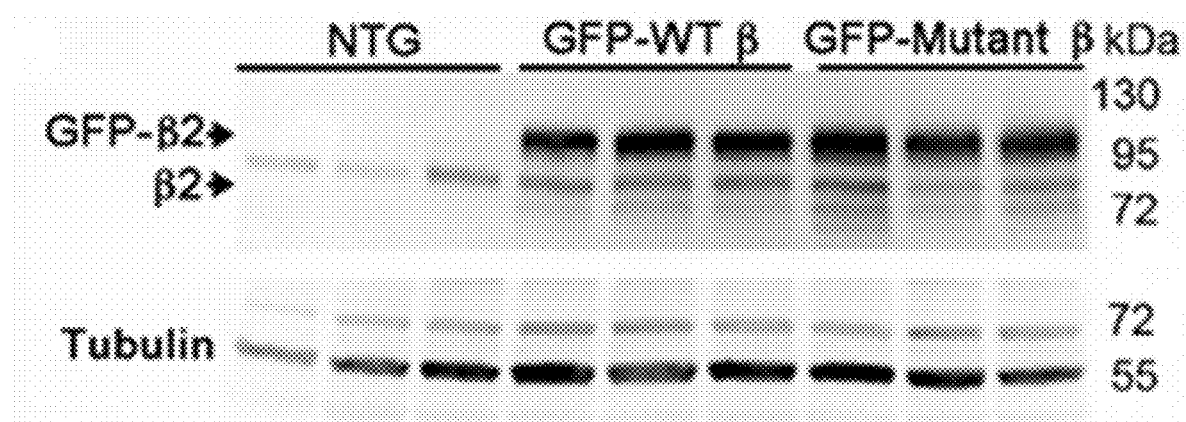
Figure 9C:
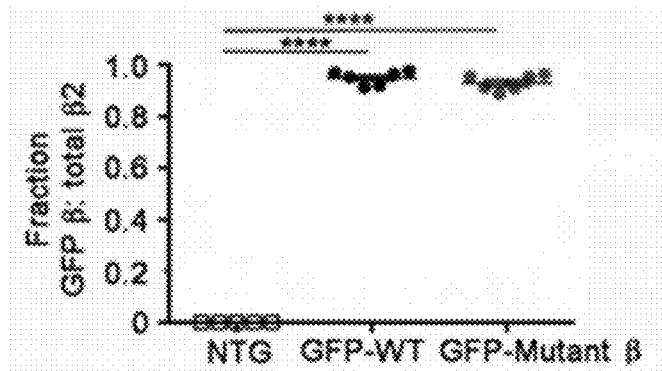
Figure 9D:
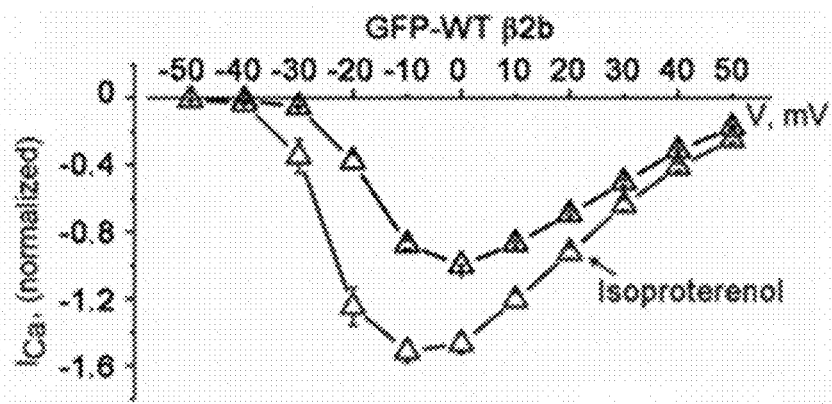
Figure 9E:
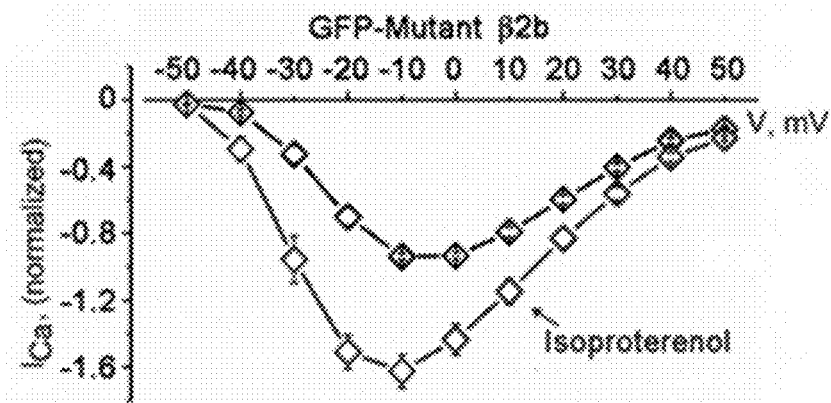
Figure 9F:
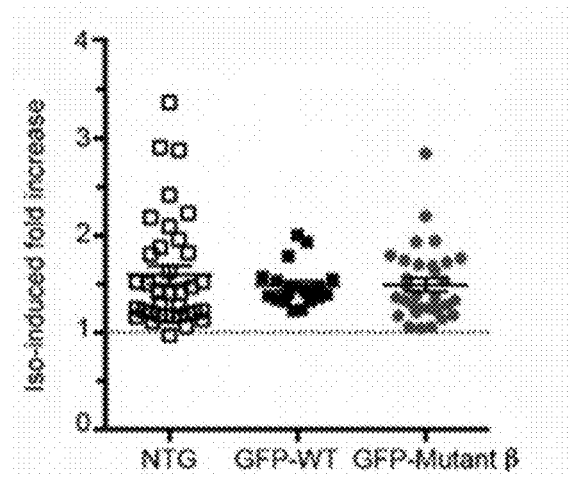

The WT and mutant $β_{2b}$ transgenic mice were fed doxycycline for 1 week, thus ensuring high levels of expression of the GFP-tagged $β_2$ subunits (FIG. 9A). We exploited the larger size of GFP-tagged $β_2$ subunits compared to endogenous β to determine relative expression of transgenic and native $β_2$ subunits (FIG. 9B). Western blot indicated that in cardiomyocytes from transgenic mice, both GFP-$β_2$ and GFP-mutant-$β_2$ were markedly over-expressed (~9:1) compared to endogenous $β_2$ (FIG. 9C). Isoproterenol increased peak $Ca_V1.2$ current by a mean of 1.5±0.1-fold in GFP-WT $β_2$ expressing cells and 1.6±0.1-fold in GFP-mutant $β_2$ expressing cells, respectively, similar to non-transgenic mice (FIGS. 9D-9G). For both GFP-WT and GFP-mutant $β_{2b}$ $Ca^{2+}$ channels, isoproterenol shifted the $V_{mid}$ of steady-state activation by −7.0 mV and −7.5 mV, respectively. These data indicate that, although the $α_{1C}$-$β_2$ interaction is necessary for β-adrenergic regulation of $Ca_V1.2$, direct PKA phosphorylation of $β_2$ is not involved.

Figure 10A:
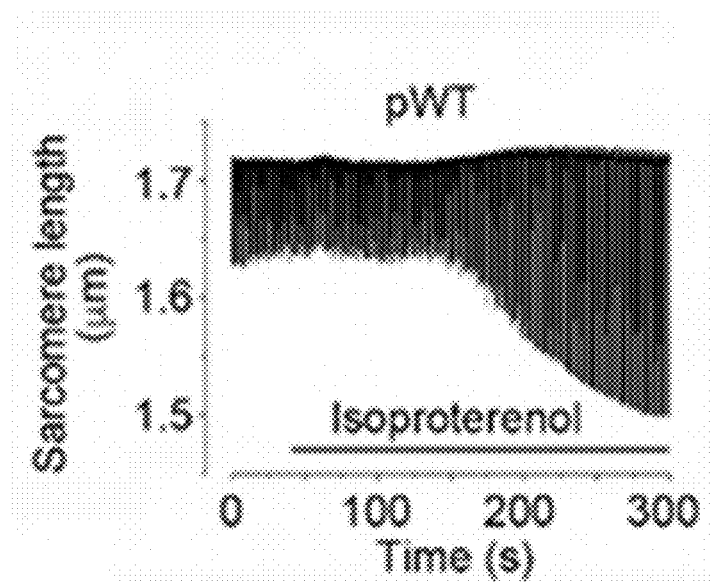
FIGS. 10A-10I show that attenuated β-adrenergic stimulated inotropy in AID-mutant $\alpha_{1C}$ transgenic mice.
Figure 10B:
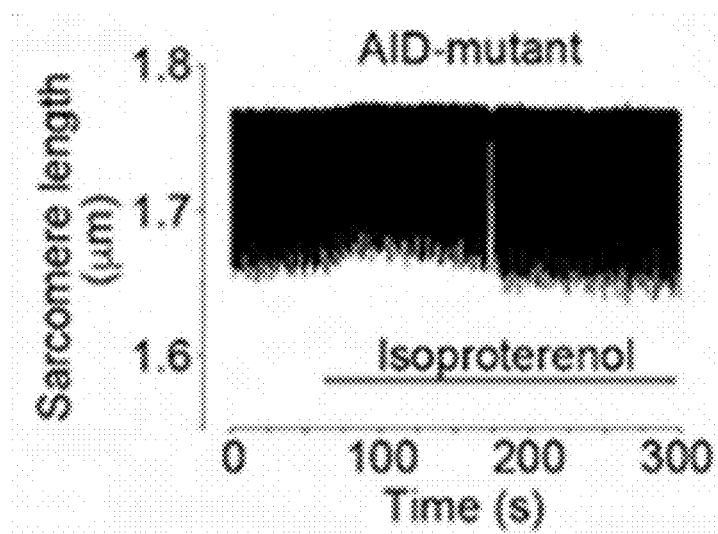
Figure 10C:
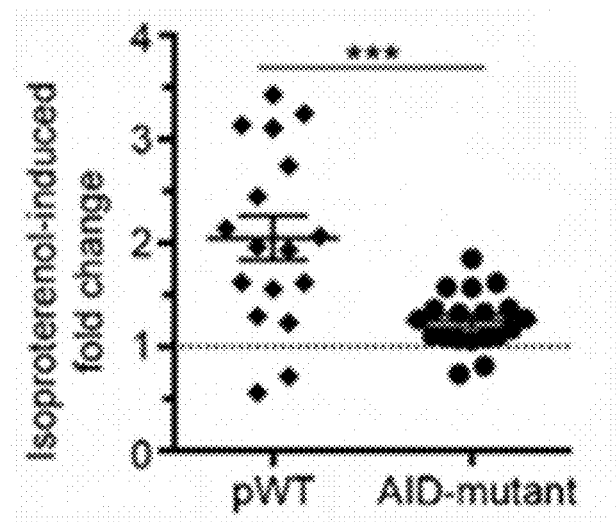
Figure 10D:
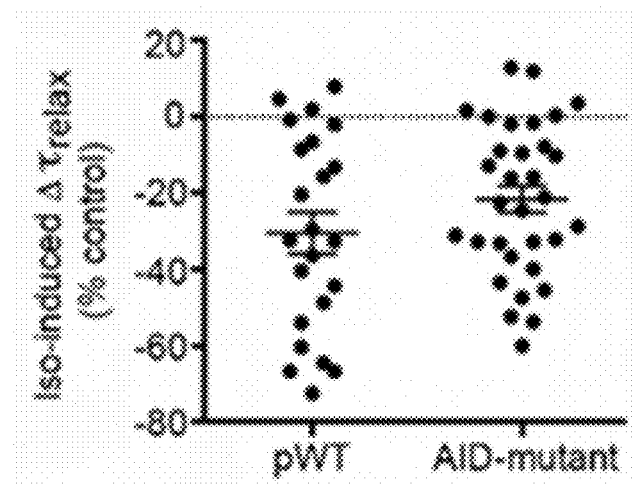

Example 8

β-Adrenergic Regulation of Cardiac Contractility Requires PKA Regulation of $Ca_V1.2$ We next exploited the findings that transgenic β-less AID-mutant $α_{1C}$ channels are insensitive to PKA modulation to probe the specific role of $Ca_V1.2$ modulation in the positive inotropic effect of β-adrenergic agonists in both isolated cardiomyocytes and in the whole heart. In transgenic pWT $α_{1C}$ cardiomyocytes, with endogenous $Ca_V1.2$ channels silenced with nisoldipine, isoproterenol produced a robust 100% increase in fractional shortening (FIG. 10A and FIG. 10C). By contrast, this response was severely diminished in cardiomyocytes expressing transgenic β-less AID-mutant $α_{1C}$ channels in which isoproterenol produced a relatively meager 25% increase in fractional shortening (FIG. 10B and FIG. 10C). Consistent with the effects of isoproterenol on phospholamban phosphorylation (FIG. S2B), isoproterenol enhanced relaxation in cardiomyocytes isolated from both pWT and AID-mutant $α_{1C}$ transgenic mice (FIG. 10D).

Figure 10E:
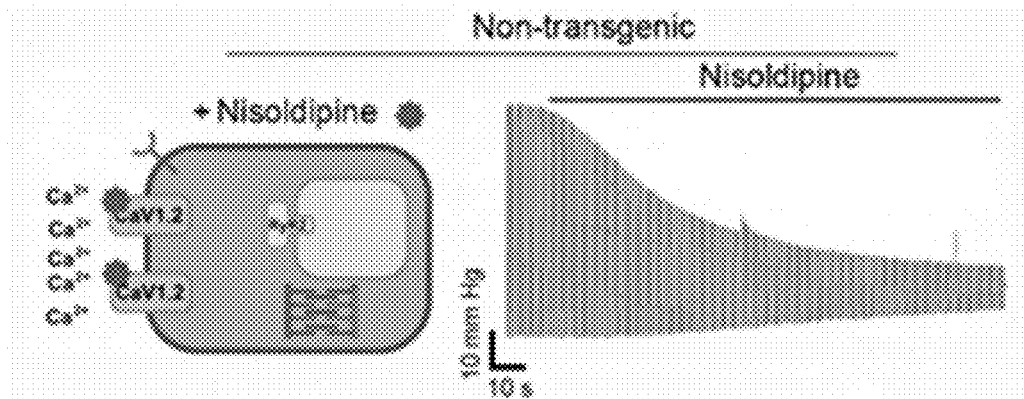
Figure 10F:
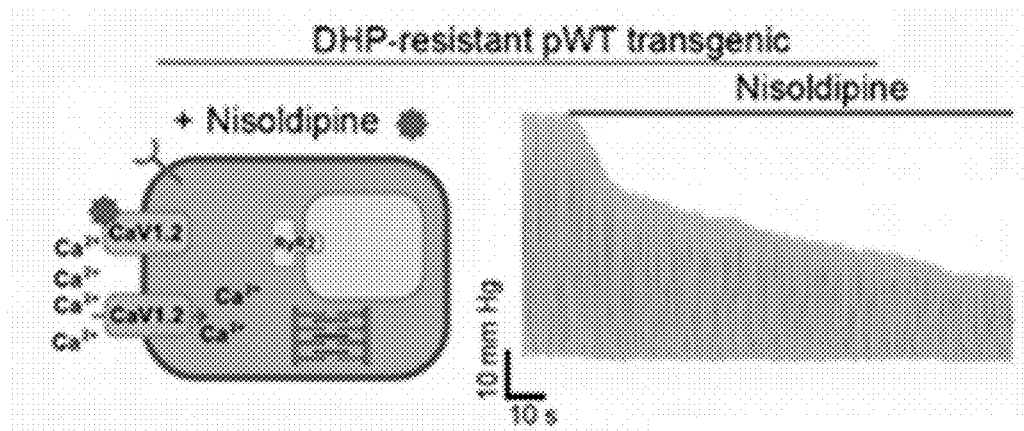
Figure 10G:
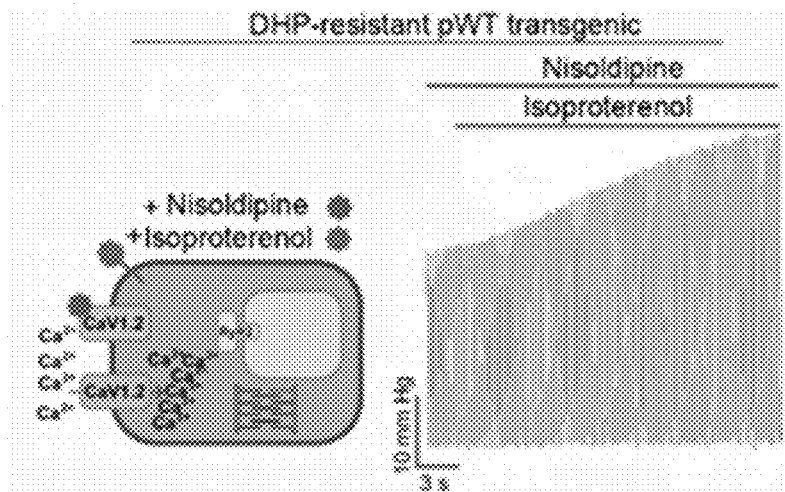
Figure 10H:
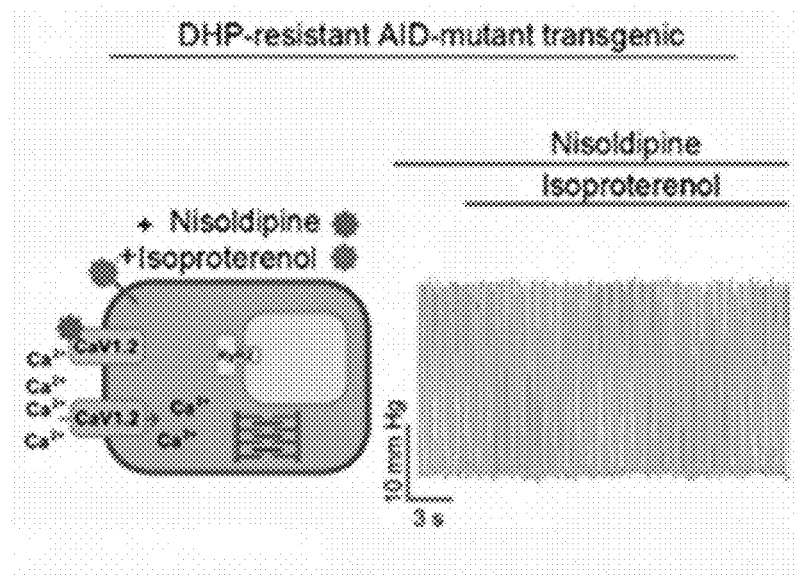
Figure 10I:
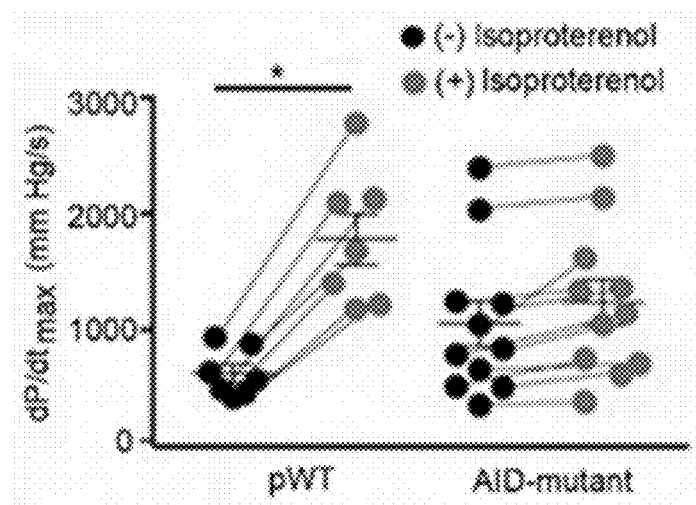

We then assessed the role of $Ca_V1.2$ modulation in β-adrenergic agonist-induced positive inotropy at the whole organ level by inserting a pressure-transduced balloon into the left ventricle of Langendorff-perfused transgenic mice hearts. This approach enabled measurement of cardiac contractility independent of vascular or systemic effects. Hearts were paced at 400 beats per minute to remove the potentially confounding effect of heart rate variability on contractility (Kushnir et al. 2014). After baseline measurements, 300 nM nisoldipine was infused into the coronary arteries via the aorta to suppress endogenous $Ca_V1.2$ channel currents. In hearts from non-transgenic mice, nisoldipine markedly reduced basal cardiac contractility due to the block of endogenous $Ca_V1.2$ channels (FIG. 10E). In pWT $α_{1C}$ hearts, infusion of nisoldipine yielded a comparatively weaker effect on basal contractility owing to the expression of DHP-resistant $Ca^{2+}$ channels (FIG. 10F); a further infusion of 200 nM isoproterenol strongly increased cardiac contractility by 3.3-fold (FIG. 10G and FIG. 10I). By contrast, using the same experimental paradigm in hearts from β-less AID-mutant transgenic mice, the response to isoproterenol was nearly abolished, yielding an average increase in cardiac contractility of only 1.2-fold (FIG. 10H and FIG. 10I).

Example 9

Discussion

Figure 9G:
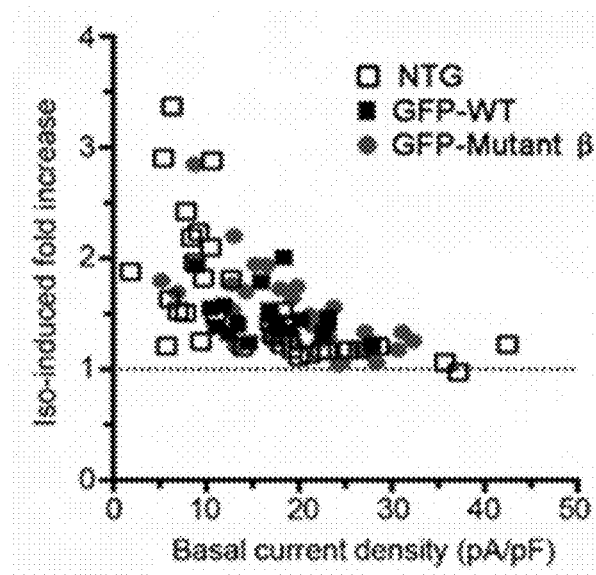

Much of our current understanding regarding mechanisms underlying $Ca_V1.2$ trafficking and modulation derives from studies on recombinant channels reconstituted in heterologous cells. These cells lack the complex cytoarchitecture and intracellular milieu of adult cardiomyocytes. Recently, we have developed an approach that utilizes transgenic mice expressing doxycycline-inducible, cardiac-specific DHP-resistant $\alpha_{1C}$. Compared to knock-in mice models (Domes et al. 2011; Fu et al. 2011), this approach is both cost-effective and rapid, and perhaps more importantly, enables us to induce brief expression of mutant channels in adults, permitting the comparison of WT and mutant $\alpha_{1C}$ structure-function mechanisms in the absence of developmental abnormalities and heart failure. The titration of the level of $Ca_V1.2$ expression is important, as the magnitude of $\beta$-adrenergic stimulation of $Ca_V1.2$ is reduced with increased basal current density (Miriyala et al. 2008; Muth et al. 1999; Beetz et al. 2009; Tang et al. 2010; Chen et al. 2005; Chen et al. 2011). Stratifying the magnitude of $\beta$-adrenergic-mediated upregulation of $Ca_V1.2$ current by total basal current density attenuates this confounding variable (FIG. 7J and FIG. 9G).

Overall, we show that in cardiomyocytes, the AID-motif is required for the high affinity interaction between $\alpha_{1C}$ and $\beta$ subunits, and that $\beta$-less $Ca_V1.2$ channels traffic to the dyad and produce currents that mediate normal E-C coupling. The AID-mutant $\beta$-less $Ca^{2+}$ currents were completely refractory to PKA activation. These findings, combined with our recent studies (Katchman et al. 2017), fundamentally recast our views on mechanisms underlying $Ca_V1.2$ trafficking and PKA modulation in cardiomyocytes as they show that: 1) it is possible for $\beta$-less channels to traffic to the cell surface, 2) $\beta_2$ binding to $\alpha_{1C}$ is indispensable for PKA modulation of $Ca_V1.2$, and that $\beta$-adrenergic regulation of $Ca_V1.2$ can be specifically attenuated by sequestering $\beta$ subunits, 3) conserved consensus PKA phosphorylation sites in $\alpha_{1C}$ (Katchman et al. 2017) and $\beta_b$ are not required for $\beta$-adrenergic regulation of $Ca_V1.2$ in heart. Further, we directly show that $\beta$-adrenergic modulation of $Ca_V1.2$ is critical for sympathetic augmentation of cardiac inotropy, which is essential for the fight-or-flight response.

When co-expressed with a, subunits in heterologous expression systems such as *Xenopus* oocytes or HEK cells, p subunits markedly augment current density by increasing membrane targeting and altering electrophysiological properties (Perez-Reyes et al. 1992; Castellano et al. 1993; Lacerda et al. 1991). In adult heart, however, $Ca^{2Z}$ channels can traffic to the surface membrane without binding to $\beta$. How $\beta$-less $\alpha_{1C}$ channels traffic to the dyad in cardiomyocytes but not in a less complex system such as HEK cells is not yet clear. Although low affinity interactions between heterologously expressed $\beta$ subunit GK and SH3 domains and the $Ca_V2.1$ $\alpha$ subunit in oocytes have been described (Maltez et al. 2005), these potential interactions do not appear to be sufficient to rescue the trafficking of AID-mutant $Ca_V1.2$ channels in tsA-201 cells. Moreover, conditional knockout of Cacnb2 in adult cardiomyocytes caused only a 29% reduction in current density (Meissner et al. 2011).

Regardless of the mechanisms enabling trafficking to the cell surface, $\beta$-less $Ca_V1.2$ channels are functionally normal under basal conditions in adult cardiomyocytes. However, the $\beta$-less channels cannot be regulated by adrenergic-PKA stimulation, although the $\beta$ subunit does not appear to be the functional target of PKA. To differentiate between the lack of $\beta$ binding as opposed to the mutations in the AID as causative of the defect in $\beta$-adrenergic regulation of $Ca_V1.2$, we used the complementary approach of expressing using adenovirus, YFP-AID- and YFP-mutant AID-containing peptides in cultured adult guinea pig ventricular myocytes. The response to forskolin was markedly reduced by preventing $\beta$ subunits from interacting with endogenous wild-type $\alpha_{1C}$, implying that lack of $\beta$ binding to $\alpha_{1C}$ is sufficient to prevent $\beta$-adrenergic regulation of $Ca_V1.2$ in the heart. Our studies cannot address where and when $\beta$ subunits first interact with $\alpha_{1C}$ subunits in the heart.

Identifying the functional PKA target is more complicated. It is likely not solely $\alpha_{1C}$, based upon our prior studies eliminating all conserved consensus PKA phosphorylation sites in the $\alpha_{1C}$ subunit (Katchman et al. 2017). Likewise, it is not solely $\beta$, based upon eliminating all conserved PKA phosphorylation sites in $\beta_2$ (FIGS. 9A-9G). Thus, our findings suggest that either there is redundancy between $\alpha_{1C}$ and $\beta$ subunits, such that PKA phosphorylation of either subunit is sufficient to mediate adrenergic regulation of $Ca^{2+}$ channels in the heart, or that PKA phosphorylation of the core $Ca_V1.2$ subunits, $\alpha_{1C}$ and $\beta$, are not necessary for $\beta$-adrenergic regulation of the $Ca^{2+}$ influx in the heart. This can be addressed by cross-breeding the transgenic mice harboring Ala-substitutions of all PKA consensus sites in $\alpha_{1C}$ and $\beta_2b$. Although PKA phosphorylation of $\beta$ is not required, $\beta$ subunits, via binding to the I-II loop, could regulate pore opening and voltage-sensor movement. The domain I S6-AID linker forms a continuous helix that may act as a rigid rod through which $\beta$ subunits modulate channel gating (Findeisen and Minor 2009).

The loss of $\beta$-adrenergic activation of $Ca_V1.2$ correlated with a markedly attenuated $\beta$-adrenergic contractile response. Originally proposed by Fabiato, $Ca_V1.2$ current has two distinct roles in E-C coupling: triggering the release of $Ca^{2+}$ from the SR and loading the cell (and SR) with $Ca^{2+}$ (Fabiato 1985). The loss of adrenergic regulation of $Ca_V1.2$ could affect both triggering of RyR2 and the loading of SR with $Ca^{2+}$, thereby attenuating the adrenergically-driven inotropic response. Our findings are the first to demonstrate experimentally the vital role of $\beta$-adrenergic stimulation of $Ca_V1.2$ in shaping the flight-or-fight response in the heart, and validate a recently proposed mathematical model predicting that the loss of $\beta$-adrenergic stimulation of $Ca_V1.2$ would markedly limited $Ca^{2+}$ transients and contraction (Negroni et al. 2015). PKA and $Ca^{2+}$/calmodulin-dependent protein kinase II (CaMKII) phosphorylation of RyR2 also enhances the open probability of the RyR2 $Ca^{2+}$ release channels in the SR by enhancing their sensitivity to cytosolic (Aalkjaer and Nilsson 2005) and synchronizing SR $Ca^{2+}$ release (Kushnir et al. 2010; Marx et al. 2000; Wehrens et al. 2004). It remains controversial, however, as to whether increasing the open probability of RyR2 is critically important for inotropic responses in the heart (Shan et al. 2010; Muraski et al. 2008; Eisner et al. 2009). We demonstrate that without augmented $Ca_V1.2$ current to load the cell with additional $Ca^{2+}$ and/or enhance RyR opening via $Ca^{2+}$-induced $Ca^{2+}$ release, $\beta$-adrenergic agonist-induced phosphorylation of RyR2 and phospholamban does not result in substantial $\beta$-adrenergic augmentation of cardiac contractility.

In summary, we have found that $Ca^{2+}$ channel $\beta$ subunit binding to the pore-forming $\alpha_{1C}$ subunit is not required for trafficking and function of the $Ca^{2+}$ channel in the heart. The loss of $\alpha_{1C}$-$\beta_2$ binding causes marked attenuation of β-adrenergic induced stimulation of $Ca_v1.2$ and inotropy. Thus, we identify a new function for β subunits in heart: as an essential component of the PKA-mediated augmentation of $Ca_v1.2$ and increased cardiac contractility that occurs during the physiological fight or flight response.

Appendices 1 and 2 are attached hereto which provide additional details regarding the inventive principles described in this disclosure. Appendices 1 and 2 are each expressly incorporated herein by reference in their entirety. In the event of a conflict between the teachings of this application and those of the incorporated appendices, the teachings of this application control.

The embodiments described in this disclosure can be combined in various ways. Any aspect or feature that is described for one embodiment can be incorporated into any other embodiment mentioned in this disclosure. While various novel features of the inventive principles have been shown, described and pointed out as applied to particular embodiments thereof, it should be understood that various omissions and substitutions and changes may be made by those skilled in the art without departing from the spirit of this disclosure. Those skilled in the art will appreciate that the inventive principles can be practiced in other than the described embodiments, which are presented for purposes of illustration and not limitation.

REFERENCES

1. Aalkjaer C, and Nilsson H. Vasomotion: cellular background for the oscillator and for the synchronization of smooth muscle cells. *British journal of pharmacology.* 2005; 144(5):605-16.
2. Adamo, C. M., D. F. Dai, J. M. Percival, E. Minami, M. S. Willis, E. Patrucco, S. C. Froehner, and J A. Beavo, *Sildenafil reverses cardiac dysfunction in the mdx mouse model of Duchenne muscular dystrophy*. Proc Natl Acad Sci USA, 2010. 107(44): p. 19079-83. PMC2973894
3. Altier C, Garcia-Caballero A, Simms B, You H, Chen L, Walcher J, et al. The Cavbeta subunit prevents RFP2-mediated ubiquitination and proteasomal degradation of L-type channels. *Nature neuroscience.* 2011; 14(2):173-80.
4. Anderson, M. E., A. P. Braun, Y. Wu, T. Lu, Y. Wu, H. Schulman, and R. J. Sung, *KN-93, an inhibitor of multifunctional Ca++/calmodulin-dependent protein kinase, decreases early afterdepolarizations in rabbit heart. J Pharmacol Exp Ther,* 1998. 287(3): p. 996-1006.
5. Arikkath J, and Campbell K P. Auxiliary subunits: essential components of the voltage-gated calcium channel complex. *Curr Opin Neurobiol.* 2003; 13(3):298-307.
6. Beavers, D. L., W. Wang, S. Ather, N. Voigt, A. Garbino, S. S. Dixit, A. P. Landstrom, N. Li, Q. Wang, I. Olivotto, D. Dobrev, M. J. Ackerman, and X. H. Wehrens, *Mutation E169K in junctophilin-2 causes atrial fibrillation due to impaired RyR2 stabilization.* J Am Coll Cardiol, 2013. 62(21): p. 2010-9. PMC3830688
7. Beetz N, Hein L, Meszaros J, Gilsbach R, Barreto F, Meissner M, et al. Transgenic simulation of human heart failure-like L-type Ca2+-channels: implications for fibrosis and heart rate in mice. *Cardiovasc Res.* 2009; 84(3): 396-406.
8. Best, J. M. and T. J. Kamp, *A sympathetic model of L-type Ca2+ channel-triggered arrhythmias.* Am J Physiol Heart Circ Physiol, 2010. 298(1): p. H3-4. PMC2806129
9. Bichet D, Comet V, Geib S, Carlier E, Volsen S, Hoshi T, et al. The I-II loop of the Ca2+ channel alpha1 subunit contains an endoplasmic reticulum retention signal antagonized by the beta subunit. *Neuron.* 2000; 25(1): 177-90.
10. Blaich, A., A. Welling, S. Fischer, J. W. Wegener, K. Kostner, F. Hofmann, and S. Moosmang, *Facilitation of murine cardiac L-type Ca(v)1.2 channel is modulated by calmodulin kinase II-dependent phosphorylation of S1512 and S1570.* Proc Natl Acad Sci USA, 2010. 107(22): p. 10285-9. PMC2890469
11. Blom, N., S. Gammeltoft, and S. Brunak, *Sequence and structure-based prediction of eukaryotic protein phosphorylation sites.* J Mol Biol, 1999. 294(5): p. 1351-62.
12. Borlaug, B. A., G. D. Lewis, S. E. McNulty, M. J. Semigran, M. LeWinter, H. Chen, G. Lin, A. Deswal, K. B. Margulies, and M. M. Redfield, *Effects of sildenafil on ventricular and vascular function in heart failure with preserved ejection fraction.* Circ Heart Fail, 2015. 8(3): p. 533-41. PMC4439337
13. Borlaug, B. A., V. Melenovsky, T. Marhin, P. Fitzgerald, and D. A. Kass, *Sildenafl inhibits beta-adrenergic-stimulated cardiac contractility in humans.* Circulation, 2005. 112(17): p. 2642-9.
14. Bosch, R. F., R. Gaspo, A. E. Busch, H. J. Lang, G. R. Li, and S. Nattel, *Effects of the chromanol 293B, a selective blocker of the slow, component of the delayed rectifier K+ current, on repolarization in human and guinea pig ventricular myocytes.* Cardiovasc Res, 1998. 38(2): p. 441-50.
15. Bramson, H. N., E. T. Kaiser, and A. S. Mildvan, *Mechanistic studies of cAMP-dependent protein kinase action.* CRC Crit Rev Biochem, 1984. 15(2): p. 93-124.
16. Brandmayr, J., M. Poomvanicha, K. Domes, J. Ding, A. Blaich, J. W. Wegener, S. Moosmang, and F. Hofmann, *Deletion of the C-terminal phosphorylation sites in the cardiac beta-subunit does not affect the basic beta-adrenergic response of the heart and the Ca(v)1.2 channel.* J Biol Chem, 2012. 287(27): p. 22584-92. PMC3391128
17. Brice N L, Berrow N S, Campbell V, Page K M, Brickley K, Tedder I, et al. Importance of the different beta subunits in the membrane expression of the alpha1A and alpha2 calcium channel subunits: studies using a depolarization-sensitive alpha1A antibody. *Eur J Neurosci.* 1997; 9(4): 749-59.
18. Buraei Z, and Yang J. The beta subunit of voltage-gated Ca2+ channels. *Physiological reviews.* 2010; 90(4):1461-506.
19. Burridge, P. W., E. Matsa, P. Shukla, Z. C. Lin, J. M. Churko, A. D. Ebert, F. Lan, S. Diecke, B. Huber, N. M. Mordwinkin, J. R. Plews, O. J. Abilez, B. Cui, J. D. Gold, and J. C. Wu, *Chemically defined generation of human cardiomyocytes.* Nat Methods, 2014. 11(8): p. 855-60. PMC4169698
20. Calaghan, S. C., J. Y. Le Guennec, and E. White, *Modulation of Ca(2+) signaling by microtubule disruption in rat ventricular myocytes and its dependence on the ruptured patch-clamp configuration.* Circ Res, 2001. 88(4): p. E32-7.
21. Castellano A, Wei X, Bimbaumer L, and Perez-Reyes E. Cloning and expression of a neuronal calcium channel beta subunit. *J Biol Chem.* 1993; 268(17):12359-66.
22. Catterall W A. Structure and regulation of voltage-gated Ca2+ channels. *Annu Rev Cell Dev Biol.* 2000; 16:521-55.
23. Chen X, Nakayama H, Zhang X, Ai X, Harris D M, Tang M, et al. Calcium influx through Cav1.2 is a proximal signal for pathological cardiomyocyte hypertrophy. *J Mol Cell Cardiol.* 2011; 50(3):460-70.

24. Chen X, Zhang X, Kubo H, Harris D M, Mills G D, Moyer J, et al. Ca2+ influx-induced sarcoplasmic reticulum Ca2+ overload causes mitochondrial-dependent apoptosis in ventricular myocytes. *Circ Res.* 2005; 97(10):1009-17.
25. Chen, Y. H., M. H. Li, Y. Zhang, L. L. He, Y. Yamada, A. Fitzmaurice, Y. Shen, H. Zhang, L. Tong, and J. Yang, *Structural basis of the alpha1-beta subunit interaction of voltage-gated Ca2+ channels.* Nature, 2004. 429(6992): p. 675-80.
26. Cheng, H. C. and J. Incardona, *Models of torsades de pointes: effects of FPL64176, DPI201106, dofetilide, and chromanol 2938 in isolated rabbit and guinea pig hearts.* J Pharmacol Toxicol Methods, 2009. 60(2): p. 174-84.
27. Cheng, J., C. R. Valdivia, R. Valdyanathan, R. C. Balijepalli, M. J. Ackerman, and J. C. Makielski, *Caveolin-3 suppresses late sodium current by inhibiting nNOS-dependent S-nitrosylation of SCN5A.* J Mol Cell Cardiol, 2013. 61: p. 102-10. PMC3720711
28. Chiang, C. E., H. N. Luk, T. M. Wang, and P. Y. Ding, *Effects of sildenafil on cardiac repolarization.* Cardiovasc Res, 2002. 55(2): p. 290-9.
29. Chidlow, J. H., Jr. and W. C. Sessa, *Caveolae, caveolins, and cavins: complex control of cellular signalling and inflammation.* Cardiovasc Res, 2010. 86(2): p. 219-25. PMC2856194
30. Chien A J, Zhao X, Shirokov R E, Puri T S, Chang C F, Sun D, et al. Roles of a membrane-localized beta subunit in the formation and targeting of functional L-type Ca2+ channels. *J Biol Chem.* 1995; 270(50):30036-44.
31. Cingolani E, Ramirez Correa G A, Kizana E, Murata M, Cho H C, and Marban E. Gene therapy to inhibit the calcium channel beta subunit: physiological consequences and pathophysiological effects in models of cardiac hypertrophy. *Circ Res.* 2007; 101(2):166-75.
32. Colecraft, H. M., B. Alseikhan, S. X. Takahashi, D. Chaudhuri, S. Mittman, V. Yegnasubramanian, R. S. Alvania, D. C. Johns, E. Marban, and D. T. Yue, *Novel functional properties of Ca(2+) channel beta subunits revealed by their expression in adult rat heart cells.* J Physiol, 2002. 541(Pt 2): p. 435-52. PMC2290333
33. Colyer J. Phosphorylation states of phospholamban. *Ann N Y Acad Sci.* 1998; 853:79-91.
34. De Jongh, K. S., B. J. Murphy, A. A. Colvin, J. W. Hell, M. Takahashi, and W. A. Catterall, *Specific phosphorylation of a site in the full-length form of the alpha 1 subunit of the cardiac L-type calcium channel by adenosine 3',5'-cyclic monophosphate-dependent protein kinase.* Biochemistry, 1996. 35(32): p. 10392-402.
35. Dolphin A C. Beta subunits of voltage-gated calcium channels. *J Bioenerg Biomembr.* 2003; 35(6):599-620.
36. Dolphin, A. C., *Age of quantitative proteomics hits voltage-gated calcium channels.* Proc Natl Acad Sci USA, 2010. 107(34): p. 14941-2. PMC2930547
37. Domes K, Ding J, Lemke T, Blaich A, Wegener J W, Brandmayr J, et al. Truncation of murine CaV1.2 at Asp-1904 results in heart failure after birth. *J Biol Chem.* 2011; 286(39):33863-71.
38. Dorian, P., *Antiarrhythmic action of beta-blockers: potential mechanisms.* J Cardiovasc Pharmacol Ther, 2005. 10 Suppl 1: p. S15-22.
39. Dostmann, W. R., S. S. Taylor, H. G. Genieser, B. Jastorff, S. O. Doskeland, and D. Ogreid, *Probing the cyclic nucleotide binding sites of cAMP-dependent protein kinases I and II with analogs of adenosine 3',5'-cyclic phosphorothioates.* J Biol Chem, 1990. 265(18): p. 10484-91.
40. Dumitrascu, R., N. Weissmann, H. A. Ghofrani, E. Dony, K. Beuerlein, H. Schmidt, J. P. Stasch, M. J. Gnoth, W. Seeger, F. Grimminger, and R. T. Schermuly, *Activation of soluble guanylate cyclase reverses experimental pulmonary hypertension and vascular remodeling.* Circulation, 2006. 113(2): p. 286-95.
41. Eisner D A, Kashimura T, O'Neill S C, Venetucci L A, and Trafford A W. What role does modulation of the ryanodine receptor play in cardiac inotropy and arrhythmogenesis? *J Mol Cell Cardiol.* 2009; 46(4):474-81.
42. Erickson M G, Alseikhan B A, Peterson B Z, and Yue D T. Preassociation of calmodulin with voltage-gated Ca(2+) channels revealed by FRET in single living cells. *Neuron.* 2001; 31(6):973-85.
43. Fabiato A. Simulated calcium current can both cause calcium loading in and trigger calcium release from the sarcoplasmic reticulum of a skinned canine cardiac Purkinje cell. *J Gen Physiol.* 1985; 85(2):291-320.
44. Fang K, and Colecraft H M. Mechanism of auxiliary beta-subunit-mediated membrane targeting of L-type (Ca(V)1.2) channels. *J Physiol.* 2011; 589(Pt 18):4437-55.
45. Feramisco, J. R., D. B. Glass, and E. G. Krebs, *Optimal spatial requirements for the location of basic residues in peptide substrates for the cyclic AMP-dependent protein kinase.* J Biol Chem, 1980. 255(9): p. 4240-5.
46. Fiedler, B., S. M. Lohmann, A. Smolenski, S. Linnemuller, B. Pieske, F. Schroder, J. D. Molkentin, H. Drexler, and K. C. Wollert, *Inhibition of calcineurin-NFAT hypertrophy signaling by cGMP-dependent protein kinase type I in cardiac myocytes.* Proc Natl Acad Sci USA, 2002. 99(17): p. 11363-8. PMC123262
47. Findeisen F, and Minor D L, Jr. Disruption of the IS6-AID linker affects voltage-gated calcium channel inactivation and facilitation. *J Gen Physiol.* 2009; 133(3): 327-43.
48. Froese, A., S. S. Breher, C. Waldeyer, R. F. Schindler, V. O. Nikolaev, S. Rinne, E. Wischmeyer, J. Schlueter, J. Becher, S. Simrick, F. Vauti, J. Kuhtz, P. Meister, S. Kreissl, A. Torlopp, S. K. Liebig, S. Laakmann, T. D. Muller, J. Neumann, J. Stieber, A. Ludwig, S. K. Maier, N. Decher, H. H. Arnold, P. Kirchhof, L. Fabritz, and T. Brand, *Popeye domain containing proteins are essential for stress-mediated modulation of cardiac pacemaking in mice.* J Clin Invest, 2012. 122(3): p. 1119-30. PMC3287222
49. Fu Y, Westenbroek R E, Yu F H, Clark J P, 3rd, Marshall M R, Scheuer T, et al. Deletion of the distal C terminus of CaV1.2 channels leads to loss of beta-adrenergic regulation and heart failure in vivo. *J Biol Chem.* 2011; 286 (14):12617-26.
50. Fu, Y., R. E. Westenbroek, T. Scheuer, and W. A. Catterall, *Phosphorylation sites required for regulation of cardiac calcium channels in the fight-or-flight response.* Proc Natl Acad Sci USA, 2013. 110(48): p. 19621-6. PMC3845157
51. Fuller, M. D., M. A. Emrick, M. Sadilek, T. Scheuer, and W. A. Catterall, *Molecular mechanism of calcium channel regulation in the fight-or-flight response.* Sci Signal, 2010. 3(141): p. ra70. PMC3063709
52. Ganesan, A. N., C. Maack, D. C. Johns, A. Sidor, and B. O'Rourke, *Beta-adrenergic stimulation of L-type Ca2+ channels in cardiac myocytes requires the distal carboxyl terminus of alpha1 C but not serine 1928.* Circ Res, 2006. 98(2): p. e11-8. PMC2692538
53. Gerhardstein B L, Puri T S, Chien A J, and Hosey M M. Identification of the sites phosphorylated by cyclic AMP-dependent protein kinase on the beta 2 subunit of L-type voltage-dependent calcium channels. *Biochemistry.* 1999; 38(32):10361-70.
54. Gogelein, H., A. Bruggemann, U. Gerlach, J. Brendel, and A. E. Busch, *Inhibition of IKs channels by HMR 1556.* Naunyn Schmiedebergs Arch Pharmacol, 2000. 362(6): p. 480-8.
55. Gorelik, J., P. T. Wright, A. R. Lyon, and S. E. Harding, *Spatial control of the betaAR system in heart failure: the transverse tubule and beyond.* Cardiovasc Res, 2013. 98(2): p. 216-24. PMC3633155
56. Guo, A., X. Zhang, V. R. Iyer, B. Chen, C. Zhang, W. J. Kutschke, R. M. Weiss, C. Franzini-Armstrong, and L. S. Song, *Overexpression of junctophilin-2 does not enhance baseline function but attenuates heart failure development after cardiac stress.* Proc Natl Acad Sci USA, 2014. 111(33): p. 12240-5. PMC4143026
57. Guo, L., Z. Dong, and H. Guthrie, *Validation of a guinea pig Langendorff heart model for assessing potential cardiovascular liability of drug candidates.* J Pharmacol Toxicol Methods, 2009. 60(2): p. 130-51.
58. Haase, H., *Ahnak, a new player in beta-adrenergic regulation of the cardiac L-type Ca2+ channel.* Cardiovasc Res, 2007. 73(1): p. 19-25.
59. Haase, H., J. Alvarez, D. Petzhold, A. Doller, J. Behlke, J. Erdmann, R. Hetzer, V. Regitz-Zagrosek, G. Vassort, and I. Morano, *Ahnak is critical for cardiac Ca(V)1.2 calcium channel function and its beta-adrenergic regulation.* FASEB J, 2005. 19(14): p. 1969-77.
60. Haase, H., T. Podzuweit, G. Lutsch, A. Hohaus, S. Kostka, C. Lindschau, M. Kott, R. Kraft, and I. Morano, *Signaling from beta-adrenoceptor to L-type calcium channel: Identification of a novel cardiac protein kinase A target possessing similarities to AHNAK.* FASEB J, 1999. 13(15): p. 2161-72.
61. Hambleton M, York A, Sargent M A, Kaiser R A, Lorenz J N, Robbins J, et al. Inducible and myocyte-specific inhibition of PKCalpha enhances cardiac contractility and protects against infarction-induced heart failure. *Am J Physiol Heart Circ Physiol.* 2007; 293(6):H3768-71.
62. He M, Bodi I, Mikala G, and Schwartz A. Motif III S5 of L-type calcium channels is involved in the dihydropyridine binding site. A combined radioligand binding and electrophysiological study. *J Biol Chem.* 1997; 272 (5):2629-33.
63. Hennessey, J. A., C A. Marcou, C. Wang, E. Q. Wei, C. Wang, D. J. Tester, M. Torchio, F. Dagradi, L. Crotti, P. J. Schwartz, M. J. Ackerman, and G. S. Pitt, *FGF12 is a candidate Brugada syndrome locus.* Heart Rhythm, 2013. 10(12): p. 1886-94. PMC3870051
64. Hennessey, J. A., E. Q. Wei, and G. S. Pitt, *Fibroblast growth factor homologous factors modulate cardiac calcium channels.* Circ Res, 2013. 113(4): p. 381-8. PMC3813963
65. Hockerman G H, Peterson B Z, Sharp E, Tanada T N, Scheuer T, and Catterall W A. Construction of a high-affinity receptor site for dihydropyridine agonists and antagonists by single amino acid substitutions in a non-L-type Ca2+ channel. *Proc Natl Acad Sci USA.* 1997; 94(26):14906-11.
66. Hong, T., H. Yang, S. S. Zhang, H. C. Cho, M. Kalashnikova, B. Sun, H. Zhang, A. Bhargava, M. Grabe, J. Olgin, J. Gorelik, E. Marban, L. Y. Jan, and R. M. Shaw, *Cardiac BIN1 folds T-tubule membrane, controlling ion flux and limiting arrhythmia.* Nat Med, 2014. 20(6): p. 624-32. PMC4048325
67. Hong, T. T., J. W. Smyth, D. Gao, K. Y. Chu, J. M. Vogan, T. S. Fong, B. C. Jensen, H. M. Colecraft, and R. M. Shaw, *BIN1 localizes the L-type calcium channel to cardiac T-tubules.* PLoS Biol, 2010. 8(2): p. e1000312. PMC2821894
68. Hulme, J. T., K. Konoki, T. W. Lin, M. A. Gritsenko, D. G. Camp, 2nd, D. J. Bigelow, and W. A. Catterall, *Sites of proteolytic processing and noncovalent association of the distal C-terminal domain of CaV1.1 channels in skeletal muscle.* Proc Natl Acad Sci USA, 2005. 102(14): p. 5274-9. PMC555994
69. Hung, V., N. D. Udeshi, S. S. Lam, K. H. Loh, K. J. Cox, K. Pedram, S. A. Carr, and A. Y. Ting, *Spatially resolved proteomic mapping in living cells with the engineered peroxidase APEX2.* Nat Protoc, 2016. 11(3): p. 456-75. PMC4863649
70. Hung, V., P. Zou, H. W. Rhee, N. D. Udeshi, V. Cracan, T. Svinkina, S. A. Carr, V. K. Mootha, and A. Y. Ting, *Proteomic mapping of the human mitochondrial intermembrane space in live cells via ratiometric APEX tagging.* Mol Cell, 2014. 55(2): p. 332-41. PMC4743503
71. Iakoucheva, L. M., P. Radivojac, C. J. Brown, T. R. O'Connor, J. G. Sikes, Z. Obradovic, and A. K. Dunker, *The importance of intrinsic disorder for protein phosphorylation.* Nucleic Acids Res, 2004. 32(3): p. 1037-49. PMC373391
72. January, C. T. and J. M. Riddle, *Early afterdepolarizations: mechanism of induction and block. A role for L-type Ca2+ current.* Circ Res, 1989. 64(5): p. 977-90.
73. Jiang, M., M. Zhang, M. Howren, Y. Wang, A. Tan, R. C. Balijepalli, J. F. Huizar, and G. N. Tseng, *JPH-2 interacts with Cai-handling proteins and ion channels in dyads: Contribution to premature ventricular contraction-induced cardiomyopathy.* Heart Rhythm, 2016. 13(3): p. 743-52. PMC4762763
74. Jost, N., L. Virag, M. Bitay, J. Takacs, C. Lengyel, P. Biliczki, Z. Nagy, G. Bogats, D. A. Lathrop, J. G. Papp, and A. Varro, *Restricting excessive cardiac action potential and QT prolongation: a vital role for IKs in human ventricular muscle.* Circulation, 2005. 112(10): p. 1392-9.
75. Kamp T J, and Hell J W. Regulation of cardiac L-type calcium channels by protein kinase A and protein kinase C. *Circ Res.* 2000; 87(12):1095-102.
76. Katchman, A., L. Yang, S. I. Zakharov, J. Kushner, J. Abrams, B. X. Chen, G. Liu, G. S. Pitt, H. M. Colecraft, and S. O. Marx, *Proteolytic cleavage and PKA phosphorylation of alpha1C subunit are not required for adrenergic regulation of CaV1.2 in the heart.* Proc Natl Acad Sci USA, 2017. 114(34): p. 9194-9199.
77. Katiyar, R., P. Weissgerber, E. Roth, J. Dorr, V. Sothilingam, M. Garcia Garrido, S. C. Beck, M. W. Seeliger, A. Beck, F. Schmitz, and V. Flockerzi, *Influence of the beta2-Subunit of L-Type Voltage-Gated Cav Channels on the Structural and Functional Development of Photoreceptor Ribbon Synapses.* Invest Ophthalmol Vis Sci, 2015. 56(4): p. 2312-24.
78. Kemp, B. E., D. J. Graves, E. Benjamini, and E. G. Krebs, *Role of multiple basic residues in determining the substrate specificity of cyclic AMP-dependent protein kinase.* J Biol Chem, 1977. 252(14): p. 4888-94.
79. Khairallah, M., R. J. Khairallah, M. E. Young, B. G. Allen, M. A. Gillis, G. Danialou, C. F. Deschepper, B. J. Petrof, and C. Des Rosiers, *Sildenafil and cardiomyocyte-specific cGMP signaling prevent cardiomyopathic changes associated with dystrophin deficiency.* Proc Natl Acad Sci USA, 2008. 105(19): p. 7028-33. PMC2383977

80. Kim, G. E. and D. A. Kass, *Cardiac Phosphodiesterases and Their Modulation for Treating Heart Disease*. Handb Exp Pharmacol, 2016.
81. Kline, C. F., J. Scott, J. Curran, T. J. Hund, and P. J. Mohler, *Ankyrin-B regulates Cav2.1 and Cav2.2 channel expression and targeting*. J Biol Chem, 2014. 289(8): p. 5285-95. PMC3931084
82. Knollmann, B. C. and J. D. Potter, *Altered regulation of cardiac muscle contraction by troponin T mutations that cause familial hypertrophic cardiomyopathy*. Trends Cardiovasc Med, 2001. 11(5): p. 206-12.
83. Kushnir A, Betzenhauser M J, and Marks A R. Ryanodine receptor studies using genetically engineered mice. *FEBS Lett.* 2010; 584(10):1956-65.
84. Kushnir A, Marx S O. *Voltage-gated Calcium Channels*. from the book by Zipes D, Jalife J, Cardiac *Electrophysiology: From Cell to Bedside*, Seventh Edition, Elsevier, July 2017.
85. Kushnir A, Shan J, Betzenhauser M J, Reiken S, and Marks A R. Role of CaMKIIdelta phosphorylation of the cardiac ryanodine receptor in the force frequency relationship and heart failure. *Proc Natl Acad Sci USA.* 2010; 107(22):10274-9.
86. Lacerda A E, Kim H S, Ruth P, Perez-Reyes E, Flockerzi V, Hofmann F, et al. Normalization of current kinetics by interaction between the alpha 1 and beta subunits of the skeletal muscle dihydropyridine-sensitive Ca2+ channel. *Nature.* 1991; 352(6335):527-30.
87. Lam, S. S., J. D. Martell, K. J. Kamer, T. J. Deerinck, M. H. Ellisman, V. K. Mootha, and A. Y. Ting, *Directed evolution of APEX2 for electron microscopy and proximity labeling*. Nat Methods, 2015. 12(1): p. 51-4. PMC4296904
88. Lemke, T., A. Welling, C. J. Christel, A. Blaich, D. Bernhard, P. Lenhardt, F. Hofmann, and S. Moosmang, *Unchanged beta-adrenergic stimulation of cardiac L-type calcium channels in Ca v 1.2 phosphorylation site S1928A mutant mice*. J Biol Chem, 2008. 283(50): p. 34738-44. PMC3259877
89. Loh, K. H., P. S. Stawski, A. S. Draycott, N. D. Udeshi, E. K. Lehrman, D. K. Wilton, T. Svinkina, T. J. Deerinck, M. H. Ellisman, B. Stevens, S. A. Carr, and A. Y. Ting, *Proteomic Analysis of Unbounded Cellular Compartments: Synaptic Clefts*. Cell, 2016. 166(5): p. 1295-1307 e21. PMC5167540
90. Lundby, A., E. J. Rossin, A. B. Steffensen, M. R. Acha, C. Newton-Cheh, A. Pfeufer, S. N. Lynch, Q. T. I. I. G. Consortium, S. P. Olesen, S. Brunak, P. T. Ellinor, J. W. Jukema, S. Trompet, I. Ford, P. W. Macfarlane, B. P. Krijthe, A. Hofman, A. G. Uitterlinden, B. H. Stricker, H. M. Nathoe, W. Spiering, M. J. Daly, F. W. Asselbergs, P. van der Harst, D. J. Milan, P. I. de Bakker, K. Lage, and J. V. Olsen, *Annotation of loci from genome-wide association studies using tissue-specific quantitative interaction proteomics*. Nat Methods, 2014. 11(8): p. 868-74. PMC4117722
91. Lundby, A., M. N. Andersen, A. B. Steffensen, H. Horn, C. D. Kelstrup, C. Francavilla, L. J. Jensen, N. Schmitt, M. B. Thomsen, and J. V. Olsen, *In vivo phosphoproteomics analysis reveals the cardiac targets of beta-adrenergic receptor signaling*. Sci Signal, 2013. 6(278): p. rs11.
92. Makarewich, C. A., R. N. Correll, H. Gao, H. Zhang, B. Yang, R. M. Berretta, V. Rizzo, J. D. Molkentin, and S. R. Houser, *A caveolae-targeted L-type Ca(2)+ channel antagonist inhibits hypertrophic signaling without reducing cardiac contractility*. Circ Res, 2012. 110(5): p. 669-74. PMC3324037
93. Malan, D., M. P. Gallo, I. Bedendi, C. Biasin, R. C. Levi, and G. Alloatti, *Microtubules mobility affects the modulation of L-type I(Ca) by muscarinic and beta-adrenergic agonists in guinea-pig cardiac myocytes*. J Mol Cell Cardiol, 2003. 35(2): p. 195-206.
94. Maltez J M, Nunziato D A, Kim J, and Pitt G S. Essential Ca(V)beta modulatory properties are AID-independent. *Nat Struct Mol Biol.* 2005; 12(4):372-7.
95. Marban, E., S. W. Robinson, and W. G. Wier, *Mechanisms of arrhythmogenic delayed and early afterdepolarizations in ferret ventricular muscle*. J Clin Invest, 1986. 78(5): p. 1185-92. PMC423803
96. Marx S O, Reiken S, Hisamatsu Y, Jayaraman T, Burkhoff O, Rosemblit N, et al. PKA phosphorylation dissociates FKBP12.6 from the calcium release channel (ryanodine receptor): defective regulation in failing hearts. *Cell.* 2000; 101(4):365-76.
97. Meissner M, Weissgerber P, Londono J E, Prenen J, Link S, Ruppenthal S, et al. Moderate calcium channel dysfunction in adult mice with inducible cardiomyocyte-specific excision of the cacnb2 gene. *J Biol Chem.* 2011; 286(18):15875-82.
98. Mick, D. U., R. B. Rodrigues, R. D. Leib, C. M. Adams, A. S. Chien, S. P. Gygi, and M. V. Nachury, *Proteomics of Primary Cilia by Proximity Labeling*. Dev Cell, 2015. 35(4): p. 497-512. PMC4662609
99. Min D, Guo F, Zhu S, Xu X, Mao X, Cao Y, et al. The alterations of Ca2+/calmodulin/CaMKII/CaV1.2 signaling in experimental models of Alzheimer's disease and vascular dementia. *Neurosci Lett.* 2013; 538:60-5.
100. Miriyala, J., T. Nguyen, D. T. Yue, and H. M. Colecraft, *Role of CaVbeta subunits, and lack of functional reserve, in protein kinase A modulation of cardiac CaV1.2 channels*. Circ Res, 2008. 102(7): p. e54-64.
101. Mohler, P. J., J. J. Schott, A. O. Gramolini, K. W. Dilly, S. Guatimosim, W. H. duBell, L. S. Song, K. Haurogne, F. Kyndt, M. E. Ali, T. B. Rogers, W. J. Lederer, D. Escande, H. Le Marec, and V. Bennett, *Ankyrin-B mutation causes type 4 long-QT cardiac arrhythmia and sudden cardiac death*. Nature, 2003. 421(6923): p. 634-9.
102. Moore, M. J., J. A. Adams, and S. S. Taylor, *Structural basis for peptide binding in protein kinase A. Role of glutamic acid 203 and tyrosine 204 in the peptide-positioning loop*. J Biol Chem, 2003. 278(12): p. 10613-8.
103. Morrow, J. P. and S. O. Marx, *Novel approaches to examine the regulation of voltage-gated calcium channels in the heart*. Curr Mol Pharmacol, 2015. 8(1): p. 61-8.
104. Morrow, J. P., A. N. Katchman, N.-P. Son, C. M. Trent, R. Khan, T. Shiomi, V. Amin, J. M. Lader, C. Vasquez, G. E. Morley, J. D'Armiento, S. Homma, I. J. Goldberg, and S. O. Marx, *Mice with cardiac over-expression of peroxisome proliferator-activated receptor gamma have impaired repolarization and spontaneous fatal ventricular arrhythmias*. Circulation, 2011. In press.
105. Muirhead, G. J., M. B. Wulff, A. Fielding, D. Kleinermans, and N. Buss, *Pharmacokinetic interactions between sildenafil and saquinavir/ritonavir*. Br J Clin Pharmacol, 2000. 50(2): p. 99-107. PMC2014393
106. Muraski J A, Fischer K M, Wu W, Cottage C T, Quijada P, Mason M, et al. Pim-1 kinase antagonizes aspects of myocardial hypertrophy and compensation to pathological pressure overload. *Proc Nat Acad Sci USA.* 2008; 105(37):13889-94.

107. Muth J N, Yamaguchi H, Mikala G, Grupp I L, Lewis W, Cheng H, et al. Cardiac-specific overexpression of the alpha(1) subunit of the L-type voltage-dependent Ca(2+) channel in transgenic mice. Loss of isoproterenol-induced contraction. *J Biol Chem.* 1999; 274(31):21503-6.

108. Negroni J A, Morotti S, Lascano E C, Gomes A V, Grandi E, Puglisi J L, et al. beta-adrenergic effects on cardiac myofilaments and contraction in an integrated rabbit ventricular myocyte model. *J Mol Cell Cardiol.* 2015; 81:162-75.

109. Neuberger, G., G. Schneider, and F. Eisenhaber, *pkaPS: prediction of protein kinase A phosphorylation sites with the simplified kinase-substrate binding model.* Biol Direct, 2007. 2: p. 1. PMC1783638

110. Obenauer, J. C., L. C. Cantley, and M. B. Yaffe, *Scansite 2.0: Proteome-wide prediction of cell signaling interactions using short sequence motifs.* Nucleic Acids Res, 2003. 31(13): p. 3635-41. PMC168990

111. Obermair G J, Schlick B, Di Biase V, Subramanyam P, Gebhart M, Baumgartner S, et al. Reciprocal interactions regulate targeting of calcium channel beta subunits and membrane expression of alpha1 subunits in cultured hippocampal neurons. *J Biol Chem.* 2010; 285(8):5776-91.

112. O'Connell T D, Rodrigo M C, and Simpson P C. Isolation and culture of adult mouse cardiac myocytes. *Methods Mol Biol.* 2007; 357:271-96.

113. Opatowsky, Y., C. C. Chen, K. P. Campbell, and J. A. Hirsch, *Structural analysis of the voltage-dependent calcium channel beta subunit functional core and its complex with the alpha 1 interaction domain.* Neuron, 2004. 42(3): p. 387-99.

114. Overholser, B. R., X. Zheng, and J. E. Tisdale, *Paroxysmal beta-adrenergic receptor-mediated alterations in ventricular repolarization at rapid heart rates during inhibition of delayed rectifier currents.* J Cardiovasc Pharmacol, 2009. 54(3): p. 253-62.

115. Pankonien, I., J. L. Alvarez, A. Doller, C. Kohncke, D. Rotte, V. Regitz-Zagrosek, I. Morano, and H. Haase, *Ahnak1 is a tuneable modulator of cardiac Ca(v)1.2 calcium channel activity.* J Muscle Res Cell Motil, 2011. 32(4-5): p. 281-90.

116. Pasca, S. P., T. Portmann, I. Voineagu, M. Yazawa, A. Shcheglovitov, A. M. Pasca, B. Cord, T. D. Palmer, S. Chikahisa, S. Nishino, J. A. Bernstein, J. Hallmayer, D. H. Geschwind, and R. E. Dolmetsch, *Using iPSC-derived neurons to uncover cellular phenotypes associated with Timothy syndrome.* Nat Med, 2011. 17(12): p. 1657-62. PMC3517299

117. Perez-Reyes E, Castellano A, Kim H S, Bertrand P, Baggstrom E, Lacerda A E, et al. Cloning and expression of a cardiac/brain beta subunit of the L-type calcium channel. *J Biol Chem.* 1992; 267(3):1792-7.

118. Peterson B Z, DeMaria C D, Adelman J P, and Yue D T. Calmodulin is the Ca2+ sensor for Ca2+-dependent inactivation of L-type calcium channels. *Neuron.* 1999; 22(3):549-58.

119. Rainer, P. P. and D A. Kass, *Old dog, new tricks: novel cardiac targets and stress regulation by protein kinase G.* Cardiovasc Res, 2016. 111(2): p. 154-62. PMC4937204

120. Rees, J. S., X. W. Li, S. Perrett, K. S. Lilley, and A. P. Jackson, *Protein Neighbors and Proximity Proteomics.* Mol Cell Proteomics, 2015. 14(11): p. 2848-56. PMC4638030

121. Reuter H, and Scholz H. The regulation of the calcium conductance of cardiac muscle by adrenaline. *J Physiol.* 1977; 264(1):49-62.

122. Reynolds, J. O., D. Y. Chiang, W. Wang, D. L. Beavers, S. S. Dixit, D. G. Skapura, A. P. Landstrom, L. S. Song, M. J. Ackerman, and X. H. Wehrens, *Junctophilin-2 is necessary for T-tubule maturation during mouse heart development.* Cardiovasc Res, 2013. 100(1): p. 44-53. PMC3778955

123. Rubi, L., V. S. Gawali, H. Kubista, H. Todt, K. Hilber, and X. Koenig, *Proper Voltage-Dependent Ion Channel Function in Dysferlin-Deficient Cardiomyocytes.* Cell Physiol Biochem, 2015. 36(3): p. 1049-58.

124. Rueckschloss, U. and G. Isenberg, *Cytochalasin D reduces Ca2+ currents via cofilin-activated depolymerization of F-actin in guinea-pig cardiomyocytes.* J Physiol, 2001. 537(Pt 2): p. 363-70. PMC2278948

125. Sadeghi, A., A. D. Doyle, and B. D. Johnson, *Regulation of the cardiac L-type Ca2+ channel by the actin-binding proteins alpha-actinin and dystrophin.* Am J Physiol Cell Physiol, 2002. 282(6): p. C1502-11.

126. Sanbe A, Gulick J, Hanks M C, Liang Q, Osinska H, and Robbins J. Reengineering inducible cardiac-specific transgenesis with an attenuated myosin heavy chain promoter. *Circ Res.* 2003; 92(6):609-16.

127. Sasaki, H., T. Nagayama, R. M. Blanton, K. Seo, M. Zhang, G. Zhu, D. I. Lee, D. Bedja, S. Hsu, O. Tsukamoto, S. Takashima, M. Kitakaze, M. E. Mendelsohn, R. H. Karas, D. A. Kass, and E. Takimoto, *PDE5 inhibitor efficacy is estrogen dependent in female heart disease.* J Clin Invest, 2014. 124(6): p. 2464-71. PMC4089449

128. Schreieck, J., Y. Wang, V. Gjini, M. Korth, B. Zrenner, A. Schomig, and C. Schmitt, *Differential effect of beta-adrenergic stimulation on the frequency-dependent electrophysiologic actions of the new class III antiarrhythmics dofetilide, ambasilide, and chromanol 293B.* J Cardiovasc Electrophysiol, 1997. 8(12): p. 1420-30.

129. Scriven D R, Dan P, and Moore E D. Distribution of proteins implicated in excitation-contraction coupling in rat ventricular myocytes. *Biophys J.* 2000; 79(5):2682-91.

130. Senzaki, H., C. J. Smith, G. J. Juang, T. Isoda, S. P. Mayer, A. Ohler, N. Paolocci, G. F. Tomaselli, J. M. Hare, and D. A. Kass, *Cardiac phosphodiesterase 5 (cGMP-specific) modulates beta-adrenergic signaling in vivo and is down-regulated in heart failure.* FASEB J, 2001. 15(10): p. 1718-26.

131. Shan J, Kushnir A, Betzenhauser M J, Reiken S, Li J, Lehnart S E, et al. Phosphorylation of the ryanodine receptor mediates the cardiac fight or flight response in mice. *J Clin Invest.* 2010; 120(12):4388-98.

132. Shimizu, K., Y. Shintani, W. G. Ding, H. Matsuura, and T. Bamba, *Potentiation of slow component of delayed rectifier K(+) current by cGMP via two distinct mechanisms: inhibition of phosphodiesterase 3 and activation of protein kinase G.* Br J Pharmacol, 2002. 137(1): p. 127-37. PMC1573469

133. Shimizu, W. and C. Antzelevitch, *Differential effects of beta-adrenergic agonists and antagonists in LQT1, LQT2 and LQT3 models of the long QT syndrome.* J Am Coil Cardiol, 2000. 35(3): p. 778-86.

134. Shimizu, W. and C. Antzelevitch, *Effects of a K(+) channel opener to reduce transmural dispersion of repolarization and prevent torsade de pointes in LQT1, LQT2, and LQT3 models of the long-QT syndrome.* Circulation, 2000. 102(6): p. 706-12.

135. Shimizu, W., T. Noda, H. Takaki, N. Nagaya, K. Satomi, T. Kurita, K. Suyama, N. Aihara, K. Sunagawa, S. Echigo, Y. Miyamoto, Y. Yoshimasa, K. Nakamura, T. Ohe, J. A. Towbin, S. G. Priori, and S. Kamakura, *Diagnostic value of epinephrine test for genotyping*

*LQT1, LQT2, and LQT3 forms of congenital long QT syndrome.* Heart Rhythm, 2004. 1(3): p. 276-83.
136. Shimizu, W., T. Noda, H. Takaki, T. Kurta, N. Nagaya, K. Satomi, K. Suyama, N. Aihara, S. Kamakura, K. Sunagawa, S. Echigo, K. Nakamura, T. Ohe, J. A. Towbin, C. Napolitano, and S. G. Priori, *Epinephrine unmasks latent mutation carriers with LQT1 form of congenital long-QT syndrome.* J Am Coll Cardiol, 2003. 41(4): p. 633-42.
137. Smolenski, A., *Novel roles of cAMP/cGMP-dependent signaling in platelets.* J Thromb Haemost, 2012. 10(2): p. 167-76.
138. Sohal, D. S., M. Nghiem, M. A. Crackower, S. A. Witt, T. R. Kimball, K. M. Tymitz, J. M. Penninger, and J. D. Molkentin, *Temporally regulated and tissue-specific gene manipulations in the adult and embryonic heart using a tamoxifen-inducible Cre protein.* Circ Res, 2001. 89(1): p. 20-5.
139. Songyang, Z., S. Blechner, N. Hoagland, M. F. Hoekstra, H. Piwnica-Worms, and L. C. Cantley, *Use of an oriented peptide library to determine the optimal substrates of protein kinases.* Curr Biol, 1994. 4(11): p. 973-82.
140. Splawski, I., K. W. Timothy, L. M. Sharpe, N. Decher, P. Kumar, R. Bloise, C. Napolitano, P. J. Schwartz, R. M. Joseph, K. Condouris, H. Tager-Flusberg, S. G. Priori, M. C. Sanguinetti, and M. T. Keating, *Ca(V)1.2 calcium channel dysfunction causes a multisystem disorder including arrhythmia and autism.* Cell, 2004. 119(1): p. 19-31.
141. Splawski, I., K. W. Timothy, N. Decher, P. Kumar, F. B. Sachse, A. H. Beggs, M. C. Sanguinetti, and M. T. Keating, *Severe arrhythmia disorder caused by cardiac L-type calcium channel mutations.* Proc Natl Acad Sci USA, 2005. 102(23): p. 8089-96; discussion 8086-8. PMC1149428
142. Subramanyam, P., D. D. Chang, K. Fang, W. Xie, A. R. Marks, and H. M. Colecraft, *Manipulating L-type calcium channels in cardiomyocytes using split-intein protein transsplicing.* Proc Natl Acad Sci USA, 2013. 110(38): p. 15461-6. PMC3780916
143. Takahashi, S. X., S. Mittman, and H. M. Colecraft, *Distinctive modulatory effects of five human auxiliary beta2 subunit splice variants on L-type calcium channel gating.* Biophys J, 2003. 84(5): p. 3007-21. PMC1302863
144. Takimoto, E., H. C. Champion, M. Li, D. Belardi, S. Ren, E. R. Rodriguez, D. Bedja, K. L. Gabrielson, Y. Wang, and D A. Kass, *Chronic inhibition of cyclic GMP phosphodiesterase 5A prevents and reverses cardiac hypertrophy.* Nat Med, 2005. 11(2): p. 214-22.
145. Tang M, Zhang X, Li Y, Guan Y, Ai X, Szeto C, et al. Enhanced basal contractility but reduced excitation-contraction coupling efficiency and beta-adrenergic reserve of hearts with increased Cav1.2 activity. *Am J Physiol Heart Circ Physiol.* 2010; 299(2):H519-28.
146. Terrenoire, C., C. E. Clancy, J. W. Cormier, K. J. Sampson, and R. S. Kass, *Autonomic control of cardiac action potentials: role of potassium channel kinetics in response to sympathetic stimulation.* Circ Res, 2005. 96(5): p. e25-34.
147. Tomaselli, G. F. and D. P. Zipes, *What causes sudden death in heart failure?* Circ Res, 2004. 95(8): p. 754-63.
148. Uzun, A. U., I. Mannhardt, K. Breckwoldt, A. Horvath, S. S. Johannsen, A. Hansen, T. Eschenhagen, and T. Christ, *Ca(2+)-Currents in Human Induced Pluripotent Stem Cell-Derived Cardiomyocytes Effects of Two Different Culture Conditions.* Front Pharmacol, 2016. 7: p. 300. PMC5018497
149. Valencik M L, and McDonald J A. Codon optimization markedly improves doxycycline regulated gene expression in the mouse heart. *Transgenic Res.* 2001; 10(3):269-75.
150. Van Petegem, F., K. A. Clark, F. C. Chatelain, and D. L. Minor, Jr., *Structure of a complex between a voltage-gated calcium channel beta-subunit and an alpha-subunit domain.* Nature, 2004. 429(6992): p. 671-5. PMC3076333
151. Van Petegem, F., K. E. Duderstadt, K. A. Clark, M. Wang, and D. L. Minor, Jr., *Alanine-scanning mutagenesis defines a conserved energetic hotspot in the CaValpha1 AID-CaVbeta interaction site that is critical for channel modulation.* Structure, 2008. 16(2): p. 280-94. PMC3018278
152. Waithe D, Ferron L, Page K M, Chaggar K, and Dolphin A C. Beta-subunits promote the expression of Ca(V)2.2 channels by reducing their proteasomal degradation. *J Biol Chem.* 2011; 286(11):9598-611.
153. Wan, E., J. Abrams, R. L. Weinberg, A. N. Katchman, J. Bayne, S. I. Zakharov, L. Yang, J. P. Morrow, H. Garan, and S. O. Marx, *Aberrant sodium influx causes cardiomyopathy and atrial fibrillation in mice.* J Clin Invest, 2016. 126(1): p. 112-22. PMC4701549
154. Wang, H., M. J. Kohr, C. J. Traynham, and M. T. Ziolo, *Phosphodiesterase 5 restricts NOS3/Soluble guanylate cyclase signaling to L-type Ca2+ current in cardiac myocytes.* J Mol Cell Cardiol, 2009. 47(2): p. 304-14. PMC2703689
155. Wang, H., M. J. Kohr, D. G. Wheeler, and M. T. Ziolo, *Endothelial nitric oxide synthase decreases beta-adrenergic responsiveness via inhibition of the L-type Ca2+ current.* Am J Physiol Heart Circ Physiol, 2008. 294(3): p. H1473-80. PMC2744450
156. Wang, W., A. P. Landstrom, Q. Wang, M. L. Munro, D. Beavers, M. J. Ackerman, C. Soeller, and X. H. Wehrens, *Reduced junctional Na+/Ca2+-exchanger activity contributes to sarcoplasmic reticulum Ca2+ leak in junctophilin-2-deficient mice.* Am J Physiol Heart Circ Physiol, 2014. 307(9): p. H1317-26. PMC4217007
157. Wehrens X H, Lehnart S E, Reiken S R, and Marks A R. Ca2+/calmodulin-dependent protein kinase II phosphorylation regulates the cardiac ryanodine receptor. *Circ Res.* 2004; 94(6):e61-70.
158. Wei, B., H. Wei, and J. P. Jin, *Dysferlin deficiency blunts beta-adrenergic-dependent lusitropic function of mouse heart.* J Physiol, 2015. 593(23): p. 5127-44. PMC4666988
159. Weissgerber P, Held B, Bloch W, Kaestner L, Chien K R, Fleischmann B K, et al. Reduced cardiac L-type Ca2+ current in Ca(V)beta2-/- embryos impairs cardiac development and contraction with secondary defects in vascular maturation. *Circ Res.* 2006; 99(7):749-57.
160. Wollert, K. C., S. Yurukova, A. Kilic, F. Begrow, B. Fiedler, S. Gambaryan, U. Walter, S. M. Lohmann, and M. Kuhn, *Increased effects of C-type natriuretic peptide on contractility and calcium regulation in murine hearts overexpressing cyclic GMP-dependent protein kinase I.* Br J Pharmacol, 2003. 140(7): p. 1227-36. PMC1574150
161. Xu X, Marx S O, and Colecraft H M. Molecular mechanisms, and selective pharmacological rescue, of Rem-inhibited CaV1.2 channels in heart. *Circ Res.* 2010; 107(5):620-30.

162. Yamada, M., K. Ohta, A. Niwa, N. Tsujino, T. Nakada, and M. Hirose, *Contribution of L-type Ca2+ channels to early afterdepolarizations induced by I Kr and I Ks channel suppression in guinea pig ventricular myocytes.* J Membr Biol, 2008. 222(3): p. 151-66.
163. Yang, L., A. Katchman, R. L. Weinberg, J. Abrams, T. Samad, E. Wan, G. S. Pitt, and S. O. Marx, *The PDZ motif of the alpha1C subunit is not required for surface trafficking and adrenergic modulation of CaV1.2 channel in the heart.* J Biol Chem, 2015. 290(4): p. 2166-74. PMC4303668
164. Yang, L., A. Katchman, T. Samad, J. P. Morrow, R. L. Weinberg, and S. O. Marx, *beta-adrenergic regulation of the L-type Ca2+ channel does not require phosphorylation of alpha1C Ser1700.* Circ Res, 2013. 113(7): p. 871-80. PMC3864014
165. Yang, L., G. Liu, S. I. Zakharov, A. M. Bellinger, M. Mongillo, and S. O. Marx, *Protein kinase G phosphorylates Cav1.2 alpha1c and beta2 subunits.* Circ Res, 2007. 101(5): p. 465-74.
166. Yang, Z., G. Shi, C. Li, H. Wang, K. Liu, and Y. Liu, *Electrophysiologic effects of nicorandil on the guinea pig long QT1 syndrome model.* J Cardiovasc Electrophysiol, 2004. 15(7): p. 815-20.
167. Zakharov, S. I., S. Pieramici, G. K. Kumar, N. R. Prabhakar, and R. D. Harvey, *Nitric oxide synthase activity in guinea pig ventricular myocytes is not involved in muscarinic inhibition of cAMP-regulated ion channels.* Circ Res, 1996. 78(5): p. 925-35.
168. Zeng, J. and Y. Rudy, *Early afterdepolarizations in cardiac myocytes: mechanism and rate dependence.* Biophys J, 1995. 68(3): p. 949-64. PMC1281819
169. Zhou, F. F., Y. Xue, G. L. Chen, and X. Yao, *GPS: a novel group-based phosphorylation predicting and scoring method.* Biochem Biophys Res Commun, 2004. 325 (4): p. 1443-8.
170. Ziolo, M. T., L. S. Maier, V. Piacentino, 3rd, J. Bossuyt, S. R. Houser, and D. M. Bers, *Myocyte nitric oxide synthase 2 contributes to blunted beta-adrenergic response in failing human hearts by decreasing Ca2+ transients.* Circulation, 2004. 109(15): p. 1886-91.
171. Ziolo, M. T., M. J. Kohr, and H. Wang, *Nitric oxide signaling and the regulation of myocardial function.* J Mol Cell Cardiol, 2008. 45(5): p. 625-32. PMC3282562
172. Ziolo, M. T., S. J. Lewandowski, J. M. Smith, F. D. Romano, and G. M. Wahler, *Inhibition of cyclic GMP hydrolysis with zaprinast reduces basal and cyclic AMP-elevated L-type calcium current in guinea-pig ventricular myocytes.* Br J Pharmacol, 2003. 138(5): p. 986-94. PMC1573723
173. Zybailov, B., A. L. Mosley, M. E. Sardiu, M. K. Coleman, L. Florens, and M. P. Washburn, *Statistical analysis of membrane proteome expression changes in Saccharomyces cerevisiae.* J Proteome Res, 2006. 5(9): p. 2339-47.

What is claimed is:

1. A method for identifying a candidate agent that can treat or ameliorate a heart condition in a subject, comprising the steps of:
   a) obtaining a first construct comprising a first signaling moiety attached to a CaVB (beta subunit of a voltage-gated L-type calcium channel (CaV1.2)), and obtaining a second construct comprising a second signaling moiety attached to a I-IIC alpha interaction domain (AID) of CaV1.2;
   b) co-expressing the first and second constructs in an appropriate cell line;
   c) determining the intensity of a signal specifically generated from the close proximity of the two signaling moieties where the signal can either be self-generated or induced by exposing the cells from step b) to a substrate of the signaling moiety;
   d) repeating steps a) to c) by additionally incubating the cells with a candidate agent before step c); and
   e) identifying the candidate agent as being able to treat or ameliorate the heart condition, if the intensity of the signal determined in step d) is less than that of step c), wherein the heart condition is associated with abnormal beta-adrenergic receptor activation on calcium levels in cardiomyocytes in the subject, or with normal effect of beta-adrenergic receptor activation on contractility that may be detrimental to the subject.

2. The method according to claim 1, wherein the heart condition is selected from the group consisting of arrhythmia, hypertrophic cardiomyopathy, hypertension, diastolic dysfunction, systolic heart failure, and coronary artery disease.

3. The method according to claim 2, wherein the heart condition is catecholaminergic polymorphic ventricular tachycardia (CPVT), long QT syndrome (LQTS) or arrhythmogenic right ventricular dysplasia (ARVD) in inherited ventricular arrhythmia, or hemodynamic consequences resulted from diastolic dysfunction or left ventricular outflow tract obstruction in hypertrophic cardiomyopathy, or arrhythmia consequences in hypertrophic cardiomyopathy, or angina.

4. The method according to claim 1, wherein the signaling moiety is selected from a peroxidase enzyme, luciferase, fluorophore, fluorescent protein, fluorescent dye, lanthanide, quantum dot, biotin, digoxin, hapten, epitope, and radioisotope.

5. The method according to claim 1, wherein the candidate agent is selected from antibodies, RNAi, siRNA, shRNA, antisense sequences, peptides and small molecules.

6. The method according to claim 1, wherein the signal is selected from color, fluorescence, bioluminescence and radiation.

7. A method for identifying a candidate agent that can treat or ameliorate a heart condition in a subject, comprising the steps of:
   a) immobilizing small peptides containing a functional I-IIC alpha interaction domain (AID) of a voltage-gated L-type calcium channel (CaV1.2) site onto a surface;
   b) incubating a CaVB (beta subunit of CaV1.2) protein that is attached to a signaling moiety;
   c) rinsing the surface to remove any CaVB protein that is not immobilized;
   d) determining the intensity of the signal generated from the surface, where the signal can either be self-generated or induced by exposing the surface to a substrate of the signaling moiety;
   e) repeating steps a) to d) by additionally adding a candidate agent in step b); and
   f) identifying the candidate agent as being able to treat or ameliorate the effects of the heart condition, if the color intensity determined in step e) is less than that of step d), wherein the heart condition is associated with abnormal beta-adrenergic receptor activation on calcium levels in cardiomyocytes in the subject, or with normal effect of beta-adrenergic receptor activation on contractility that may be detrimental to the subject.

8. A method for identifying a candidate agent that can treat or ameliorate a heart condition in a subject, comprising the steps of:
   a) obtaining a first construct comprising an amino or carboxyl terminal portion of a luciferase attached to a CaVB beta subunit of a voltage-gated L-type calcium channel (CaV1.2)), and obtaining a second construct comprising a carboxyl or amino terminal portion of the luciferase attached to a I-IIC alpha interaction domain (AID) of CaV1.2;
   b) co-expressing the first and second constructs in an appropriate cell line;
   c) exposing the cells from step b) to a substrate of the luciferase, and determining the intensity of the signal produced;
   d) repeating steps a) to c) by additionally incubating the cells with a candidate agent before step c); and
   e) identifying the candidate agent as being able to treat or ameliorate the heart condition, if the bioluminescence signal intensity determined in step d) is less than that of step c),
   wherein the heart condition is associated with abnormal beta-adrenergic receptor activation on calcium levels in cardiomyocytes in the subject, or with normal effect of beta-adrenergic receptor activation on contractility that may be detrimental to the subject.

9. A method for identifying a candidate agent that can treat or ameliorate a heart condition in a subject, comprising the steps of:
   a) obtaining a first construct comprising a Flag-tag or HIS-tag attached to amino or carboxyl terminus of a CaVB (beta subunit of a voltage-gated L-type calcium channel (CaV1.2)), and obtaining a second construct comprising a HIS-tag or Flag-tag attached to amino or carboxyl terminus of a I-IIC alpha interaction domain (AID) of CaV1.2;
   b) co-expressing the first and second constructs in bacterial cells;
   c) purifying the first and second constructs;
   d) incubating the first and second constructs in solution;
   e) using anti-Flag and anti-His fluorescent antibodies to tag the first and second constructs;
   f) determining the ratio between the intensities of fluorescence at 665 nm and 615 nm (665 nm/615 nm);
   g) repeating steps d) to f) by additionally incubating the first and second constructs with a candidate agent before step e); and
   h) identifying the candidate agent as being able to treat or ameliorate the heart condition, if the ratio determined in step g) is less than that of step f),
   wherein the heart condition is associated with abnormal beta-adrenergic receptor activation on calcium levels in cardiomyocytes in the subject, or with normal effect of beta-adrenergic receptor activation on contractility that may be detrimental to the subject.

10. The method according to claim 9, wherein the heart condition is selected from the group consisting of arrhythmia, hypertrophic cardiomyopathy, hypertension, diastolic dysfunction, systolic heart failure, and coronary artery disease.

11. The method according to claim 10, wherein the heart condition is catecholaminergic polymorphic ventricular tachycardia (CPVT), long QT syndrome (LQTS) or arrhythmogenic right ventricular dysplasia (ARVD) in inherited ventricular arrhythmia, or hemodynamic consequences resulted from diastolic dysfunction or left ventricular outflow tract obstruction in hypertrophic cardiomyopathy, or arrhythmia consequences in hypertrophic cardiomyopathy, or angina.

12. The method according to claim 9, wherein the Flag-tag or the His-Tag is replaced by a tag selected from the group consisting of c-myc, FITC, GST, HA, V5 tag, and Streptavidin.

* * * * *